(12) United States Patent
Hudson et al.

(10) Patent No.: US 10,689,416 B2
(45) Date of Patent: *Jun. 23, 2020

(54) PEPTIDE-BASED PROTEASOME INHIBITORS FOR TREATING CONDITIONS MEDIATED BY SENESCENT CELLS AND FOR TREATING CANCER

(71) Applicant: UNITY BIOTECHNOLOGY, INC., Brisbane, CA (US)

(72) Inventors: Ryan Hudson, Brisbane, CA (US); Anne-Marie Beausoleil, Brisbane, CA (US); F. Anthony Romero, Brisbane, CA (US); Remi-Martin Laberge, Brisbane, CA (US)

(73) Assignee: Unity Biotechnology, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/393,651

(22) Filed: Apr. 24, 2019

(65) Prior Publication Data

US 2019/0248837 A1 Aug. 15, 2019

Related U.S. Application Data

(63) Continuation-in-part of application No. PCT/US2018/068190, filed on Dec. 31, 2018, and a continuation-in-part of application No. PCT/US2018/068003, filed on Dec. 28, 2018.

(60) Provisional application No. 62/612,411, filed on Dec. 30, 2017, provisional application No. 62/612,414, filed on Dec. 30, 2017, provisional application No. 62/612,416, filed on Dec. 30, 2017, provisional application No. 62/612,417, filed on Dec. 30, 2017, provisional application No. 62/612,418, filed on Dec. 30, 2017, provisional application No. 62/676,692, filed on May 25, 2018.

(51) Int. Cl.

| | | |
|---|---|---|
| *C07K 7/06* | (2006.01) |
| *A61K 38/06* | (2006.01) |
| *A61P 27/02* | (2006.01) |
| *A61P 9/10* | (2006.01) |
| *A61P 19/02* | (2006.01) |
| *A61P 35/00* | (2006.01) |
| *A61K 31/496* | (2006.01) |
| *A61K 31/519* | (2006.01) |
| *A61K 38/05* | (2006.01) |
| *A61K 38/07* | (2006.01) |
| *C07D 201/00* | (2006.01) |
| *C07D 303/32* | (2006.01) |
| *C07K 5/06* | (2006.01) |
| *C07K 5/08* | (2006.01) |
| *C07K 5/083* | (2006.01) |
| *C07K 5/10* | (2006.01) |
| *C07K 5/107* | (2006.01) |
| *A61K 38/00* | (2006.01) |

(52) U.S. Cl.
CPC .............. *C07K 7/06* (2013.01); *A61K 31/496* (2013.01); *A61K 31/519* (2013.01); *A61K 38/05* (2013.01); *A61K 38/06* (2013.01); *A61K 38/07* (2013.01); *A61P 9/10* (2018.01); *A61P 19/02* (2018.01); *A61P 27/02* (2018.01); *A61P 35/00* (2018.01); *C07D 201/00* (2013.01); *C07D 303/32* (2013.01); *C07K 5/06* (2013.01); *C07K 5/08* (2013.01); *C07K 5/0808* (2013.01); *C07K 5/10* (2013.01); *C07K 5/1016* (2013.01); *A61K 38/00* (2013.01)

(58) Field of Classification Search
CPC ........... A61K 38/06; A61K 38/07; C07K 7/06
See application file for complete search history.

(56) References Cited

U.S. PATENT DOCUMENTS

| | | |
|---|---|---|
| 7,232,818 B2 | 6/2007 | Smyth et al. |
| 8,563,735 B2 | 10/2013 | Bruncko et al. |
| 8,853,147 B2 | 10/2014 | Kirk et al. |
| 9,248,140 B2 | 2/2016 | Diebold et al. |

(Continued)

FOREIGN PATENT DOCUMENTS

WO    WO2015032621    3/2015

OTHER PUBLICATIONS

Baker et al., Nature 479, 232 (2011). doi:10.1038/nature10600. (Year: 2011).*

(Continued)

*Primary Examiner* — James H Alstrum-Acevedo
*Assistant Examiner* — Kaipeen E Yang
(74) *Attorney, Agent, or Firm* — Rudy J. Ng; Bozicevic, Field & Francis LLP

(57) ABSTRACT

The proteasome inhibitors of this invention include peptide-based compounds with a short linear sequence of amino acids. An oxo or thio group is attached to the N-terminal amino acid. A protein-reactive electrophilic group such as an epoxyketone, an aziridinylketone, or a beta-lactone is attached to the C-terminal amino acid. Upon contact with a proteasome complex in a target cell, the electrophilic group reacts with a functional group in or near a binding pocket or active site of the proteasome, forming a covalent bond and thereby inactivating the proteasome. These and other proteasome inhibitors can be screened for binding affinity and an ability to selectively eliminate senescent cells or cancer cells. Compounds that selectively remove senescent cells can be developed for the treatment of conditions such as osteoarthritis, ophthalmic disease, pulmonary disease, and atherosclerosis.

10 Claims, 29 Drawing Sheets

(56) References Cited

U.S. PATENT DOCUMENTS

| | | | |
|---|---|---|---|
| 9,441,012 | B2 | 9/2016 | Slassi et al. |
| 9,657,057 | B2 | 5/2017 | McMinn et al. |
| 9,849,128 | B2 | 12/2017 | Laberge et al. |
| 9,901,080 | B2 | 2/2018 | Campisi et al. |
| 9,968,076 | B2 | 5/2018 | Kirkland et al. |
| 10,010,546 | B2 | 7/2018 | Laberge et al. |
| 10,195,213 | B2 | 2/2019 | David |
| 2016/0031934 | A1 | 2/2016 | McMinn |
| 2016/0122758 | A1 | 5/2016 | Krizhanovsky et al. |
| 2017/0056421 | A1 | 3/2017 | Zhou et al. |
| 2017/0216286 | A1 | 8/2017 | Kirkland et al. |
| 2018/0000816 | A1 | 1/2018 | David et al. |

OTHER PUBLICATIONS

Baar et al. (2017) "Targeted Apoptosis of Senescent Cells Restores Tissue Homeostasis in Response to Chemotoxicity and Aging," Cell, 169(1): 132-147.

Baker et al. (2016) "Naturally occurring p16Ink4a-positive cells shorten healthy lifespan," Nature, 530 (7589): 184-189.

Blagosklonny et al. (2013) "Selective anti-cancer agents as anti-aging drugs," Cancer Biology & Therapy, 14(12): 1092-1097.

Braun et al., (2012) "Cellular Senescence Limits Regenerative Capacity and Allograft Survival," J. Am Soc Nephrol., 23(9): 1467-1473.

Campisi & Robert (2014) "Cell senescence, role in aging and age-related diseases," Interdiscip Top Gerontol, 39: 45-61.

Childs et al., (2017) "Senescent cells: an emerging target for diseases of aging," Nat Rev Drug Discov., 16(10): 718-735.

Chondrogianni et al., (2003) "Central Role of the Proteasome in Senescence and Survival of Human Fibroblasts," The Journal of Biological Chemistry, 287(30): 28026-28037.

Deschênes-Simard et al., (2014) "Cellular senescence and protein degradation," Cell Cycle 13(12): 1840-1858.

Jeon et al., (2017) "Local clearance of senescent cells attenuates the development of post-traumatic osteoarthritis and creates a pro-regenerative environment," Nature Medicine, 1-9.

Kirkland & Tchkonia (2015) "Clinical Strategies and Animal Models for Developing Senolytic Agents," Exp Gerontol., 68: 19-25.

Kisselev et al., (2012) "Proteasome Inhibitors: An Expanding Army Attacking a Unique Target," 19(1) 99-115.

Metcalf et al., (2014) "Proteasome inhibitor patents (2010- present)" Expert Opinion Ther. Patents 24(4): 369-382.

Zhu et al., (2017) "New agents that target senescent cells: the flavone, fisetin, and the BCL-XL inhibitors, A1331852 and A1155463," Aging, 9: 1-9.

\* cited by examiner

*Structures of exemplary proteasome inhibitor compounds*

UN001

UN002

UN003

UN004

UN005

UN006

UN007

UN008

UN010

UN011

UN013

UN014

*Structures of exemplary proteasome inhibitor compounds*

FIG. 1B *continued*
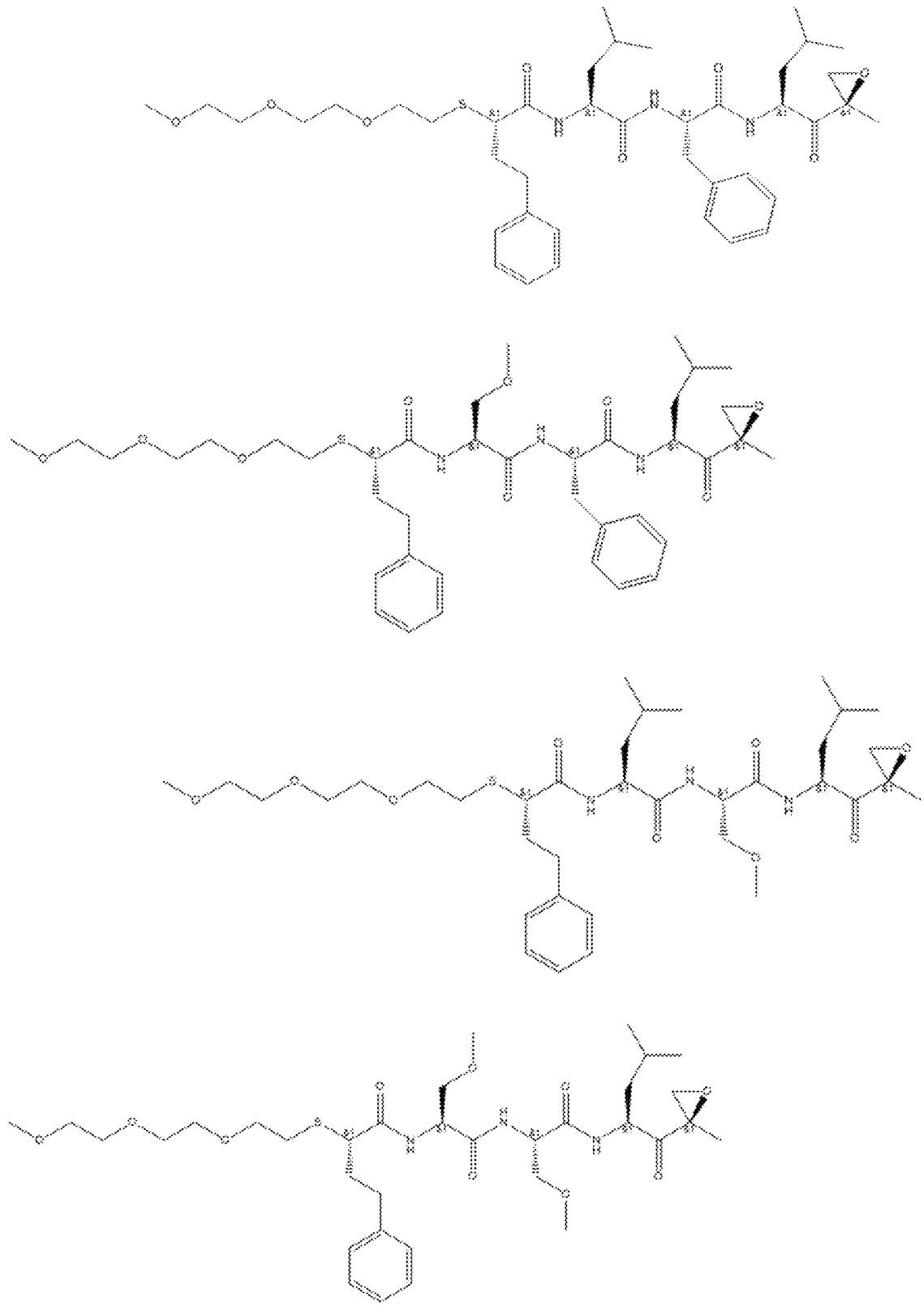

FIG. 1B _continued_
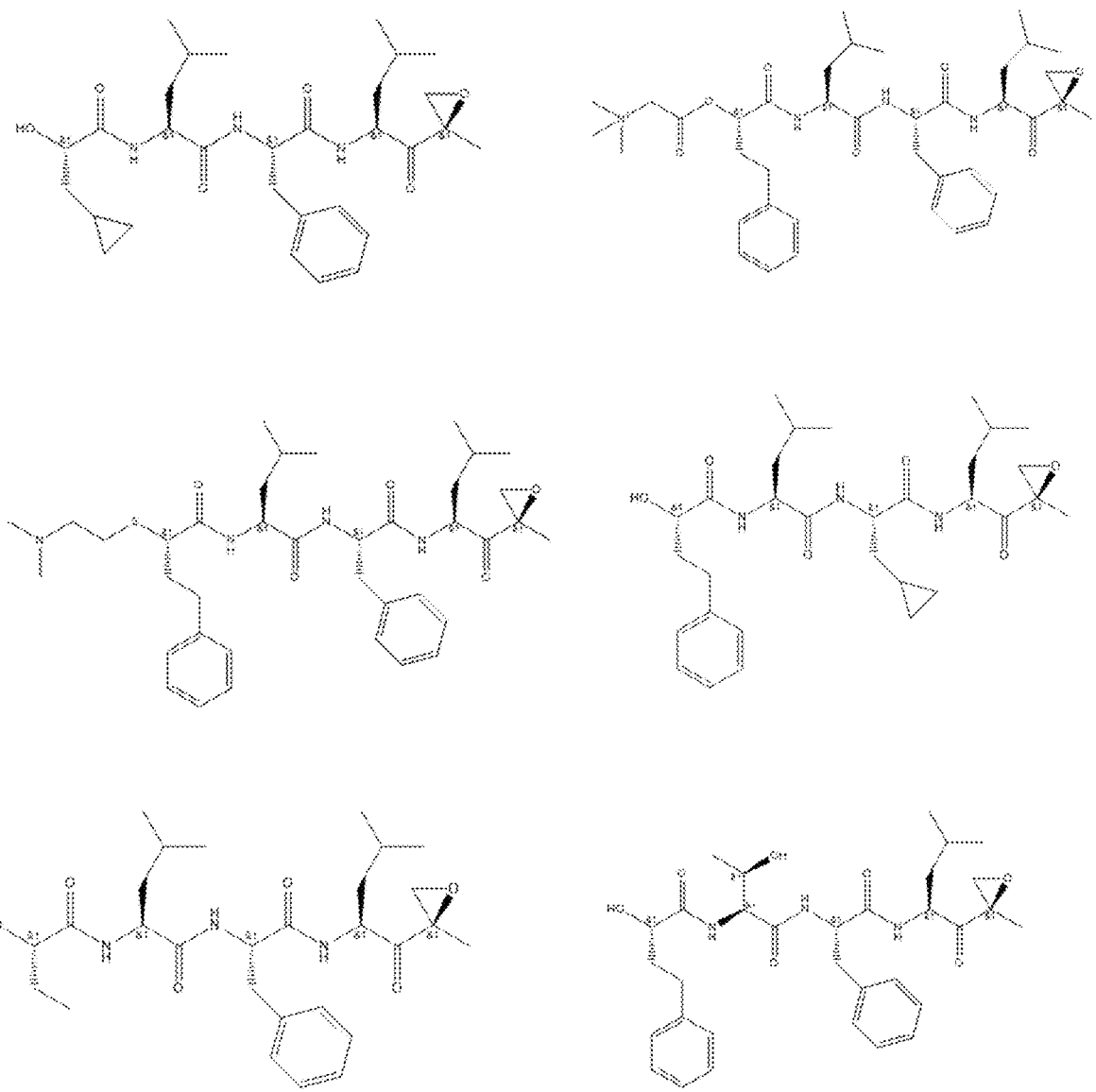

FIG. 1B *continued*
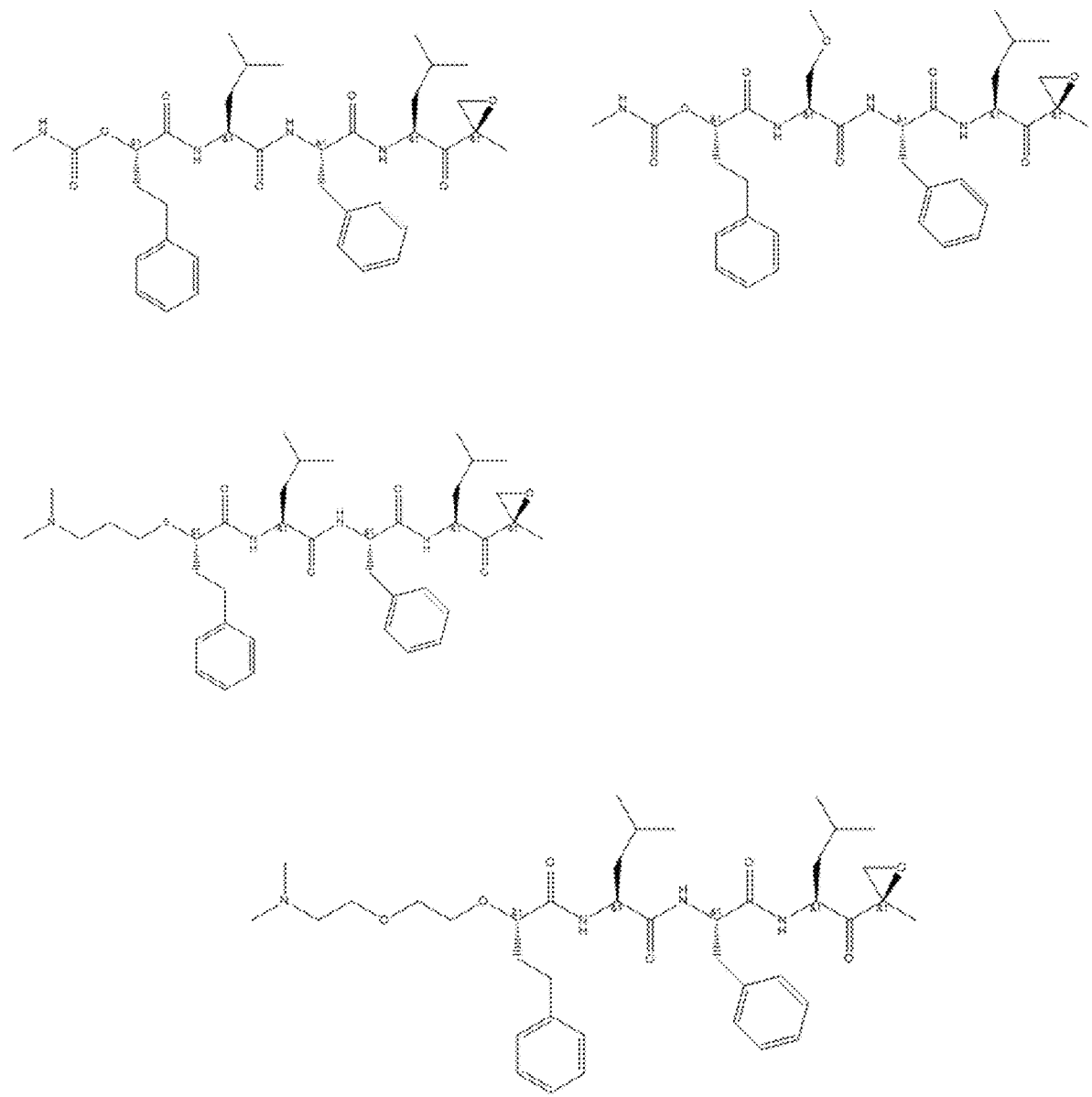

FIG. 1C

*Structures and chemical names of exemplary proteasome inhibitor compounds* methyl (R)-3-(((S)-4-methyl-1-(((S)-1-(((S)-4-methyl-1-((R)-2-methyloxiran-2-yl)-1-oxopentan-2-yl)amino)-1-oxo-3-phenylpropan-2-yl)amino)-1-oxopentan-2-yl)carbamoyl)-5-phenylpentanoate

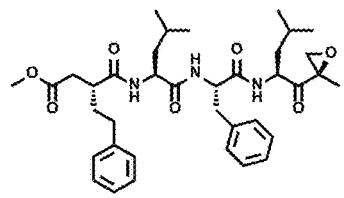

(S)-2-((S)-2-hydroxypropanamido)-4-methyl-N-((S)-1-(((S)-4-methyl-1-((R)-2-methyloxiran-2-yl)-1-oxopentan-2-yl)amino)-1-oxo-3-phenylpropan-2-yl)pentanamide

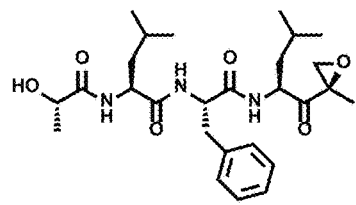

N-((S)-4-methyl-1-(((S)-1-(((S)-4-methyl-1-((R)-2-methyloxiran-2-yl)-1-oxopentan-2-yl)amino)-1-oxo-3-phenylpropan-2-yl)amino)-1-oxopentan-2-yl)-2,5,8-trioxa-11-thiatridecan-13-amide

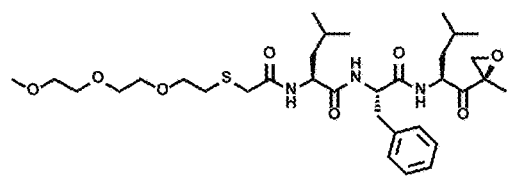

(S)-2-((S)-2-(azetidin-3-yloxy)-4-phenylbutanamido)-4-methyl-N-((S)-1-(((S)-4-methyl-1-((R)-2-methyloxiran-2-yl)-1-oxopentan-2-yl)amino)-1-oxo-3-phenylpropan-2-yl)pentanamide

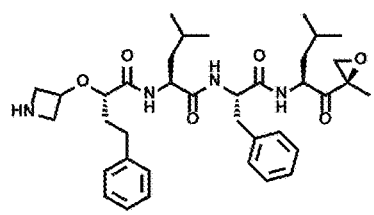

FIG. 1C continued (S)-N-((S)-3-(difluoromethoxy)-1-(((S)-1-(((S)-4-methyl-1-((R)-2-methyloxiran-2-yl)-1-oxopentan-2-yl)amino)-1-oxo-3-phenylpropan-2-yl)amino)-1-oxopropan-2-yl)-2-hydroxy-4-phenylbutanamide

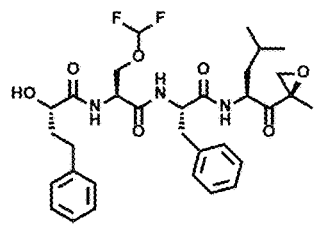

(S)-2-((S)-3-(difluoromethoxy)-2-hydroxypropanamido)-4-methyl-N-((S)-1-(((S)-4-methyl-1-((R)-2-methyloxiran-2-yl)-1-oxopentan-2-yl)amino)-1-oxo-3-phenylpropan-2-yl)pentanamide

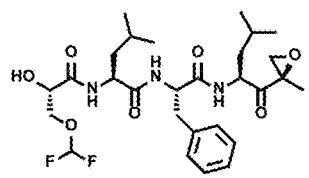

(S)-2-((S)-2-hydroxy-4-phenylbutanamido)-4-methyl-N-((S)-1-(((S)-4-methyl-1-((R)-2-methyloxiran-2-yl)-1-oxopentan-2-yl)amino)-1-oxo-3-phenylpropan-2-yl)pentanamide
Synthesis of benzyl (tert-butoxycarbonyl)-L-leucyl-L-phenylalaninate

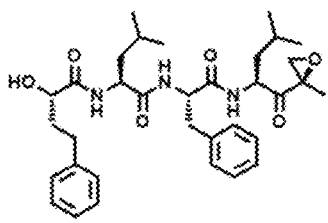

(S)-2-((S)-3-ethoxy-2-hydroxypropanamido)-4-methyl-N-((S)-1-(((S)-4-methyl-1-((R)-2-methyloxiran-2-yl)-1-oxopentan-2-yl)amino)-1-oxo-3-phenylpropan-2-yl)pentanamide

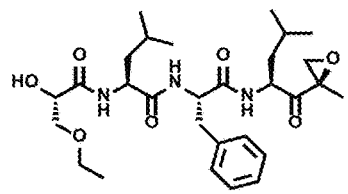

FIG. 1C continued (S)-2-((S)-3-cyclopropoxy-2-hydroxypropanamido)-4-methyl-N-((S)-1-(((S)-4-methyl-1-((R)-2-methyloxiran-2-yl)-1-oxopentan-2-yl)amino)-1-oxo-3-phenylpropan-2-yl)pentanamide

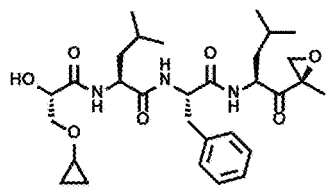

(S)-2-hydroxy-5-methyl-N-((S)-4-methyl-1-(((S)-1-(((S)-4-methyl-1-((R)-2-methyloxiran-2-yl)-1-oxopentan-2-yl)amino)-1-oxo-3-phenylpropan-2-yl)amino)-1-oxopentan-2-yl)hex-5-enamide

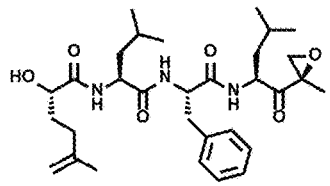

(S)-2-((S)-2-hydroxybutanamido)-4-methyl-N-((S)-1-(((S)-4-methyl-1-((R)-2-methyloxiran-2-yl)-1-oxopentan-2-yl)amino)-1-oxo-3-phenylpropan-2-yl)pentanamide

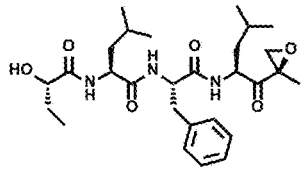

(S)-2-((2S,3R)-2-hydroxy-3-methoxybutanamido)-4-methyl-N-((S)-1-(((S)-4-methyl-1-((R)-2-methyloxiran-2-yl)-1-oxopentan-2-yl)amino)-1-oxo-3-phenylpropan-2-yl)pentanamide

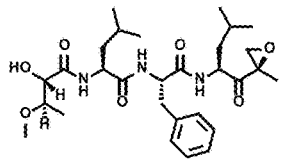

methyl (R)-3-(((S)-4-methyl-1-(((S)-1-(((S)-4-methyl-1-((R)-2-methyloxiran-2-yl)-1-oxopentan-2-yl)amino)-1-oxo-3-phenylpropan-2-yl)amino)-1-oxopentan-2-yl)carbamoyl)-5-phenylpentanoate

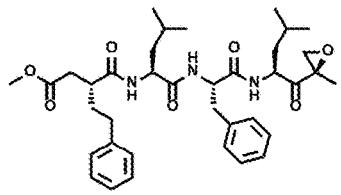

FIG. 1C *continued*

(S)-2-((S)-2-hydroxypropanamido)-4-methyl-N-((S)-1-(((S)-4-methyl-1-((R)-2-methyloxiran-2-yl)-1-oxopentan-2-yl)amino)-1-oxo-3-phenylpropan-2-yl)pentanamide

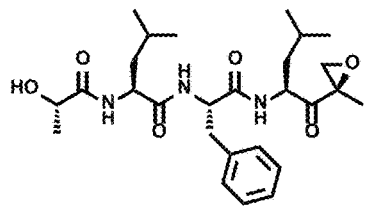

N-((S)-4-methyl-1-(((S)-1-(((S)-4-methyl-1-((R)-2-methyloxiran-2-yl)-1-oxopentan-2-yl)amino)-1-oxo-3-phenylpropan-2-yl)amino)-1-oxopentan-2-yl)-2,5,8-trioxa-11-thiatridecan-13-amide

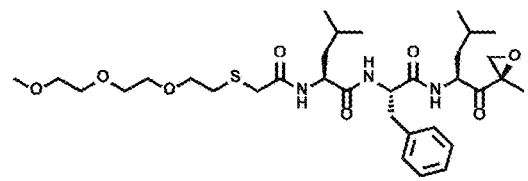

(S)-2-((S)-2-(azetidin-3-yloxy)-4-phenylbutanamido)-4-methyl-N-((S)-1-(((S)-4-methyl-1-((R)-2-methyloxiran-2-yl)-1-oxopentan-2-yl)amino)-1-oxo-3-phenylpropan-2-yl)pentanamide

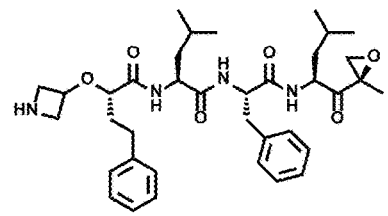

(S)-N-((S)-3-(difluoromethoxy)-1-(((S)-1-(((S)-4-methyl-1-((R)-2-methyloxiran-2-yl)-1-oxopentan-2-yl)amino)-1-oxo-3-phenylpropan-2-yl)amino)-1-oxopropan-2-yl)-2-hydroxy-4-phenylbutanamide

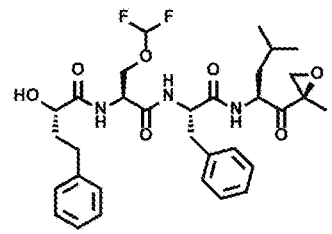

FIG. 1C continued (S)-2-((S)-3-(difluoromethoxy)-2-hydroxypropanamido)-4-methyl-N-((S)-1-(((S)-4-methyl-1-((R)-2-methyloxiran-2-yl)-1-oxopentan-2-yl)amino)-1-oxo-3-phenylpropan-2-yl)pentanamide

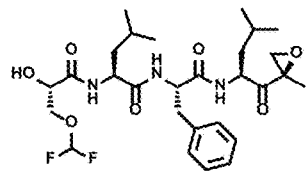

(S)-2-((S)-3-ethoxy-2-hydroxypropanamido)-4-methyl-N-((S)-1-(((S)-4-methyl-1-((R)-2-methyloxiran-2-yl)-1-oxopentan-2-yl)amino)-1-oxo-3-phenylpropan-2-yl)pentanamide

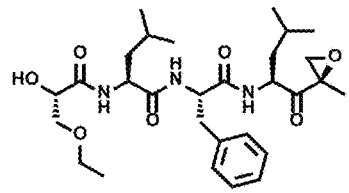

(S)-2-((S)-3-cyclopropoxy-2-hydroxypropanamido)-4-methyl-N-((S)-1-(((S)-4-methyl-1-((R)-2-methyloxiran-2-yl)-1-oxopentan-2-yl)amino)-1-oxo-3-phenylpropan-2-yl)pentanamide

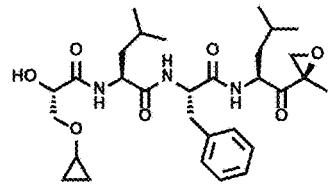

(S)-2-hydroxy-5-methyl-N-((S)-4-methyl-1-(((S)-1-(((S)-4-methyl-1-((R)-2-methyloxiran-2-yl)-1-oxopentan-2-yl)amino)-1-oxo-3-phenylpropan-2-yl)amino)-1-oxopentan-2-yl)hex-5-enamide

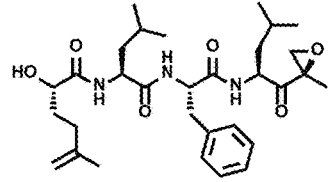

FIG. 1C continued (S)-2-((S)-2-hydroxybutanamido)-4-methyl-N-((S)-1-(((S)-4-methyl-1-((R)-2-methyloxiran-2-yl)-1-oxopentan-2-yl)amino)-1-oxo-3-phenylpropan-2-yl)pentanamide

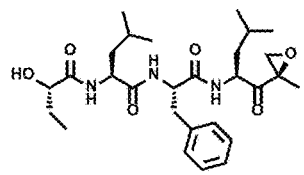

(S)-2-((2S,3R)-2-hydroxy-3-methoxybutanamido)-4-methyl-N-((S)-1-(((S)-4-methyl-1-((R)-2-methyloxiran-2-yl)-2-yl)-1-oxopentan-2-yl)amino)-1-oxo-3-phenylpropan-2-yl)pentanamide

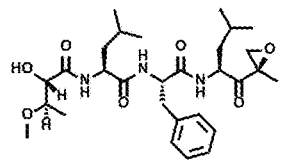

(S)-2-((S)-2-hydroxy-4-phenylbutanamido)-4-methyl-N-((S)-1-(((S)-4-methyl-1-((R)-2-methyloxiran-2-yl)-1-oxopentan-2-yl)amino)-1-oxo-3-phenylpropan-2-yl)pentanamide

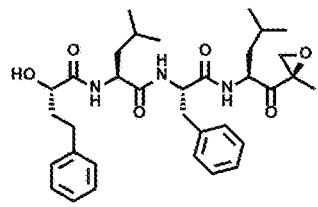

(S)-1-(((S)-4-methyl-1-(((S)-1-(((S)-4-methyl-1-((R)-2-methyloxiran-2-yl)-1-oxopentan-2-yl)amino)-1-oxo-3-phenylpropan-2-yl)amino)-1-oxopentan-2-yl)amino)-1-oxo-4-phenylbutan-2-yl acetate

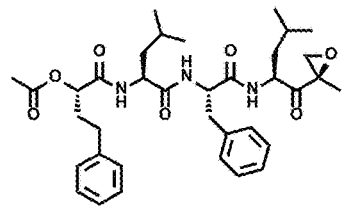

FIG. 1C continued (S)-1-(((S)-4-methyl-1-(((S)-1-(((S)-4-methyl-1-((R)-2-methyloxiran-2-yl)-1-oxopentan-2-yl)amino)-1-oxo-3-phenylpropan-2-yl)amino)-1-oxopentan-2-yl)amino)-1-oxo-4-phenylbutan-2-yl 2-morpholinoacetate

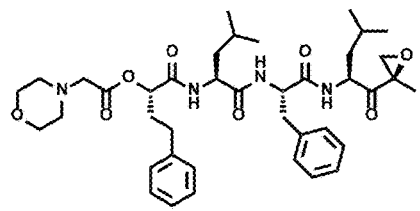

(S)-N-((S)-4-methyl-1-(((S)-1-(((S)-4-methyl-1-((R)-2-methyloxiran-2-yl)-1-oxopentan-2-yl)amino)-1-oxo-3-phenylpropan-2-yl)amino)-1-oxopentan-2-yl)-12-phenethyl-2,5,8-trioxa-11-thiatridecan-13-amide

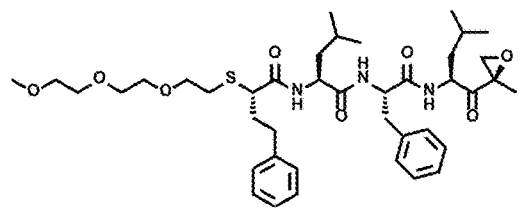

(S)-2-((S)-2-methoxy-4-phenylbutanamido)-4-methyl-N-((S)-1-(((S)-4-methyl-1-((R)-2-methyloxiran-2-yl)-1-oxopentan-2-yl)amino)-1-oxo-3-phenylpropan-2-yl)pentanamide

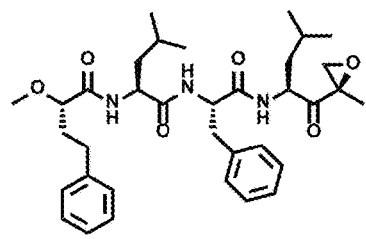

(S)-2-((S)-2-hydroxybutanamido)-4-methyl-N-((S)-1-(((S)-4-methyl-1-((R)-2-methyloxiran-2-yl)-1-oxopentan-2-yl)amino)-1-oxo-3-phenylpropan-2-yl)pentanamide

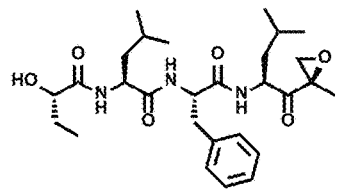

FIG. 1C *continued*

(S)-2-hydroxy-N-((S)-3-methoxy-1-(((S)-1-(((S)-4-methyl-1-((R)-2-methyloxiran-2-yl)-1-oxopentan-2-yl)amino)-1-oxo-3-phenylpropan-2-yl)amino)-1-oxopropan-2-yl)-4-phenylbutanamide

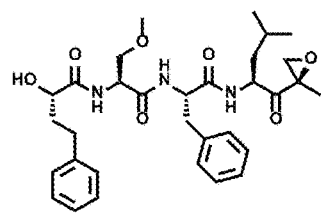

(S)-2-((S)-2-hydroxybutanamido)-4-methyl-N-((S)-1-(((S)-4-methyl-1-((R)-2-methyloxiran-2-yl)-1-oxopentan-2-yl)amino)-1-oxo-3-phenylpropan-2-yl)pentanamide

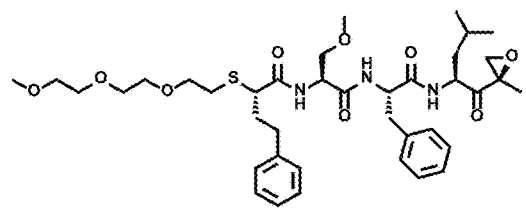

(S)-2-((S)-2-hydroxypentanamido)-4-methyl-N-((S)-1-(((S)-4-methyl-1-((R)-2-methyloxiran-2-yl)-1-oxopentan-2-yl)amino)-1-oxo-3-phenylpropan-2-yl)pentanamide

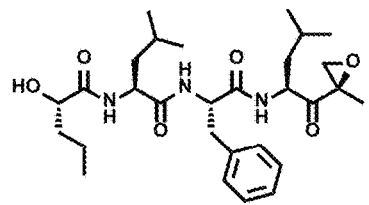

(S)-2-((S)-3-cyclopropyl-2-hydroxypropanamido)-4-methyl-N-((S)-1-(((S)-4-methyl-1-((R)-2-methyloxiran-2-yl)-1-oxopentan-2-yl)amino)-1-oxo-3-phenylpropan-2-yl)pentanamide

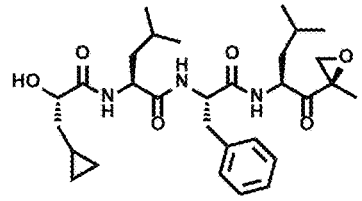

FIG. 1C *continued*

(S)-2-hydroxy-N-((S)-3-methoxy-1-(((S)-3-methoxy-1-(((S)-4-methyl-1-((R)-2-methyloxiran-2-yl)-1-oxopentan-2-yl)amino)-1-oxopropan-2-yl)amino)-1-oxopropan-2-yl)-4-phenylbutanamide

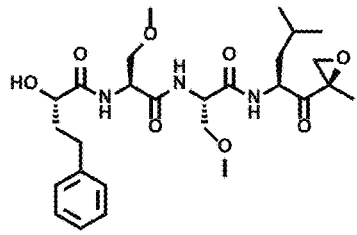

(4S,7S,10S,13S)-10-benzyl-7-isobutyl-N,N,N,15-tetramethyl-13-((R)-2-methyloxirane-2-carbonyl)-2,5,8,11-tetraoxo-4-phenethyl-3-oxa-6,9,12-triazahexadecan-1-aminium

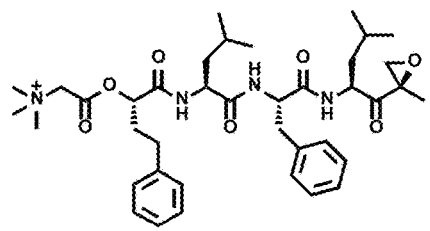

(S)-2-((S)-2-(2-(dimethylamino)ethoxy)-4-phenylbutanamido)-4-methyl-N-((S)-1-(((S)-4-methyl-1-((R)-2-methyloxiran-2-yl)-1-oxopentan-2-yl)amino)-1-oxo-3-phenylpropan-2-yl)pentanamide

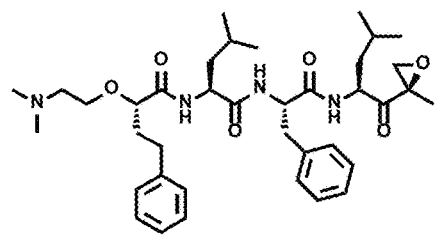

(S)-N-((S)-1-(((S)-3-methoxy-1-(((S)-4-methyl-1-((R)-2-methyloxiran-2-yl)-1-oxopentan-2-yl)amino)-1-oxopropan-2-yl)amino)-4-methyl-1-oxopentan-2-yl)-12-phenethyl-2,5,8-trioxa-11-thiatridecan-13-amide

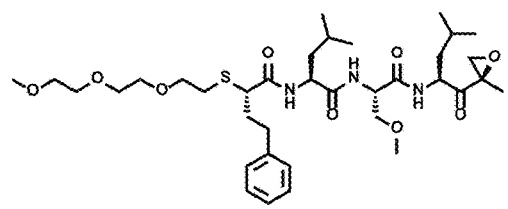

FIG. 1C continued (S)-N-((S)-3-methoxy-1-(((S)-3-methoxy-1-(((S)-4-methyl-1-((R)-2-methyloxiran-2-yl)-1-oxopentan-2-yl)amino)-1-oxopropan-2-yl)amino)-1-oxopropan-2-yl)-12-phenethyl-2,5,8-trioxa-11-thiatridecan-13-amide

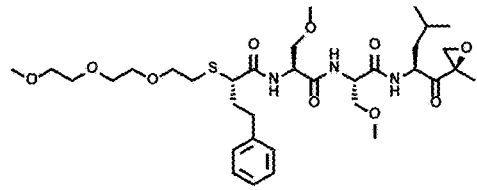

(S)-2-((S)-2-((2-(dimethylamino)ethyl)thio)-4-phenylbutanamido)-4-methyl-N-((S)-1-(((S)-4-methyl-1-((R)-2-methyloxiran-2-yl)-1-oxopentan-2-yl)amino)-1-oxo-3-phenylpropan-2-yl)pentanamide

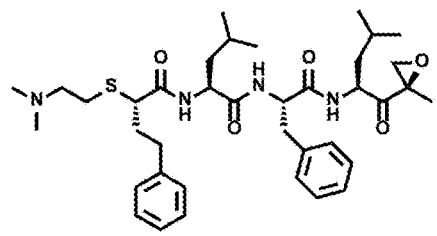

(S)-2-((S)-2-((3-(dimethylamino)propyl)thio)-4-phenylbutanamido)-4-methyl-N-((S)-1-(((S)-4-methyl-1-((R)-2-methyloxiran-2-yl)-1-oxopentan-2-yl)amino)-1-oxo-3-phenylpropan-2-yl)pentanamide

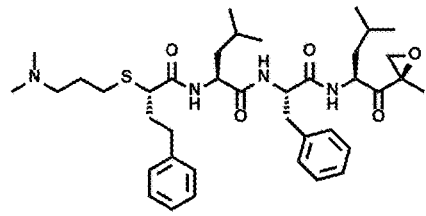

(S)-1-(((S)-4-methyl-1-(((S)-1-(((S)-4-methyl-1-((R)-2-methyloxiran-2-yl)-1-oxopentan-2-yl)amino)-1-oxo-3-phenylpropan-2-yl)amino)-1-oxopentan-2-yl)amino)-1-oxo-4-phenylbutan-2-yl methylcarbamate

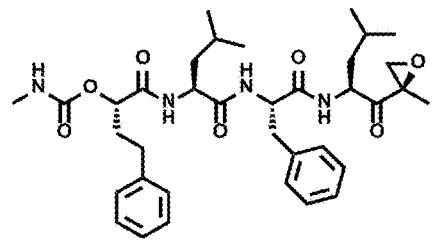

FIG. 1C continued (S)-2-((S)-2-hydroxy-4-phenylbutanamido)-N-((S)-3-methoxy-1-(((S)-4-methyl-1-((R)-2-methyloxiran-2-yl)-1-oxopentan-2-yl)amino)-1-oxopropan-2-yl)-4-methylpentanamide

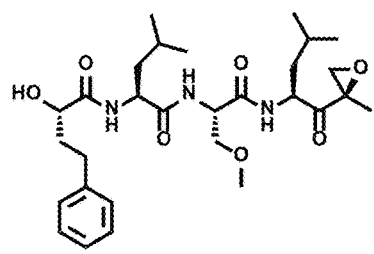

(S)-2-hydroxy-N-((2S,3R)-3-hydroxy-1-(((S)-1-(((S)-4-methyl-1-((R)-2-methyloxiran-2-yl)-1-oxopentan-2-yl)amino)-1-oxo-3-phenylpropan-2-yl)amino)-1-oxobutan-2-yl)-4-phenylbutanamide

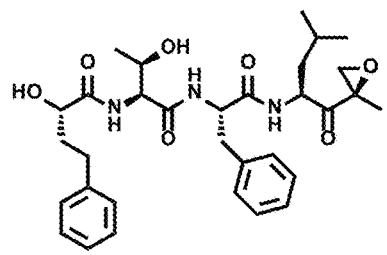

(2S)-2-(2-(3-(dimethylamino)propoxy)-4-phenylbutanamido)-4-methyl-N-((S)-1-(((S)-4-methyl-1-((R)-2-methyloxiran-2-yl)-1-oxopentan-2-yl)amino)-1-oxo-3-phenylpropan-2-yl)pentanamide

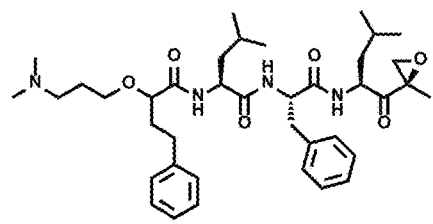

1-(((S)-3-methoxy-1-(((S)-1-(((S)-4-methyl-1-((R)-2-methyloxiran-2-yl)-1-oxopentan-2-yl)amino)-1-oxo-3-phenylpropan-2-yl)amino)-1-oxopropan-2-yl)amino)-1-oxo-4-phenylbutan-2-yl methylcarbamate

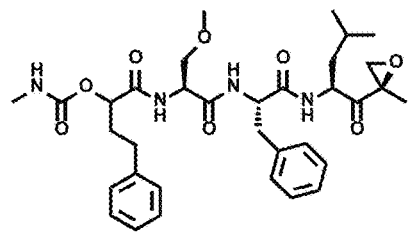

FIG. 1C *continued*

(2S)-2-(2-(hydroxymethyl)-4-phenylbutanamido)-4-methyl-N-((S)-1-(((S)-4-methyl-1-((R)-2-methyloxiran-2-yl)-1-oxopentan-2-yl)amino)-1-oxo-3-phenylpropan-2-yl)pentanamide

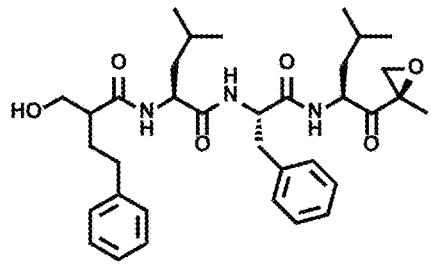

(2S)-2-(2-(2-(2-(dimethylamino)ethoxy)ethoxy)-4-phenylbutanamido)-4-methyl-N-((S)-1-(((S)-4-methyl-1-((R)-2-methyloxiran-2-yl)-1-oxopentan-2-yl)amino)-1-oxo-3-phenylpropan-2-yl)pentanamide

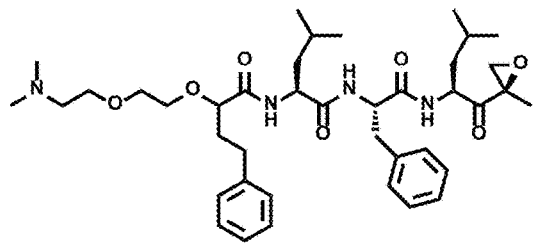

(S)-N-((2S,3S)-3-hydroxy-1-(((S)-4-methyl-1-((R)-2-methyloxiran-2-yl)-1-oxopentan-2-yl)amino)-1-oxobutan-2-yl)-2-((S)-2-hydroxy-4-phenylbutanamido)-4-methylpentanamide

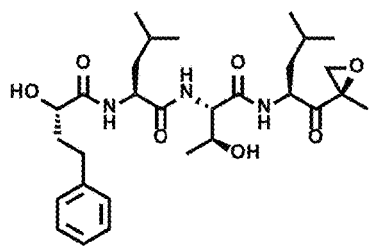

(S)-N-((S)-3-cyclopropyl-1-(((S)-4-methyl-1-((R)-2-methyloxiran-2-yl)-1-oxopentan-2-yl)amino)-1-oxopropan-2-yl)-2-((S)-2-hydroxy-4-phenylbutanamido)-4-methylpentanamide

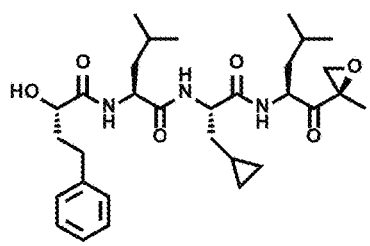

*Other exemplary proteasome inhibitors for treating senescence related disease* bortezomib bortezomib mannitol delanzomib ixazomib citrate ixazomib

MG132 carfilzomib oprozomib marizomib

ONX-0914

FIG. 2A

| Sample code | irradiated IMR90 EC$_{50}$ µM | IMR90 HD NSc EC$_{50}$ µM | Biochemical 20S β5c IC$_{50}$ nM |
|---|---|---|---|
| AF501 | 0.301 | 1.089 | |
| AF502 | 0.244 | 0.323 | 5.2 |
| AF503 | 0.241 | 0.719 | 1.4 |
| AF504 | 0.087 | 0.143 | 5.9 |
| AF505 | 2.013 | 4.208 | >1,000 |
| AF506 | 0.935 | 1.621 | 10.6 |
| AF507 | 0.226 | 0.521 | 2.7 |
| AF508 | 0.038 | 0.011 | |
| AF509 | 0.019 | 0.014 | |
| AF510 | 0.055 | 0.019 | |
| AF511 | 0.621 | 0.500 | |
| AF512 | 0.600 | NA | |
| AF513 | 0.183 | 1.697 | |
| AF514 | 0.067 | 0.110 | |
| AF515 | 1.185 | 0.049 | |
| AF516 | 0.396 | 0.068 | |
| AF517 | 0.221 | 0.470 | |
| AF518 | 0.027 | 0.246 | 8.1, 15 |
| AF519 | >50 | >50 | 150 |
| AF520 | >50 | >50 | 442 |
| AF521 | 0.240 | 1.116 | 2.1 |
| AF522 | 0.059 | 0.348 | 4.8 |
| AF523 | 0.237 | 0.482 | 7.4 |
| AF524 | 0.378 | >50 | 102 |

FIG. 2B

| Sample code | Composition | Binding activity 20S β5c IC$_{50}$ nM | Senolytic activity irradiated hSLF EC$_{50}$ μM |
|---|---|---|---|
| AM601 | C$_{34}$H$_{47}$N$_3$O$_6$ | 8.1, 15 | 0.1717 |
| AM602 | C$_{36}$H$_{49}$N$_3$O$_7$ | | 7.7 |
| AM603 | C$_{40}$H$_{56}$N$_4$O$_8$ | 2.7 | 0.299 |
| AM604 | C$_{41}$H$_{61}$N$_3$O$_8$S | 2.1 | 0.921 |
| AM605 | C$_{35}$H$_{49}$N$_3$O$_6$ | 14.1 | |
| AM606 | C$_{28}$H$_{43}$N$_3$O$_6$ | 73.5 | 0.193 |
| AM607 | C$_{32}$H$_{43}$N$_3$O$_7$ | 19 | 0.1216 |
| AM608 | C$_{39}$H$_{57}$N$_3$O$_9$S | 8.92 | 1.23 |
| AM609 | C$_{29}$H$_{45}$N$_3$O$_6$ | 38.1 | 0.1861 |
| AM610 | C$_{30}$H$_{45}$N$_3$O$_6$ | 89.3 | |
| AM611 | C$_{27}$H$_{41}$N$_3$O$_8$ | 69.4, 33.6 | 0.238 |
| AM612 | C$_{39}$H$_{57}$N$_4$O$_7$ | 130 | |
| AM613 | C$_{38}$H$_{56}$N$_4$O$_6$ | 481 | |
| AM614 | C$_{35}$H$_{59}$N$_3$O$_9$S | 3.86 | |
| AM615 | C$_{34}$H$_{55}$N$_3$O$_{10}$S | 11.7 | 0.3868 |
| AM616 | C$_{38}$H$_{56}$N$_4$O$_5$S | 166 | |
| AM617 | C$_{39}$H$_{58}$N$_4$O$_5$S | 60.1 | |
| AM618 | C$_{36}$H$_{50}$N$_4$O$_7$ | 3.56 | 0.588 |
| AM619 | C$_{29}$H$_{45}$N$_3$O$_7$ | 15 | 0.416 |
| AM620 | C$_{32}$H$_{43}$N$_3$O$_7$ | 32.7 | 0.224 |
| AM621 | C$_{39}$H$_{58}$N$_4$O$_6$ | 274.0 | |
| AM622 | C$_{34}$H$_{46}$N$_4$O$_8$ | 6.1 | 0.417 |
| AM623 | C$_{35}$H$_{49}$N$_3$O$_6$ | 4.65 | |
| AM624 | C$_{40}$H$_{50}$N$_4$O$_7$ | 88.3 | |
| AM625 | C$_{29}$H$_{45}$N$_3$O$_7$ | 13.9 | |
| AM626 | C$_{31}$G$_{47}$N$_3$O$_6$ | 17.5 | |

FIG. 2C

| Sample code | biochemistry proteasome 20S β5c IC50 nM | irradiated human SLF (synovial like fibroblasts) EC$_{50}$ µM (senolysis assay) | irradiated HUVEC (human umbilical vein cells) EC$_{50}$ µM (senolysis assay) |
|---|---|---|---|
| AB0953 | 11.55 | 0.172 | |
| AB0967 | | 7.7 | |
| AB0995 | 2.7 | 0.299 | |
| AB1009 | 2.1 | 0.921 | |
| AB1062 | 14.1 | | |
| AB1307 | 73.5 | 0.193 | |
| AB1338 | 19 | 0.122 | |
| AB1356 | 8.92 | 1.23 | |
| AB1357 | 38.1 | 0.186 | |
| AB1361 | 89.3 | | |
| AB1362 | 51.5 | 0.238 | |
| AB1367 | 130 | | |
| AB1368 | 481 | | |
| AB1369 | 3.86 | | |
| AB1371 | 11.7 | 0.387 | |
| AB1372 | 166 | | |
| AB1723 | 60.1 | | |
| AB1743 | 3.56 | 0.588 | |
| AB1759 | 15 | 0.416 | |
| AB1774 | 32.7 | 0.224 | |
| AB1772 | 274.0 | | |
| AB1775 | 6.1 | 0.417 | |

FIG. 2C continued

| Sample code | biochemistry proteasome 20S β5c IC50 nM | irradiated human SLF (synovial like fibroblasts) EC$_{50}$ µM (senolysis assay) | irradiated HUVEC (human umbilical vein cells) EC$_{50}$ µM (senolysis assay) |
|---|---|---|---|
| AB1795 | 4.65 | | |
| AB1796 | 88.3 | | |
| AB1797 | 13.9 | | |
| AB1813 | 17.5 | | |
| AB1024 | 2.8 | 1.923 | |
| AB1063 | 186 | | |
| AB1377 | 9.62 | 0.072 | 0.084 |
| AB1732 | >1000 | | 1.045 |
| AB1821 | 16.4 | | |
| AB1851 | 64.7 | | |
| AB1853 | 84.7 | | |
| AB1854 | 92.5 | | |
| AB1855 | 15.1 | | |
| AB1871 | 76.6 | | |
| AB1885 | 94.5 | | |

No surgery

*Intact* proteoglycan layers

OA surgery

*Destruction* of proteoglycan layers

OA surgery + Nutlin-3a

*Intact* proteoglycan layers

PEPTIDE-BASED PROTEASOME INHIBITORS FOR TREATING CONDITIONS MEDIATED BY SENESCENT CELLS AND FOR TREATING CANCER

PRIORITY

This application is a continuation-in-part of international application PCT/US2018/068190, filed Dec. 31, 2018, which claims the priority benefit of U.S. provisional patent applications 62/612,411, 62/612,414, 62/612,416, 62/612,417, and 62/612,418, all filed Dec. 30, 2017, provisional application 62/676,692, filed May 25, 2018, and international application PCT/US2018/068003, filed Dec. 28, 2018. The aforelisted applications are all hereby incorporated herein by reference in their entirety for all purposes.

FIELD OF THE INVENTION

The technology disclosed and claimed below relates generally to the activity of proteasomes and their inhibition in target cells. In particular, this disclosure provides a new family of proteasome inhibitors that are suited for use in treating conditions meditated by senescent cells and for treating cancer.

BACKGROUND

Senescent cells are characterized as cells that no longer have replicative capacity, but remain in the tissue of origin, eliciting a senescence-associated secretory phenotype (SASP). It is a premise of this disclosure that many age-related conditions are mediated by senescent cells, and that selective removal of the cells from tissues at or around the condition can be used clinically for the treatment of such conditions.

US 2016/0339019 A1 (Laberge et al.) describes treatment of certain age-related conditions using MDM2 inhibitors, Bcl inhibitors, and Akt inhibitors. US 20170266211 A1 (David et al.) describes the use of particular Bcl inhibitors for treatment of age-related conditions. U.S. Pat. Nos. 8,691,184, 9,096,625, and 9,403,856 (Wang et al.) describe Bcl inhibitors in a small-molecule library.

Other disclosures related to the role of senescent cells in human disease include the pre-grant publications US 2017/0056421 A1 (Zhou et al.), WO 2016/185481 (Yeda Inst.), US 2017/0216286 A1 (Kirkland et al.), and US 2017/0281649 A1 (David); and the articles by Furhmann-Stroissnigg et al. (Nat Commun. 2017 Sep. 4; 8(1):422), Blagosklonny (Cancer Biol Ther. 2013 December; 14(12):1092-7), and Zhu et al. (Aging Cell. 2015 August; 14(4):644-58).

In a previously unrelated field, the targeting of proteasome complexes to treat cancer and other conditions is referred to in Park et al., Transl Res. 2018 August; 198:1-16, and in Dou et al., Curr Cancer Drug Targets. 2014; 14(6): 517-36. Proteasome inhibitor patents since 2010 are reviewed by Metcalf et al., Expert Opin Ther Pat. 2014 April; 24(4):369-8.

SUMMARY

The new proteasome inhibitors described below are peptide-based compounds with a short linear sequence of amino acids. An oxo or thio group is attached to the N-terminal amino acid. A protein-reactive electrophilic group such as an epoxyketone, an aziridinylketones, or a beta-lactone is attached to the C-terminal amino acid. Upon contact with a proteasome complex in a target cell, the electrophilic group reacts with a functional group in or near a binding pocket or active site of the proteasome, forming a covalent bond and thereby inactivating the proteasome.

Certain biochemical pathways are more active in senescent cells than in other cell types. Previous medicines for treating senescent conditions have been based on inhibitors of the Bcl protein family, or MDM2. This disclosure is based in part on the discovery that the proteasome pathway is also selectively expressed in senescent cells. This provides a window of opportunity for targeting senescent cells without unduly impairing the activity of neighboring non-senescent cells in the target tissue. Contacting senescent cells in vitro or in vivo with small-molecule senolytic agents selectively modulates or eliminates such cells. The inhibitors can be used for administration to a target tissue in a subject, thereby selectively eliminating senescent cells in or around the tissue, and relieving one or more symptoms or signs of disease or aging that are initiated or mediated by the senescent cells.

The new proteasome inhibitors described below, and proteasome inhibitors having other structures can be screened for binding affinity and an ability to eliminate senescent cells or cancer cells selectively. Compounds with the requisite activity can be developed for the treatment of conditions such as osteoarthritis, ophthalmic disease, pulmonary disease, and atherosclerosis.

The invention is put forth in the description that follows, in the drawings, and in the appended claims.

DRAWINGS

FIGS. 1A, 1B, and 1C show structures of exemplary proteasome inhibitors according to this invention. FIG. 1D shows previously known proteasome inhibitors that can be newly applied to the treatment of senescent disease.

FIGS. 2A, 2B, and 2C show results from a screening assay to identify compounds that selectively kill senescent cells, leaving non-senescent cells intact. FIG. 2A provides data for senolytic activity and proteasome binding for structures selected from FIGS. 1A and 1C. FIG. 2B provides data for senolytic activity and proteasome binding for structures selected from FIG. 1B.

FIGS. 3A, 3B, and 3C show expression of senescent cell markers p16, IL-6, and MMP13 respectively in an osteoarthritis model. FIG. 4A shows that an effective senolytic agent restores symmetrical weight bearing to treated mice in the osteoarthritis model. FIGS. 4B, 4C, and 4D are images showing histopathology of the joints in these mice. The test senolytic agent helps prevent or reverses destruction of the proteoglycan layer.

FIG. 4A shows that an effective senolytic agent restores symmetrical weight bearing to treated mice in the osteoarthritis model. FIGS. 4B, 4C, and 4D are images showing histopathology of the joints in these mice. The test senolytic agent helps prevent or reverses destruction of the proteoglycan layer.

Figure 7:
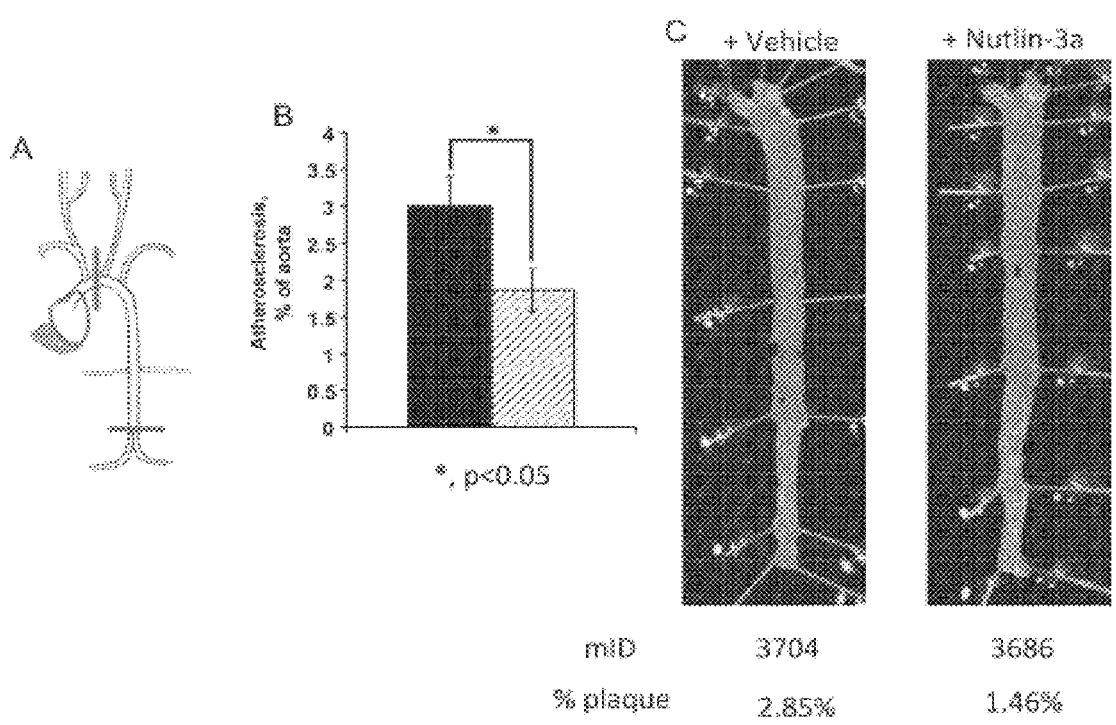

FIG. 7 shows data taken from a mouse model for atherosclerosis, in which inbred mice lacking the LDL receptor were fed a high-fat diet. The right panel shows staining for plaques in the aorta. The middle panel shows quantitatively that the surface area of the aorta covered with plaques was reduced by treatment with a senolytic agent.

Figure 8:
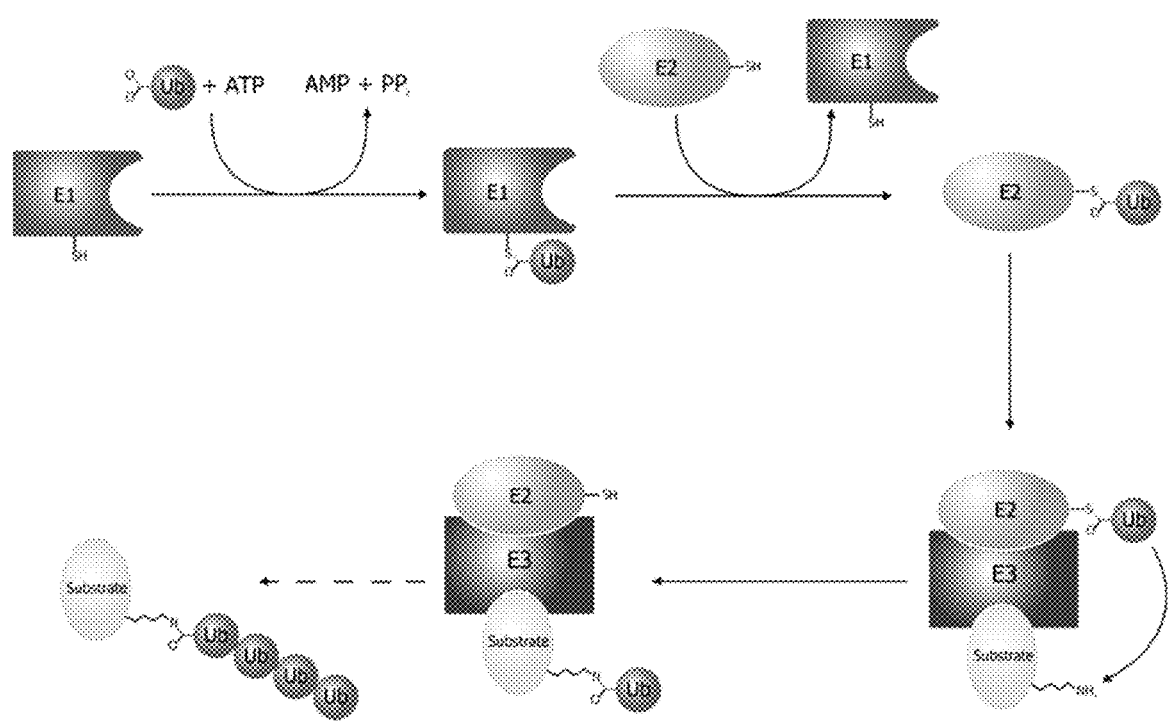

FIG. 8 is a schematic portrayal of the proteasome pathway and its role in the destruction of proteins marked by ubiquitination.

DETAILED DESCRIPTION

Senescent cell medicine encompasses the paradigm that many conditions that are associated with aging or tissue damage are caused or mediated by senescent cells. These are cells that no longer replicate, but have a secretory phenotype that includes secretion of factors that trigger pathophysiology.

This disclosure shows that the proteasome pathway is active in senescent cells, and can be used as an effective means for removing senescent cells from a target tissue, as an alternative to other targets. A new family of proteasome inhibitors are provided as part of the invention.

Proteasome Function

The proteasome is a protein complex consisting of 28 subunits arranged in four stacked rings, each having 7 subunits (two outer α1-7-rings and two inner β1-7-rings). The catalytic protease activity derives from 3 of the β subunits. The chymotrypsin-like (CT-L) activity (β5), trypsin-like (T-L) activity (β2), and caspase-like or post-acid (PA) activity (β1).

FIG. 8 provides a schematic depiction of the role of proteasomes in cells. The proteasome is the effector component of the ubiquitin-proteasome-system (UPS) where it degrades ubiquitinated proteins by proteolysis. Ubiquitination is a post-translation modification where the ubiquitin protein is covalently attached to lysine residues. A series of enzymes carries out a cascade of reactions involving E1 activating, E2 conjugating and E3 ligating enzymes. Ubiquitin itself contains lysine residues which can serve to propagate the cycle of ubiquitination with the addition of more ubiquitin units. Ubiquitination at K48 and K11 mark proteins for degradation by the proteasome. These ubiquitinated proteins marked for degradation consist of components of signaling pathways and misfolded or damaged proteins.

The UPS pathway is important for replenishing cells with amino acids required for survival. Reduced levels of proteasome have been observed in senescent cells with corresponding increases in levels of both damaged (oxidized) and ubiquitinated proteins. Several proteins involved in survival and apoptotic pathways are regulated via the UPS system. Senescent cells have a dysregulated survival/apoptosis balance, proteasome inhibition is proposed to be senolytic.

New Proteasome Inhibitors

Figure 1A:
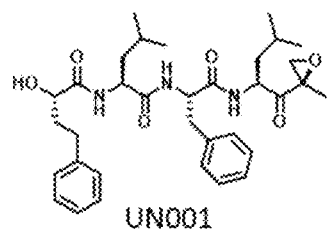
Figure 1A:
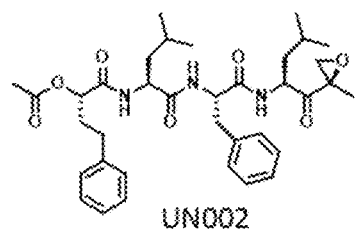
Figure 1A:
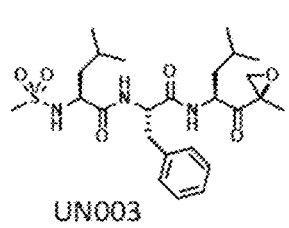
Figure 1A:
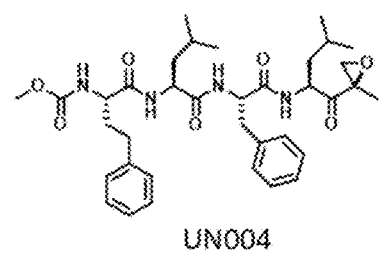
Figure 1A:
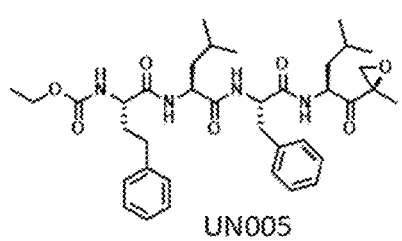
Figure 1A:
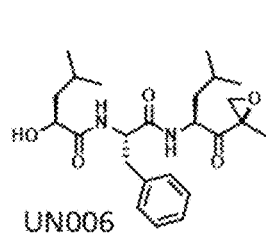
Figure 1A:
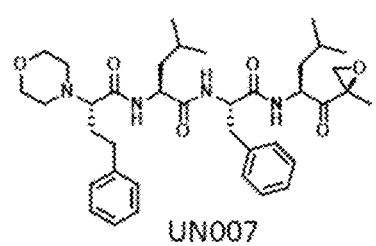
Figure 1A:
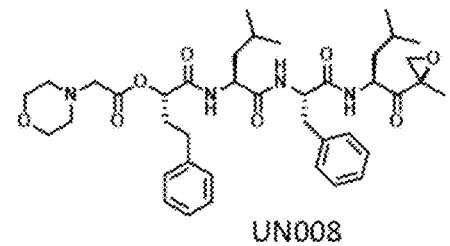
Figure 1A:
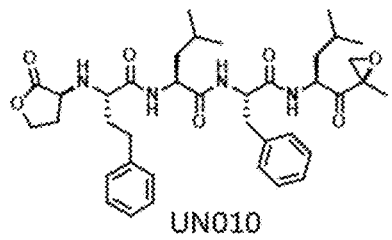
Figure 1A:
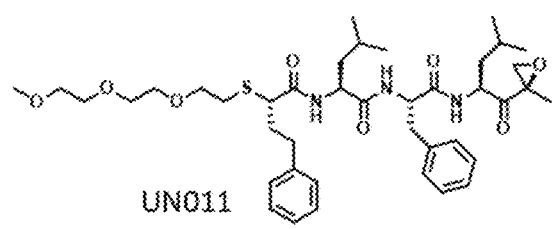
Figure 1A:
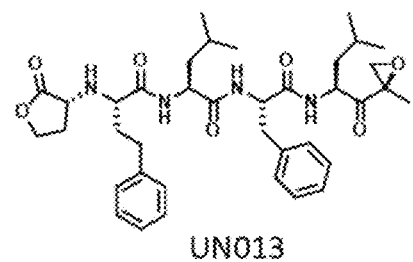
Figure 1A:
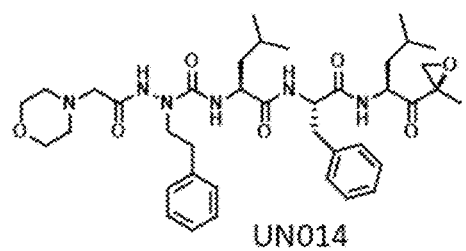
Figure 1B:
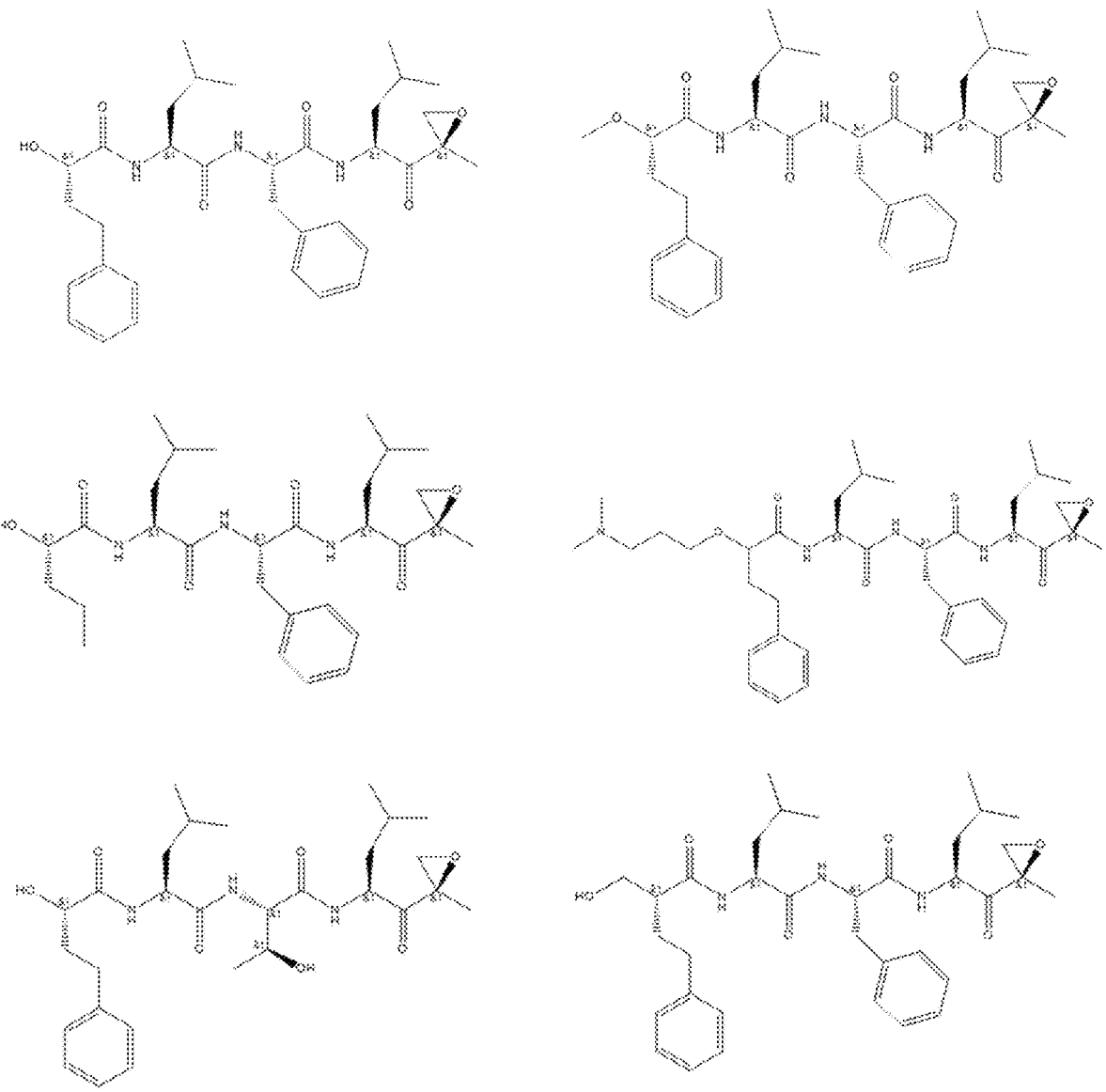
Figure 1B:
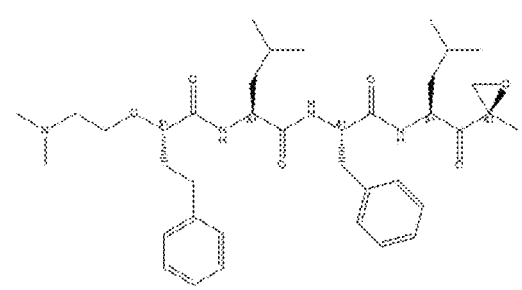
Figure 1B:
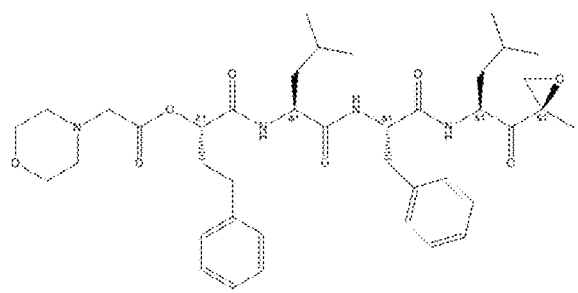
Figure 1B:
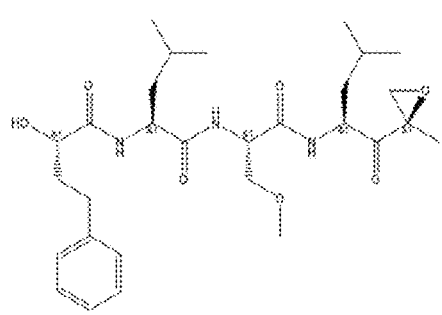
Figure 1B:
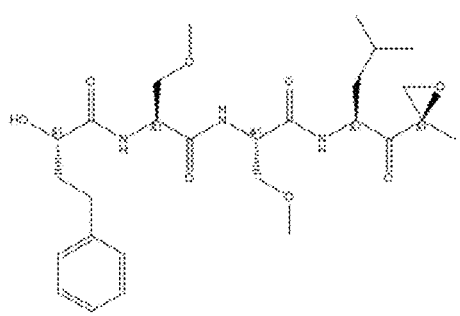
Figure 1B:
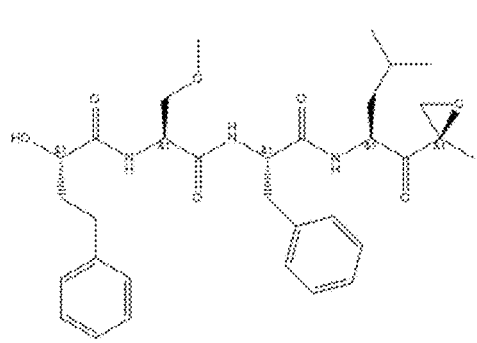
Figure 1B:
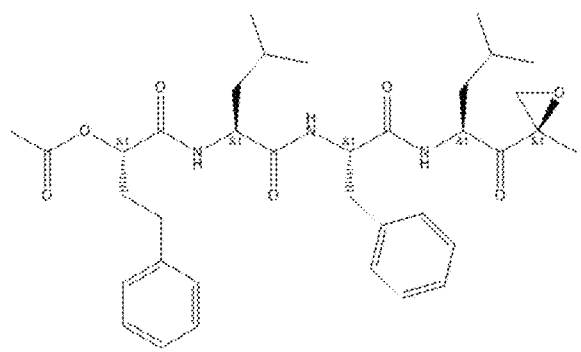

FIGS. 1A, 1B, and 1C depict a family of small molecule compounds that were synthesized for the first time as illustrations of this invention. These compounds and their analogs are designed for inhibiting proteasome activity, and are suitable for testing and development for the purpose of eliminating senescent cells or treating senescence-associated conditions. They can also be used for the purpose of eliminating cancerous or malignant cells in the treatment of cancer.

Proteasome inhibitors included in this invention are peptidic compounds having a plurality of (typically 3 to 7) peptidic units arranged in a sequence, where the first unit of the sequence has an oxo or thio group at a first terminal and the last unit in the sequence has an electrophilic group at a second terminal. The peptidic units of the proteasome inhibitors of this disclosure can include an amino acid residue or a peptidomimetic unit that mimics the residue, or a component of the residue. When the peptidic compounds are composed of amino acid residues, the amino group of the N-terminal residue is replaced with an oxo or thio group and the C-terminal residue is modified to include an electrophilic group.

An exemplary proteasome inhibitor has the structure shown in Formula (I):

$$R^0\text{—}X\text{-}(A)_n\text{-}Z \tag{I}$$

where;
$R^0$ is selected from H, alkyl, substituted alkyl, alkanoyl, substituted alkanoyl, alkylaminocarbonyl, substituted alkylaminocarbonyl, alkoxycarbonyl, substituted alkoxycarbonyl, alkylaminothiocarbonyl, substituted alkylaminothiocarbonyl, alkoxythiocarbonyl, substituted alkoxythiocarbonyl and promoiety;
$(A)_n$ is a sequence of n peptidic units $A^1$ to $A^n$, each independently selected from amino acid residues and peptidomimetic units, where:
n is 2-7;
the $A^1$ unit includes a first terminal group X, wherein X is O (i.e., oxo) or S (i.e., thio); and
the $A^n$ unit includes a second terminal group Z that is a proteasome-reactive electrophilic group.

When n is 4, the proteasome inhibitors of this disclosure may conform to the structure shown in Formula (Ia):

$$R^0\text{—}X\text{-}A^1\text{-}A^2\text{-}A^3\text{-}A^4\text{-}Z \tag{Ia}$$

where the $A_4$ unit includes a modified terminal Z. The term modified terminal Z refers to a unit of the proteasome inhibitor that can be an amino acid residue or peptidomimetic residue where a C-terminal carboxylic acid group that is found in a naturally occurring peptide is replaced with proteasome-reactive electrophilic group Z.

Amino acid residues of the proteasome inhibitors of this disclosure can be α-amino acids or β-amino acids, where the amino acids in this context can be naturally or non-naturally occurring, L-amino acids or D-amino acids. Peptidomimetic units in this context can include small organic group designed to mimic an amino acid residue or a dipeptide residue, or a fragment or smaller component of such residues (e.g., a peptide bond). The peptidomimetic unit can be referred to as a bioisostere of an amino acid or dipeptide residue or component thereof. An example of such a component is an amide bond bioisostere. Amide bond bioisosteres include groups such as ester, ethylene, thioamide, alkylamino, alkylketone, alkylether, N-alkyl-amide, tetrazole and pyrrole. Peptidomimetic units which can be utilized as bioisosteres in the inhibitors of this disclosure include hydroxyethylamine, hydroxyethylene, 1,2-dihydroxyethylene, hydroxyamide, a-ketoamide, amino ketone and statin dipeptide isosteres, and azapeptide, peptoid and retroinverso units. Other bioisosteres of α-amino acid residues include quinoxaline-2,4(1H)-dione, quinoxaline-2,3(1H)-dione and quinolin-2(1H)-one, azagrevellin, 3,4-diamino-3-cyclobutene-1,2-dione, and azepine-derived structures. In the proteasome inhibitors of this disclosure, one or more units of the sequence is a peptidomimetic unit. The $A^1$ unit of formula (I)-(Ia) can be referred to as a peptidomimetic unit because it includes an oxo (i.e., X=O) or thio (i.e., X=S) group instead of a N-terminal amine group of an amino acid residue. The $A^4$ unit of formula (Ia) can be referred to as a peptidomimetic unit because it includes a terminal group Z instead of a C-terminal carboxylic acid of a naturally occurring amino acid residue.

The proteasome inhibitors of this disclosure may also conform to the structure shown in Formula (II):

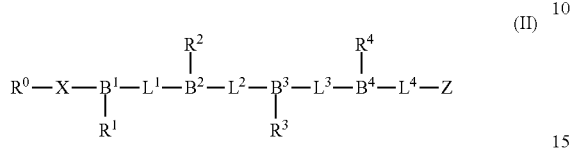
(II)

where:
- $B^1$ to $B^4$ are each independently a branching group selected from CH, CR" and N, wherein R" is $C_{(1-6)}$alkyl or substituted $C_{(1-6)}$alkyl;
- $L^1$ to $L^4$ are each independently a linking group; and
- $R^1$ to $R^4$ are independently selected from alkyl, substituted alkyl, aralkyl, substituted aralkyl, heteroarylalkyl and substituted heteroarylalkyl.

The sequence of branching and linking groups shown in Formula (II) can provide a peptidic backbone for the proteasome inhibitors of this disclosure to which amino acid sidechain groups of interest $R^1$ to $R^4$ can be connected in a desirable configuration. The branching groups $B^1$ to $B^4$ of the peptidic backbone can be trivalent groups which link the sidechain groups to the peptidic backbone of the compound.

The linking groups $L^1$ to $L^4$ can be groups having a backbone of 1 to 3 atoms (e.g., 2 or 3 atoms) that connect adjacent branching groups, e.g., $B^1$ and $B^2$. A linking group in this context can be an amide bond or amide bond bioisostere. A variety of $L^1$ to $L^4$ can be selected from —CONR'—, —CH$_2$NR'—, CH(OH)NR'—, —CH$_2$CONR'—, —CO—, —CH$_2$CO—, —COCH$_2$—, —CO$_2$—, —CH$_2$O—, —CH$_2$S—, —CH$_2$CH$_2$—, —CH=CH— and —NR'CO—, wherein R' is H, $C_{(1-6)}$alkyl or substituted $C_{(1-6)}$alkyl (e.g., methyl).

It is understood that together the sequence of branching and linking groups —B"-L"-represented in the structure of Formula (II) provide a peptidic backbone for inhibitors of this disclosure, but that each individual —B"-L"- unit in the structure as defined need not necessarily correspond directly to, or align exactly with, a single peptidic unit (A) of a parent peptidic sequence, e.g., sequence (A)$_n$ of formula (I). As such, one or more of the —B"(R")-L"- groups of formula (II), can be selected from the following structures, where R" refers to a sidechain group, e.g., one of $R^1$ to $R^4$:

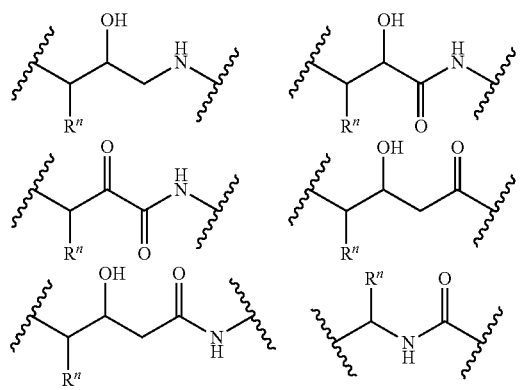

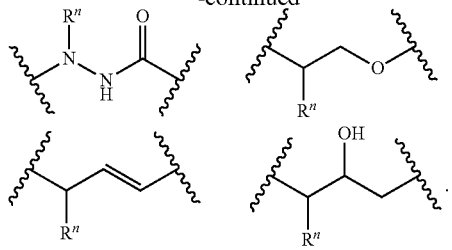

The proteasome inhibitors of this disclosure may also conform to one of the structures shown in Formulas (IIIa) to (IIIc):

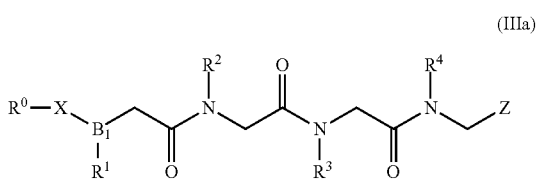
(IIIa)

(IIIb)

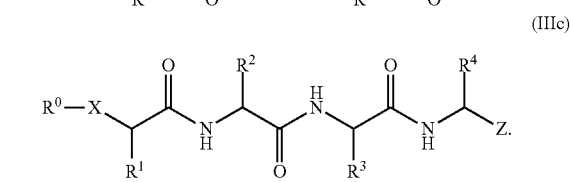
(IIIc)

Formula (IIIa) is an exemplary proteasome inhibitor of formula (II) that includes peptoid units (e.g., —NR$^2$CH$_2$CO— monomer units). Formula (IIIa) is an exemplary proteasome inhibitor of formula (II) that includes retroinverso peptidic units, e.g., α-amino acid units configured in a reverse sequence as compared to the sequence of α-amino acid units of Formula (IIIc). Formula (IIIc) is an exemplary proteasome inhibitor of formula (II) that includes α-amino acid residues and has modified N- and C-terminals.

Exemplary is a compound having the structure shown in Formula (Ib):

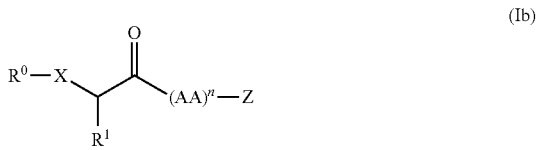
(Ib)

where:
X is O or S;
$R^0$ is selected from H, alkyl, substituted alkyl, alkanoyl, substituted alkanoyl, alkylaminocarbonyl, substituted alkylaminocarbonyl, alkoxycarbonyl, substituted alkoxycarbonyl, alkylaminothiocarbonyl, substituted alkylaminothiocarbonyl, alkoxythiocarbonyl, substituted alkoxythiocarbonyl and promoiety;

$R^1$ is selected from alkyl, substituted alkyl, aralkyl, substituted aralkyl, heteroarylalkyl and substituted heteroarylalkyl;

$(AA)_n$ is a sequence of 2 to 7 independently selected amino acid residues, wherein the C-terminal residue of $(AA)_n$ comprises a modified C-terminal comprising Z; and Z is a proteasome-reactive electrophilic group.

When n is 4 in Formula (Ib), proteasome inhibitors of this disclosure may also conform to the structure shown in Formula (IIIc)

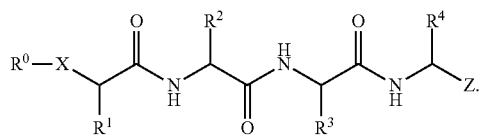

(IIIc)

When used in this context, the term "amino acid" refers either to a naturally occurring or non-naturally occurring amino acid, either in the L- or the D-configuration. For equivalents of the invention, one or more of the amino acids in the sequence $(AA)_n$ may be substituted with an amino acid analog (peptidomimetic unit) linked to the rest of the structure by way of a covalent bond that is not a peptide bond, wherein the analog has reactive properties and conformation that are substantially the same as the corresponding amino acid.

A "proteasome-reactive electrophilic group" that is part of a proteasome inhibitor exemplified in this invention is defined as an electrophilic moiety that upon contact with a target proteasome, reacts with a functional group (a nucleophilic sidechain on an amino acid residue) near a binding pocket or active site of the proteasome, thereby forming a covalent bond and inhibiting the proteasome from performing its biological function. Electrophilic groups that are protein reactive include epoxides, Michael acceptors, disulfides, lactones, b-lactams, and quinones, as taught for example in J. Krysiak and R. Breinbauer, Top Curr Chem (2012) 324: 43-84. See also Chapter 5, pages 207-265 in "The organic chemistry of drug design and drug action" by Silverman and Holladay, Third Ed. Academic Press, 2014. For example, reactive electrophilic groups that may be used in the proteasome inhibitors include 2-chloro-acetyl (—COCH$_2$Cl), vinyl sulfone (—SO$_2$CH=CH$_2$), acetylene, or methyl-acetylene (i.e., cysteine-reactive groups).

The invention includes compounds according to Formula (I) where Z is selected from epoxyketone group, aziridinylketone group, boronate, boronate ester and beta-lactone. The invention includes compounds of Formula (I) where $(AA)_n$ is a sequence of three independently selected amino acid residues, wherein the C-terminal residue of $(AA)_n$ is modified to include Z. By modified to include Z can include modifying the C-terminal carboxylic acid to a ketone, such as epoxyketone or aziridinylketone, or replacing the C-terminal carboxylic acid with a boronate or boronate ester. Any convenient synthetic methods can be utilized in modifying an amino acid building block to incorporate the proteasome-reactive electrophilic group.

The proteasome inhibitors may also conform to the structure shown in Formula (IV):

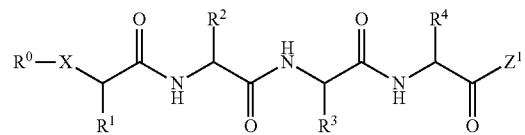

(IV)

where:
$R^2$ to $R^4$ are independently selected from alkyl, substituted alkyl, aralkyl, substituted aralkyl, heteroarylalkyl and substituted heteroarylalkyl; and
$Z^1$ is epoxide group or aziridine group.

The proteasome inhibitor compounds of Formula (IV) include compounds of Formula (V):

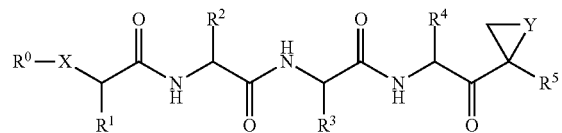

(V)

where Y is selected from O and NR$^{15}$; and $R^5$ and $R^{15}$ are independently selected from H, $C_{(1-6)}$alkyl and substituted $C_{(1-6)}$alkyl.

The invention includes compounds of Formula (II) where $R^1$ to $R^4$ are independently selected from $C_{(1-6)}$alkyl, substituted $C_{(1-6)}$alkyl, $C_{(1-6)}$hydroxyalkyl, substituted $C_{(1-6)}$hydroxyalkyl, $C_{(1-6)}$alkoxy-$C_{(1-6)}$alkyl, substituted $C_{(1-6)}$alkoxy-$C_{(1-6)}$alkyl, aryl-$C_{(1-6)}$alkyl, substituted aryl-$C_{(1-6)}$alkyl, heteroaryl-$C_{(1-6)}$alkyl, substituted heteroaryl-$C_{(1-6)}$alkyl, cycloalkyl-$C_{(1-6)}$alkyl, substituted cycloalkyl-$C_{(1-6)}$alkyl, heterocycle-$C_{(1-6)}$alkyl and substituted heterocycle-$C_{(1-6)}$alkyl.

The proteasome inhibitor compounds can be further described by Formula (VI) or Formula (VII):

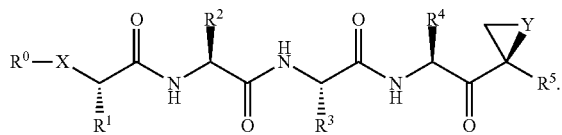

(VI)

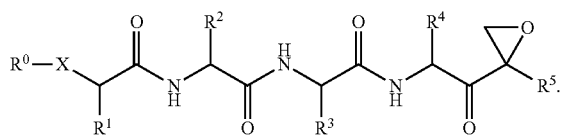

(VII)

In any of the aforelisted structures,
X can be O or S;
$R^0$ can be $R^{10}$— or $R^{10}$-Q-;
Q can be selected from ethylene glycol, polyethylene glycol, —C(=O)—, —NR11C(=O)—, —OC(=O)—, —C(=S)—, —NR11C(=S)—, —OC(=S)— and —OC(=S)—; and
$R^{10}$ and $R^{11}$ can be independently selected from H, alkyl and substituted alkyl.

In any of the aforelisted structures, $R^0$ may be selected from the following structures:

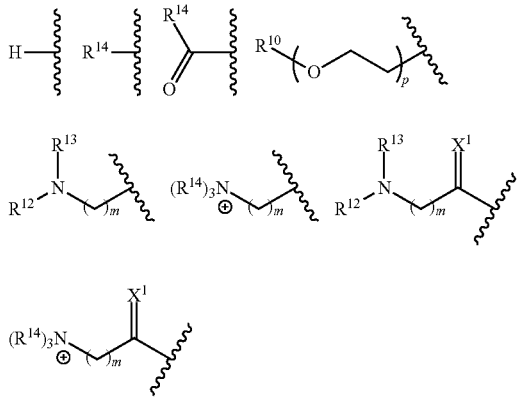

where:
m is an integer from 1 to 6;
p is an integer from 1 to 30;
X' is selected from O, S and $NR^{14}$; and
$R^{12}$ and $R^{13}$ are independently selected from H, alkyl and substituted alkyl, or $R^{12}$ and $R^{13}$ are cyclically linked and together with the nitrogen atom to which they are attached provide a heterocycle ring that is optionally further substituted; and
each $R^{14}$ is independently selected from H, $C_{(1-6)}$alkyl and substituted $C_{(1-6)}$alkyl.

In any of the aforelisted structures, $R^0$ may be selected from the following structures:

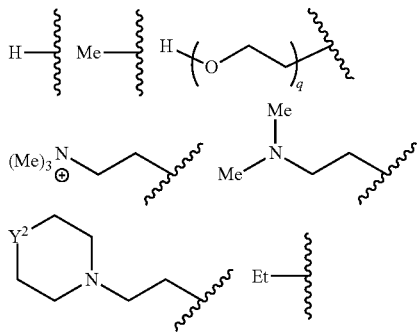

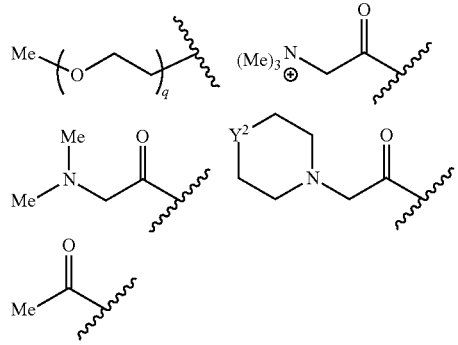

wherein:
q is an integer from 1 to 3;
$Y^2$ is selected from O and $NR^{15}$; and
$R^{15}$ is selected from H, $C_{(1-6)}$alkyl and substituted $C_{(1-6)}$alkyl.

In any of the aforelisted structures, $R^1$ can be selected from $C_{(1-6)}$alkyl, aryl-$C_{(1-6)}$alkyl, substituted aryl-$C_{(1-6)}$alkyl, cycloalkyl-$C_{(1-6)}$alkyl and substituted cycloalkyl-$C_{(1-6)}$alkyl. $R^2$ and $R^4$ can be selected from $C_{(1-6)}$alkyl, substituted $C_{(1-6)}$alkyl, $C_{(1-6)}$alkoxy-$C_{(1-6)}$alkyl, substituted $C_{(1-6)}$alkoxy-$C_{(1-6)}$alkyl, $C_{(1-6)}$hydroxyalkyl and substituted $C_{(1-6)}$hydroxyalkyl. In addition, $R^3$ can be selected from aryl-$C_{(1-6)}$alkyl, substituted aryl-$C_{(1-6)}$alkyl, $C_{(1-6)}$alkoxy-$C_{(1-6)}$alkyl and substituted $C_{(1-6)}$alkoxy-$C_{(1-6)}$alkyl.

In any of the aforelisted structures, $R^1$ can be selected from phenyl-$C_{(1-6)}$alkyl, cycloalkyl-$C_{(1-6)}$alkyl and $C_{(1-6)}$alkyl. $R^2$ can be selected from $C_{(1-6)}$alkoxy-$C_{(1-6)}$alkyl, $C_{(1-6)}$alkyl and $C_{(1-6)}$hydroxyalkyl. Sometimes, $R^3$ is selected from phenyl-$C_{(1-6)}$alkyl, cycloalkyl-$C_{(1-6)}$alkyl, $C_{(1-6)}$alkoxy-$C_{(1-6)}$alkyl and $C_{(1-6)}$hydroxyalkyl. In addition, $R^4$ can be $C_{(1-6)}$alkyl.

In any of the aforelisted structures, $R^1$ can be selected from phenylethyl, cyclopropyl-methyl and propyl. $R^2$ can be selected from methoxymethyl, isobutyl and 1-hydroxyethyl. Sometimes, $R^3$ is selected from phenylmethyl, cyclopropyl-methyl, methoxymethyl and 1-hydroxy-ethyl. In addition, $R^4$ can be isobutyl.

In any of the aforelisted structures, $R^1$ to $R^4$ can be selected from one of combinations #1-6 in the following table:

| # | $R^1$ | $R^2$ | $R^3$ | $R^4$ |
|---|---|---|---|---|
| 1 | phenyl-$C_{(1-6)}$alkyl, cycloalkyl-$C_{(1-6)}$alkyl or $C_{(1-6)}$alkyl | $CH_2CH(CH_3)_2$ | $CH_2Ph$ | $CH_2CH(CH_3)_2$ |
| 2 | $CH_2Ph$ | $C_{(1-6)}$alkoxy-$C_{(1-6)}$alkyl, $C_{(1-6)}$alkyl or $C_{(1-6)}$hydroxyalkyl | $CH_2Ph$ | $CH_2CH(CH_3)_2$ |
| 3 | $CH_2CH_2Ph$ | $CH_2CH(CH_3)_2$ | | $CH_2CH(CH_3)_2$ |
| 4 | $CH_2CH_2Ph$ | $CH_2CH(CH_3)_2$ | $CH_2Ph$ | $C_{(1-6)}$alkyl |
| 5 | $CH_2CH_2Ph$ | $C_{(1-6)}$alkoxy-$C_{(1-6)}$alkyl, $C_{(1-6)}$alkyl or $C_{(1-6)}$hydroxyalkyl | $CH_2Ph$ | $C_{(1-6)}$alkyl |
| 6 | $CH_2CH_2Ph$ | $CH_2CH(CH_3)_2$ | $CH_2Ph$ | $CH_2CH(CH_3)_2$ |

The invention includes proteasome inhibitor compounds according to Formulas (VIa) to (VId):

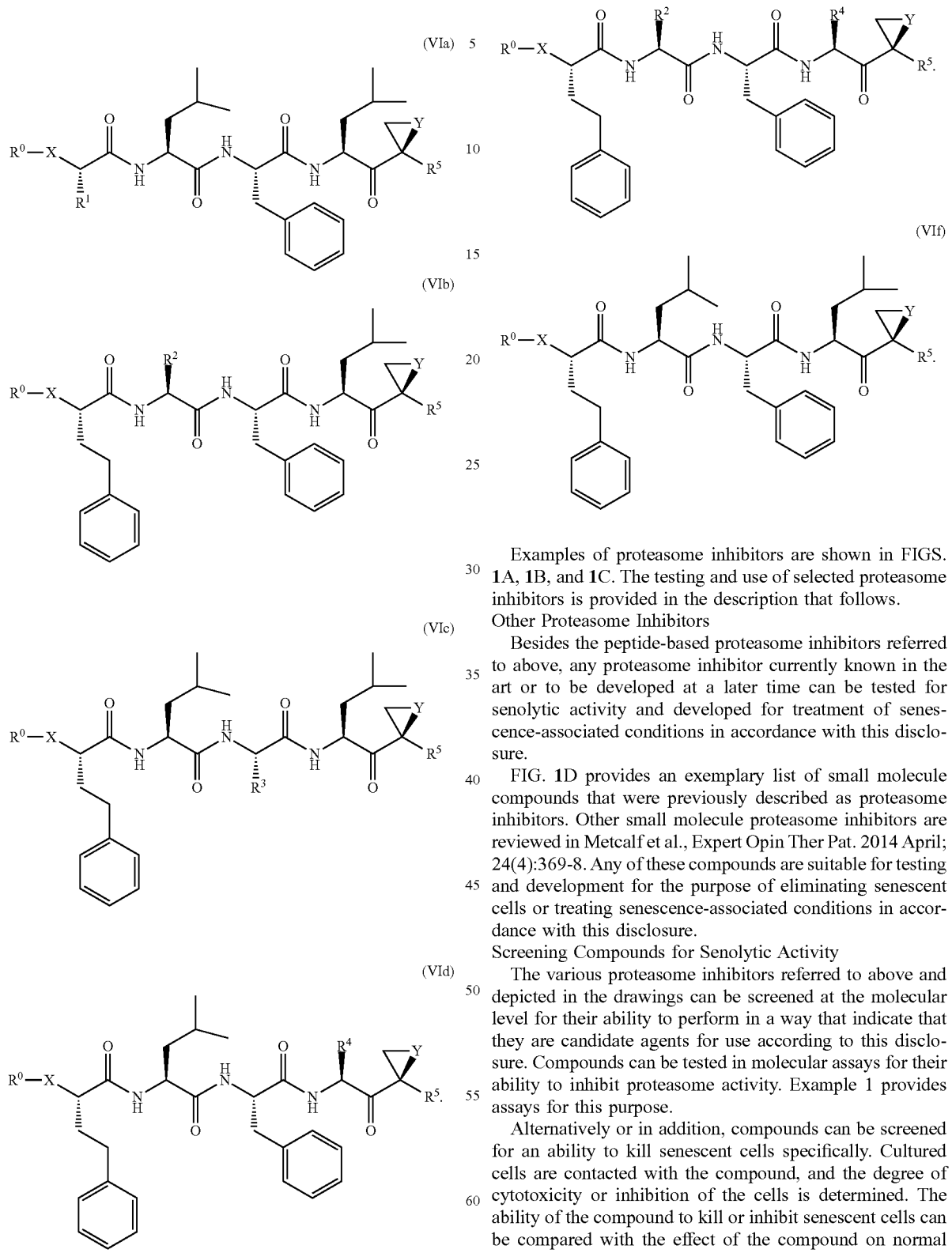

The proteasome inhibitor compounds include compounds according to Formula (VIe) and Formula (VIf). Optionally, Y can be O and $R^5$ can be methyl; X can be O or S.

Examples of proteasome inhibitors are shown in FIGS. 1A, 1B, and 1C. The testing and use of selected proteasome inhibitors is provided in the description that follows.

Other Proteasome Inhibitors

Besides the peptide-based proteasome inhibitors referred to above, any proteasome inhibitor currently known in the art or to be developed at a later time can be tested for senolytic activity and developed for treatment of senescence-associated conditions in accordance with this disclosure.

Figure 1D:
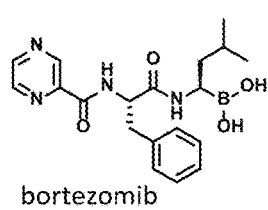
Figure 1D:
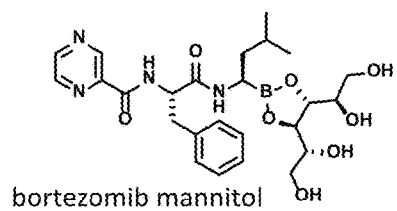
Figure 1D:
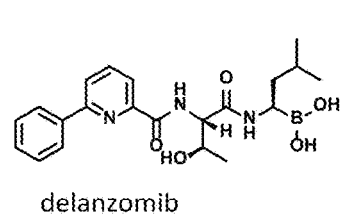
Figure 1D:
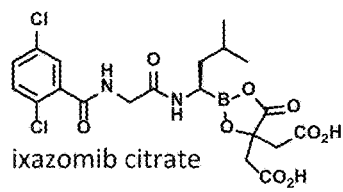
Figure 1D:
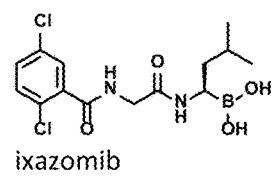
Figure 1D:
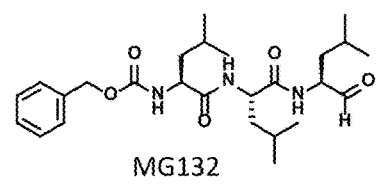
Figure 1D:
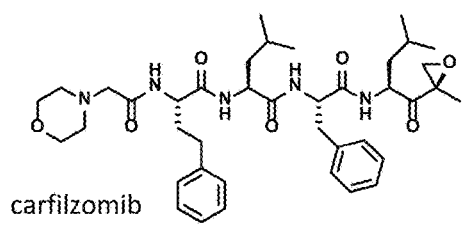
Figure 1D:
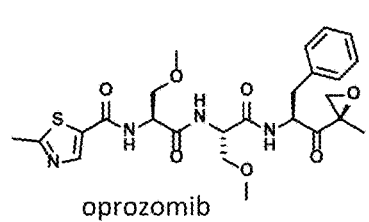
Figure 1D:
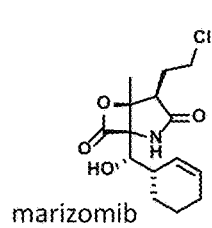
Figure 1D:
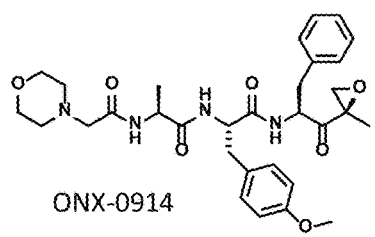

FIG. 1D provides an exemplary list of small molecule compounds that were previously described as proteasome inhibitors. Other small molecule proteasome inhibitors are reviewed in Metcalf et al., Expert Opin Ther Pat. 2014 April; 24(4):369-8. Any of these compounds are suitable for testing and development for the purpose of eliminating senescent cells or treating senescence-associated conditions in accordance with this disclosure.

Screening Compounds for Senolytic Activity

The various proteasome inhibitors referred to above and depicted in the drawings can be screened at the molecular level for their ability to perform in a way that indicate that they are candidate agents for use according to this disclosure. Compounds can be tested in molecular assays for their ability to inhibit proteasome activity. Example 1 provides assays for this purpose.

Alternatively or in addition, compounds can be screened for an ability to kill senescent cells specifically. Cultured cells are contacted with the compound, and the degree of cytotoxicity or inhibition of the cells is determined. The ability of the compound to kill or inhibit senescent cells can be compared with the effect of the compound on normal cells that are freely dividing at low density, and normal cells that are in a quiescent state at high density. Examples 2A and 2B provide illustrations of senescent cell killing using the human target tissue fibroblast IMR90 cell line and HUVEC cells. Similar protocols are known and can be developed or optimized for testing the ability of the cells to kill or inhibit other senescent cells and other cell types, such as cancer cells.

FIGS. 2A, 2B, and 2C show results from a screening assay to identify compounds that selectively kill senescent cells, leaving non-senescent cells intact. FIG. 2A provides data for senolytic activity and proteasome binding for structures selected from FIGS. 1A and 1D. FIG. 2B provides data for senolytic activity and proteasome binding for structures selected from FIG. 1B. FIG. 2C provides data for structures selected from FIG. 1C.

Candidate senolytic agents that are effective in selectively killing senescent cells in vitro can be further screened in animal models for particular disease. Examples 4, 5, 6, and 7 below provide illustrations for osteoarthritis, eye disease, lung disease, and atherosclerosis, respectively.

Medicament Formulation and Packaging

Preparation and formulation of pharmaceutical agents for use according to this disclosure can incorporate standard technology, as described, for example, in the current edition of *Remington: The Science and Practice of Pharmacy*. The formulation will typically be optimized for administration to the target tissue, for example, by local administration, in a manner that enhances access of the active agent to the target senolytic cells and providing the optimal duration of effect, while minimizing side effects or exposure to tissues that are not involved in the condition being treated.

This invention includes commercial products that are kits that enclose unit doses of one or more of the agents or compositions described in this disclosure. Such kits typically comprise a pharmaceutical preparation in one or more containers. The preparations may be provided as one or more unit doses (either combined or separate). The kit may contain a device such as a syringe for administration of the agent or composition in or around the target tissue of a subject in need thereof. The product may also contain or be accompanied by an informational package insert describing the use and attendant benefits of the drugs in treating the senescent cell associated condition, and optionally an appliance or device for delivery of the composition.

Treatment Design and Dosing Schedule

Senescent cells accumulate with age, which is why conditions mediated by senescent cells occur more frequently in older adults. In addition, different types of stress on pulmonary tissues may promote the emergence of senescent cells and the phenotype they express. Cell stressors include oxidative stress, metabolic stress, DNA damage (for example, as a result of environmental ultraviolet light exposure or genetic disorder), oncogene activation, and telomere shortening (resulting, for example, from hyperproliferation). Tissues that are subject to such stressors may have a higher prevalence of senescent cells, which in turn may lead to presentation of certain conditions at an earlier age, or in a more severe form. An inheritable susceptibility to certain conditions suggests that the accumulation of disease-mediating senescent cells may directly or indirectly be influenced by genetic components, which can lead to earlier presentation.

One of the benefits of the senescent cell paradigm is that successful removal of senescent cells may provide the subject with a long-term therapeutic effect. Senescent cells are essentially non-proliferative, which means that subsequent repopulation of a tissue with more senescent cells can only occur by conversion of non-senescent cells in the tissue to senescent cells—a process that takes considerably longer than simple proliferation. As a general principle, a period of therapy with a senolytic agent that is sufficient to remove senescent cells from a target tissue (a single dose, or a plurality of doses given, for example, every day, semi weekly, or weekly, given over a period of a few days, a week, or several months) may provide the subject with a period of efficacy (for example, for two weeks, a month, two months, or more) during which the senolytic agent is not administered, and the subject experiences alleviation, reduction, or reversal of one or more adverse signs or symptoms of the condition being treated.

To treat a particular senescence-related condition with a senolytic agent the therapeutic regimen will depend on the location of the senescent cells, and the pathophysiology of the disease.

Senescence-Related Conditions Suitable for Treatment

The senolytic agents can be used for prevention or treatment of various senescence-related conditions. Such conditions will typically (although not necessarily) characterized by an overabundance of senescent cells (such as cells expressing p16 and other senescence markers) in or around the site of the condition, or an overabundance of expression of p16 and other senescence markers, in comparison with the frequency of such cells or the level of such expression in unaffected tissue. Non-limiting examples of current interest include the treatment of osteoarthritis, eye disease, lung disease, and atherosclerosis as illustrated in the following sections.

Treatment of Osteoarthritis

The senolytic agents listed in this disclosure can be developed for treating osteoarthritis, or for selectively eliminating senescent cells in or around a joint of a subject in need thereof, including but not limited to a joint affected by osteoarthritis.

Osteoarthritis degenerative joint disease is characterized by fibrillation of the cartilage at sites of high mechanical stress, bone sclerosis, and thickening of the synovium and the joint capsule. Fibrillation is a local surface disorganization involving splitting of the superficial layers of the cartilage. The early splitting is tangential with the cartilage surface, following the axes of the predominant collagen bundles. Collagen within the cartilage becomes disorganized, and proteoglycans are lost from the cartilage surface. In the absence of protective and lubricating effects of proteoglycans in a joint, collagen fibers become susceptible to degradation, and mechanical destruction ensues. Predisposing risk factors for developing osteoarthritis include increasing age, obesity, previous joint injury, overuse of the joint, weak thigh muscles, and genetics. Symptoms of osteoarthritis include sore or stiff joints, particularly the hips, knees, and lower back, after inactivity or overuse; stiffness after resting that goes away after movement; and pain that is worse after activity or toward the end of the day.

Compounds illustrated in this invention can be used to reduce or inhibit loss or erosion of proteoglycan layers in a joint, reduces inflammation in the affected joint, and promotes, stimulates, enhances, or induces production of collagen, for example, type 2 collagen. The compound may causes a reduction in the amount, or level, of inflammatory cytokines, such as IL-6, produced in a joint and inflammation is reduced. The compounds can be used for treating osteoarthritis and/or inducing collagen, for example, Type 2 collagen, production in the joint of a subject. A compound also can be used for decreasing, inhibiting, or reducing production of metalloproteinase 13 (MMP-13), which degrades collagen in a joint, and for restoring proteoglycan layer or inhibiting loss and/or degradation of the proteoglycan layer.

Potential benefits of treatment with a senolytic agent include inhibiting or reversing cartilage or bone erosion. The senolytic compound may restore or inhibit deterioration of strength of a join, or reduce joint pain.

Treatment of Ophthalmic Conditions

The senolytic agents listed in this disclosure can be used for preventing or treating an adverse ophthalmic condition in a subject in need thereof by removing senescent cells in or around an eye of the subject, whereby at least one sign or symptom of the disease is decreased in severity. Such conditions include both back-of-the-eye diseases, and front-of-the-eye diseases. The senolytic agents listed in this disclosure can be developed for selectively eliminating senescent cells in or around ocular tissue in a subject in need thereof.

Diseases of the eye that can be treated include presbyopia, macular degeneration (including wet or dry AMD), diabetic retinopathy, and glaucoma.

Macular degeneration is a neurodegenerative condition that can be characterized as a back-of-the-eye disease, It causes the loss of photoreceptor cells in the central part of retina, called the macula. Macular degeneration can be dry or wet. The dry form is more common than the wet, with about 90% of age-related macular degeneration (AMD) patients diagnosed with the dry form. The wet form of the disease can lead to more serious vision loss. Age and certain genetic factors and environmental factors can be risk factors for developing AMD. Environmental factors include, for example, omega-3 fatty acids intake, estrogen exposure, and increased serum levels of vitamin D. Genetic risk factors can include, for example, reduced ocular Dicer1 levels, and decreased micro RNAs, and DICER1 ablation.

Dry AMD is associated with atrophy of the retinal pigment epithelium (RPE) layer, which causes loss of photoreceptor cells. The dry form of AMD can result from aging and thinning of macular tissues and from deposition of pigment in the macula. With wet AMD, new blood vessels can grow beneath the retina and leak blood and fluid. Abnormally leaky choroidal neovascularization can cause the retinal cells to die, creating blind spots in central vision. Different forms of macular degeneration can also occur in younger patients. Non-age related etiology can be linked to, for example, heredity, diabetes, nutritional deficits, head injury, or infection.

The formation of exudates, or "drusen," underneath the Bruch's membrane of the macula is can be a physical sign that macular degeneration can develop. Symptoms of macular degeneration include, for example, perceived distortion of straight lines and, in some cases, the center of vision appears more distorted than the rest of a scene; a dark, blurry area or "white-out" appears in the center of vision; or color perception changes or diminishes.

Another back-of-the-eye disease is diabetic retinopathy (DR). According to Wikipedia, the first stage of DR is non-proliferative, and typically has no substantial symptoms or signs. NPDR is detectable by fundus photography, in which microaneurysms (microscopic blood-filled bulges in the artery walls) can be seen. If there is reduced vision, fluorescein angiography can be done to see the back of the eye. Narrowing or blocked retinal blood vessels can be seen clearly and this is called retinal ischemia (lack of blood flow). Macular edema in which blood vessels leak their contents into the macular region can occur at any stage of NPDR. The symptoms of macular edema are blurred vision and darkened or distorted images that are not the same in both eyes. Ten percent (10%) of diabetic patients will have vision loss related to macular edema. Optical Coherence Tomography can show the areas of retinal thickening (due to fluid accumulation) of macular edema.

In the second stage of DR, abnormal new blood vessels (neovascularization) form at the back of the eye as part of proliferative diabetic retinopathy (PDR); these can burst and bleed (vitreous hemorrhage) and blur the vision, because these new blood vessels are fragile. The first time this bleeding occurs, it may not be very severe. In most cases, it will leave just a few specks of blood, or spots floating in a person's visual field, though the spots often go away after few hours. These spots are often followed within a few days or weeks by a much greater leakage of blood, which blurs the vision. In extreme cases, a person may only be able to tell light from dark in that eye. It may take the blood anywhere from a few days to months or even years to clear from the inside of the eye, and in some cases the blood will not clear. These types of large hemorrhages tend to happen more than once, often during sleep. On funduscopic exam, a doctor will see cotton wool spots, flame hemorrhages (similar lesions are also caused by the alpha-toxin of *Clostridium novyi*), and dot-blot hemorrhages.

Presbyopia is an age-related condition where the eye exhibits a progressively diminished ability to focus on near objects as the speed and amplitude of accommodation of a normal eye decreases with advancing age. Loss of elasticity of the crystalline lens and loss of contractility of the ciliary muscles can cause presbyopia. Age-related changes in the mechanical properties of the anterior lens capsule and posterior lens capsule suggest that the mechanical strength of the posterior lens capsule decreases significantly with age. The laminated structure of the capsule of the eye also changes and can result, at least in part, from a change in the composition of the tissue.

Compounds provided by this disclosure can slow the disorganization of the type IV collagen network, decrease or inhibit epithelial cell migration and can also delay the onset of presbyopia or decrease or slow the progressive severity of the condition. They can also be useful for post-cataract surgery to reduce the likelihood of occurrence of PCO.

Another condition treatable with senolytic agents is glaucoma. Normally, clear fluid flows into and out of the front part of the eye, known as the anterior chamber. In individuals who have open/wide-angle glaucoma, the clear fluid drains too slowly, leading to increased pressure within the eye. If left untreated, the high pressure in the eye can subsequently damage the optic nerve and can lead to complete blindness. The loss of peripheral vision is caused by the death of ganglion cells in the retina. The effect of a therapy on inhibiting progression of glaucoma can be monitored by automated perimetry, gonioscopy, imaging technology, scanning laser tomography, HRT3, laser polarimetry, GDX, ocular coherence tomography, ophthalmoscopy, and pachymeter measurements that determine central corneal thickness.

Ophthalmic conditions treatable with senolytic agents include ischemic or vascular conditions, such as diabetic retinopathy, glaucomatous retinopathy, ischemic arteritic optic neuropathies, and vascular diseases characterized by arterial and venous occlusion, retinopathy of prematurity and sickle cell retinopathy.

Ophthalmic conditions treatable with senolytic agents include degenerative conditions, such as dermatochalasis, ptosis, keratitis sicca, Fuch's corneal dystrophy, presbyopia, cataract, wet age related macular degeneration (wet AMD), dry age related macular degeneration (dry AMD); degenerative vitreous disorders, including vitreomacular traction (VMT) syndrome, macular hole, epiretinal membrane (ERM), retinal tears, retinal detachment, and proliferative vitreoretinopathy (PVR).

Ophthalmic conditions treatable with senolytic agents include genetic conditions, such as retinitis pigmentosa, Stargardt disease, Best disease and Leber's hereditary optic neuropathy (LHON). Ophthalmic conditions treatable with a senolytic agent include conditions caused by a bacterial, fungal, or virus infection. These include conditions caused or provoked by an etiologic agent such as herpes zoster varicella (HZV), herpes simplex, cytomegalovirus (CMV), and human immunodeficiency virus (HIV).

Ophthalmic conditions treatable with senolytic agents include inflammatory conditions, such as punctate choroiditis (PIC), multifocal choroiditis (MIC) and serpiginous choroidopathy. Ophthalmic conditions treatable with a senolytic agent also include iatrogenic conditions, such as a post-vitrectomy cataract and radiation retinopathy.

Potential benefits of treatment with a senolytic agent include reversing or inhibiting progression of any of the aforelisted signs and symptoms of ocular diseases, such as neovascularization, vaso-obliteration, and an increase in intraocular pressure, leading to an impairment of retinal function and loss of vision.

Treatment of Pulmonary Conditions

The senolytic agents listed in this disclosure can be developed for treating pulmonary disease, or for selectively eliminating senescent cells in or around a lung of a subject in need thereof. Pulmonary conditions that can be treated include idiopathic pulmonary fibrosis (IPF), chronic obstructive pulmonary disease (COPD), asthma, cystic fibrosis, bronchiectasis, and emphysema.

COPD is a lung disease defined by persistently poor airflow resulting from the breakdown of lung tissue, emphysema, and the dysfunction of the small airways, obstructive bronchiolitis. Primary symptoms of COPD include shortness of breath, wheezing, chest tightness, chronic cough, and excess sputum production. Elastase from cigarette smoke-activated neutrophils and macrophages can disintegrate the extracellular matrix of alveolar structures, resulting in enlarged air spaces and loss of respiratory capacity. COPD can be caused by, for example, tobacco smoke, cigarette smoke, cigar smoke, secondhand smoke, pipe smoke, occupational exposure, exposure to dust, smoke, fumes, and pollution, occurring over decades thereby implicating aging as a risk factor for developing COPD. High concentrations of free radicals in tobacco smoke can lead to cytokine release as part of an inflammatory response to irritants in the airway, resulting in damage the lungs by protease.

Symptoms of COPD can include shortness of breath, wheezing, chest tightness, having to clear one's throat first thing in the morning because of excess mucus in the lungs, a chronic cough that produces sputum that can be clear, white, yellow or greenish, cyanosis, frequent respiratory infections, lack of energy, and unintended weight loss.

Pulmonary fibrosis is a chronic and progressive lung disease characterized by stiffening and scarring of the lung, which can lead to respiratory failure, lung cancer, and heart failure. Fibrosis is associated with repair of epithelium. Fibroblasts are activated, production of extracellular matrix proteins is increased, and transdifferentiation to contractile myofibroblasts contribute to wound contraction. A provisional matrix plugs the injured epithelium and provides a scaffold for epithelial cell migration, involving an epithelial-mesenchymal transition (EMT). Blood loss associated with epithelial injury induces platelet activation, production of growth factors, and an acute inflammatory response. Normally, the epithelial barrier heals and the inflammatory response resolves. However, in fibrotic disease the fibroblast response continues, resulting in unresolved wound healing. Formation of fibroblastic foci is a feature of the disease, reflecting locations of ongoing fibrogenesis.

Subjects at risk of developing pulmonary fibrosis include, for example, those exposed to environmental or occupational pollutants, such as asbestosis and silicosis; those who smoke cigarettes; those who have a connective tissue diseases such as RA, SLE, scleroderma, sarcoidosis, or Wegener's granulomatosis; those who have infections; those who take certain medications, including, for example, amiodarone, bleomycin, busufan, methotrexate, and nitrofurantoin; those subject to radiation therapy to the chest; and those whose family member have pulmonary fibrosis.

Other pulmonary conditions that can be treated by using a compound include emphysema, asthma, bronchiectasis, and cystic fibrosis. Pulmonary diseases can also be exacerbated by tobacco smoke, occupational exposure to dust, smoke, or fumes, infection, or pollutants that contribute to inflammation.

Bronchiectasis can result from damage to the airways that causes them to widen and become flabby and scarred. Bronchiectasis can be caused by a medical condition that injures the airway walls or inhibits the airways from clearing mucus. Examples of such conditions include cystic fibrosis and primary ciliary dyskinesia (PCD). When only one part of the lung is affected, the disorder can be caused by a blockage rather than a medical condition.

The methods provided in this disclosure for treating or reducing the likelihood of a pulmonary condition can also be used for treating a subject who is aging and has loss of pulmonary function, or degeneration of pulmonary tissue. Effects of treatment can be determined using techniques that evaluate mechanical functioning of the lung, for example, techniques that measure lung capacitance, elastance, and airway hypersensitivity can be performed. For example, expiratory reserve volume (ERV), forced vital capacity (FVC), forced expiratory volume (FEV) (e.g., FEV in one second, FEV1), FEV1/FEV ratio, forced expiratory flow 25% to 75%, and maximum voluntary ventilation (MVV), peak expiratory flow (PEF), slow vital capacity (SVC) can be measured. Peripheral capillary oxygen saturation ($SpO_2$) can also be measured; normal oxygen levels are typically between 95% and 100%. An $SpO_2$ level below 90% indicates that the subject has hypoxemia.

Potential benefits of treatment with a senolytic agent include alleviating or halting progression of one or more signs or symptoms of the condition being treated, as indicated above. Objectives may include increasing lung volume or capacity, and manifestations thereof such as improving oxygen saturation.

Treatment of Atherosclerosis

The senolytic compounds can be used for the treatment of atherosclerosis: for example, by inhibiting formation, enlargement, or progression of atherosclerotic plaques in a subject. The senolytic compounds can also be used to enhance stability of atherosclerotic plaques that are present in one or more blood vessels of a subject, thereby inhibiting them from rupturing and occluding the vessels.

Atherosclerosis is characterized by patchy intimal plaques, atheromas, that encroach on the lumen of medium-sized and large arteries; the plaques contain lipids, inflammatory cells, smooth muscle cells, and connective tissue. Atherosclerosis can affect large and medium-sized arteries, including the coronary, carotid, and cerebral arteries, the aorta and branches thereof, and major arteries of the extremities.

Atherosclerosis may lead to an increase in artery wall thickens. Symptoms develop when growth or rupture of the plaque reduces or obstructs blood flow; and the symptoms can vary depending on which artery is affected. Atherosclerotic plaques can be stable or unstable. Stable plaques regress, remain static, or grow slowly, sometimes over several decades, until they can cause stenosis or occlusion. Unstable plaques are vulnerable to spontaneous erosion, fissure, or rupture, causing acute thrombosis, occlusion, and infarction long before they cause hemodynamically significant stenosis. Clinical events can result from unstable plaques, which do not appear severe on angiography; thus, plaque stabilization can be a way to reduce morbidity and mortality. Plaque rupture or erosion can lead to major cardiovascular events such as acute coronary syndrome and stroke. Disrupted plaques can have a greater content of lipid, macrophages, and have a thinner fibrous cap than intact plaques.

Atherosclerosis is thought to be due in significant part to a chronic inflammatory response of white blood cells in the walls of arteries. This is promoted by low-density lipoproteins (LDL), plasma proteins that carry cholesterol and triglycerides, in the absence of adequate removal of fats and cholesterol from macrophages by functional high-density lipoproteins (HDL). The earliest visible lesion of atherosclerosis is the "fatty streak," which is an accumulation of lipid-laden foam cells in the intimal layer of the artery. The hallmark of atherosclerosis is atherosclerotic Diagnosis of atherosclerosis and other cardiovascular disease can be based on symptoms, for example, angina, chest pressure, numbness or weakness in arms or legs, difficulty speaking or slurred speech, drooping muscles in face, leg pain, high blood pressure, kidney failure and/or erectile dysfunction, medical history, and/or physical examination of a patient. Diagnosis can be confirmed by angiography, ultrasonography, or other imaging tests. Subjects at risk of developing cardiovascular disease include those having any one or more of predisposing factors, such as a family history of cardiovascular disease and those having other risk factors, for example, predisposing factors including high blood pressure, dyslipidemia, high cholesterol, diabetes, obesity and cigarette smoking, sedentary lifestyle, and hypertension. The condition can be assessed, for example, by angiography, electrocardiography, or stress test.

Potential benefits of treatment with a senolytic agent include alleviating or halting progression of one or more signs or symptoms of the condition, such as the frequency of plaques, the surface area of vessels covered by plaques, angina, and reduced exercise tolerance.

Definitions

A "senescent cell" is generally thought to be derived from a cell type that typically replicates, but as a result of aging or other event that causes a change in cell state, can no longer replicate. For the purpose of practicing some aspects of this invention, senescent cells can be identified as expressing p16, or at least one marker selected from p16, senescence-associated β-galactosidase, and lipofuscin; sometimes two or more of these markers, and other markers of the senescence-associated secretory profile (SASP) such as but not limited to interleukin 6, and inflammatory, angiogenic and extracellular matrix modifying proteins. Unless explicity stated otherwise, the senescent cells referred to in the claims do not include cancer cells.

A "senescence associated", "senescence related" or "age related" disease, disorder, or condition is a physiological condition that presents with one or more symptoms or signs that are adverse to the subject. The condition is "senescence associated" if it is "caused or mediated at least in part by senescent cells." This means that at least one component of the SASP in or around the affected tissue plays a role in the pathophysiology of the condition such that elimination of at least some of the senescent cells in the affected tissue results in substantial relief or lessening of the adverse symptoms or signs, to the patient's benefit. Senescence associated disorders that can potentially be treated or managed using the methods and products according to this invention include disorders referred to in this disclosure and in previous disclosures referred to in the discussion. Unless explicitly stated otherwise, the term does not include cancer.

An inhibitor of protein function or proteasome function is a compound that to a substantial degree prevents the target protein already expressed in a target cell from performing an enzymatic, binding, or regulatory function that the protein or proteasome normally performs in the target cell. This results in elimination of the target cell or rendering the cell more susceptible to the toxicity of another compound or event. A compound qualifies as a "proteasome inhibitor" or a compound that "inhibits proteasome activity" in this disclosure if it has an $IC_{50}$ when tested in an assay according to Example 1 below (exemplified in FIGS. 2A, 2B, and 2C) that is less than 1,000 nM (1.0 µM). Activity that is less than 100 nM or 10 nM, or between 100 nM and 1 nM is often preferred, depending on the context.

A compound, composition or agent is typically referred to as "senolytic" if it eliminates senescent cells, compared with replicative cells of the same tissue type, or quiescent cells lacking SASP markers. Alternatively or in addition, a compound or combination may effectively be used if it decreases the release of pathological soluble factors or mediators as part of the senescence associated secretory phenotype that play a role in the initial presentation or ongoing pathology of a condition, or inhibit its resolution. In this respect, the term "senolytic" refers to functional inhibition, such that compounds that work primarily by inhibiting rather than eliminating senescent cells (senescent cell inhibitors) can be used in a similar fashion with ensuing benefits. Model senolytic compositions and agents in this disclosure have an $EC_{50}$ when tested in an assay according to Example 2 below (exemplified in FIGS. 2A, 2B, and 2C) that is less than 1 µM. Activity that is less than 0.1 µM, or between 1 µM and 0.1 µM may be preferred. The selectivity index (SI) ($EC_{50}$ of senescent cells compared with non-senescent cells of the same tissue type) may be 1, 2, 5, or 10 or more, depending on the context.

Selective removal or "elimination" of senescent cells from a mixed cell population or tissue doesn't require that all cells bearing a senescence phenotype be removed: only that the proportion of senescent cells initially in the tissue that remain after treatment is substantially higher than the proportion of non-senescent cells initially in the tissue that remain after the treatment.

Successful "treatment" of a condition may have any effect that is beneficial to the subject being treated. This includes decreasing severity, duration, or progression of a condition, or of any adverse signs or symptoms resulting therefrom. In some circumstances, senolytic agents can also be used to prevent or inhibit presentation of a condition for which a subject is susceptible, for example, because of an inherited susceptibility of because of medical history.

A "therapeutically effective amount" is an amount of a compound of the present disclosure that (i) treats the particular disease, condition, or disorder, (ii) attenuates, ameliorates, or eliminates one or more symptoms of the particular disease, condition, or disorder, (iii) prevents or delays the onset of one or more symptoms of the particular disease, condition, or disorder described herein, (iv) prevents or delays progression of the particular disease, condition or disorder, (v) at least partially reverses damage caused by the condition prior to treatment; or has a plurality of such effects in any combination.

A "phosphorylated" form of a compound is a compound which bears one or more phosphate groups covalently bound to the core structure through an oxygen atom, which was typically but not necessarily present on the molecule before phosphorylation. For example, one or more —OH or —COOH groups may have been substituted in place of the hydrogen with a phosphate group which is either —OPO$_3$H$_2$ or —C$_n$PO$_3$H$_2$ (where n is 1 to 4). In some phosphorylated forms, the phosphate group may be removed in vivo (for example, by enzymolysis), in which case the phosphorylated form may be a pro-drug of the non-phosphorylated form. A non-phosphorylated form has no such phosphate group. A dephosphorylated form is a derivative of a phosphorylated molecule after at least one phosphate group has been removed.

"Peptidic" compounds of this invention refers collectively or in the alternative to compounds that contains either a normal peptide with amino acids linked together by peptide bonds, or that contain a peptidomimetic portion that is capable of mimicking a biological action of a parent peptide. A "peptidomimetic" compound is a bioisostere of a parent peptide sequence that contains structural elements that are positioned in three-dimensional space to have chemical effects at locations that mimic the chemical effects of corresponding structural elements of the parent peptide. As a result, the peptidomimetic compound binds to or interacts with a target biological molecule in a way that mimics an activity of the parent peptide, while typically also having a desirable physical and/or non-target biological property that differs from the parent peptide, such as resistance to proteolytic degradation or increased bioavailability. A peptidomimetic compound typically includes a backbone and a configuration of side chains corresponding to the peptide backbone and side chains of the parent peptide. Included are retroinverso peptides, peptoids, and other backbones that present side chains in similar fashion to a parent peptide, such as substitutions of the amide bond hydrogen moiety by methyl groups (N-methylation) or other alkyl groups. A peptidic compound can have a portion that is a normal polypeptide, and a portion that is a peptidomimetic sequence or monomer. A peptidic compound may have other reactive groups or modifications at either terminal of the backbone or on one or more side chains. Possible modifications include an N-terminal modification (such as an oxo or thio group) and a C-terminal modification (such as a C-terminal epoxyketone).

A "retroinverso" peptide is a sequence of D-amino acid residues that is the same as the sequence of a parent L-peptide, except it is configured in the reverse order. A retroinverso peptide can maintain an amino acid sidechain topology that is similar to that of the parent L-amino acid peptide and be more resistant to proteolytic degradation. A "peptoid" is a class of peptidomimetic compounds, or a unit thereof, based on N-substituted glycine monomer units where the sidechain groups are linked to the nitrogen atom of the peptidic backbone. Peptoid compounds can be designed to display sidechain groups analogous to the bioactive peptide side chains of a parent peptide sequence, while the peptoid backbone can provide resistance to proteolytic degradation.

"Small molecule" senolytic agents have molecular weights less than 20,000 daltons, and are often less than 10,000, 5,000, or 2,000 daltons. Small molecule inhibitors are not antibody molecules or oligonucleotides, and typically have no more than five hydrogen bond donors (the total number of nitrogen-hydrogen and oxygen-hydrogen bonds), and no more than 10 hydrogen bond acceptors that are nitrogen or oxygen atoms.

"Prodrug" refers to a derivative of an active agent that requires a transformation within the body to release the active agent. The transformation can be an enzymatic transformation. Sometimes, the transformation is a cyclization transformation, or a combination of an enzymatic transformation and a cyclization transformation. Prodrugs are frequently, although not necessarily, pharmacologically inactive until converted to the active agent.

"Promoiety" refers to a form of protecting group that when used to mask a functional group within an active agent converts the active agent into a prodrug. Typically, the promoiety will be attached to the drug via bond(s) that are cleaved by enzymatic or non-enzymatic means in vivo. Exemplary promoiety groups include acyl groups capable of forming an ester or thioester group with a hydroxyl or thiol functional group of a compound, and substituted alkyl groups capable of forming an ether or thioether group with a hydroxyl or thiol functional group of a compound, which groups can be cleaved in vivo as described above.

Unless otherwise stated or required, each of the compound structures referred to in the invention include conjugate acids and bases having the same structure, crystalline and amorphous forms of those compounds, pharmaceutically acceptable salts, and prodrugs. This includes, for example, tautomers, polymorphs, solvates, hydrates, unsolvated polymorphs (including anhydrates). The compound may be any stereoisomer of the structure shown, or a mixture thereof, unless a particular stereoisomer or a particular chiral structure is explicity referred to.

Unless otherwise stated or implied, the term "substituted" when used to modify a specified group or radical means that one or more hydrogen atoms of the specified group or radical are each independently replaced with the same or different substituent groups which is not hydrogen. Unless indicated otherwise, the nomenclature of substituents is arrived at by naming the terminal portion of the functionality followed by the adjacent functionality toward the point of attachment. For example, the substituent "arylalkyloxycarbonyl" refers to the group (aryl)-(alkyl)-O—C(O)—.

A "linker" is a moiety that covalently connects two or more chemical structures, and has a backbone of 100 atoms or less in length between the two structures. The linker may be cleavable or non-cleavable. The linker typically has a backbone of between 1 and 20 or between 1 and 100 atoms in length, in linear or branched form. The bonds between backbone atoms may be saturated or unsaturated. The linker backbone may include a cyclic group, for example, an optionally substituted aryl, heteroaryl, heterocycle or cycloalkyl group.

Except where otherwise stated or required, other terms used in the specification have their ordinary meaning.

Incorporation by Reference

For all purposes in the United States and in other jurisdictions where effective, each and every publication and patent document cited in this disclosure is hereby incorporated herein by reference in its entirety for all purposes to the same extent as if each such publication or document was specifically and individually indicated to be incorporated herein by reference.

US 2016/0339019 A1 (Laberge et al.) and US 20170266211 A1 (David et al.) are hereby incorporated herein by reference in their entirety for all purposes, including but not limited to the identification, formulation, and use of compounds for eliminating or reducing the activity of senescent cells and treating particular senescence-related conditions, including but not limited to those referred to in this disclosure. U.S. patent applications US 2018/0000816 A1 and PCT/US2018/046553 are hereby incorporated herein for all purposes, including but not limited to the identification, formulation, and use of compounds for eliminating or reducing the activity of senescent cells and treating various ophthalmic conditions. U.S. patent applications US 2018/0000816 A1 and PCT/US2018/046567 are hereby incorporated herein for all purposes, including but not limited to the identification, formulation, and use of compounds for eliminating or reducing the activity of senescent cells and treating various pulmonary conditions. U.S. patent application Ser. No. 16/181,163 are hereby incorporated herein for all purposes, including but not limited to the identification, formulation, and use of compounds for eliminating or reducing the activity of senescent cells and treating atherosclerosis.

EXAMPLES

Example 1: Measuring Proteasome Activity

This example provides assays by which the reader may ascertain whether a test compound has sufficient inhibitory capacity for the target pathways to be developed as a senolytic agent. Information from these assays may be combined with information from cell lysis assays (Examples 2 and 3) to select compounds for further development.

Test compounds are assayed for inhibition of the chymotrypsin-like activity of the proteasome β5 subunit by monitoring the release of a fluorogenic product after cleavage of a substrate peptide. The active protease cleaves an amide bond between the C-terminal amino acid of a substrate peptide and aminoemethylcoumarin, allowing enzyme activity to be quantitated fluorometrically.

Compounds are tested in a 384-well format. A 1:3 dilution series of compound in DMSO is diluted into reaction buffer (20 mM HEPES pH 7.5, 0.01% BSA, 0.02% SDS, 0.5 mM EDTA, 100 mM NaCl) so that when added to the reaction mix the final concentration of DMSO does not exceed 1%. To initialize the reaction, test compounds and substrate are added for a final reaction volume of 50 μL per well containing the following: 20 mM HEPES pH 7.5, 0.01% BSA, 0.02% SDS, 0.5 mM EDTA, 100 mM NaCl, 0.5 nM constitutive 20S proteasome, and 50 μM substrate (Succinyl-Leu-Leu-Val-Tyr-AMC).

Reactions are mixed and an initial reading is recorded after 5 minutes using and excitation wavelength of 360 nM and emission of 450 nM. A second endpoint measurement is taken at 1 hour. Relative enzymatic activity is calculated from the change in fluorescence (final minus initial) relative to DMSO control.

Example 2A: Measuring Senolytic Activity in Fibroblasts

Before initiating experiments in vivo, it is usually helpful to screen potential senolytic agents for their potency for removing senescent cells, and their selectivity for senescent cells in comparison with non-senescent cells in the same tissue.

Human fibroblast IMR90 cells can be obtained from the American Type Culture Collection (ATCC®) with the designation CCL-186. The cells are maintained at <75% confluency in DMEM containing FBS and Pen/Strep in an atmosphere of 3% O2, 10% CO2, and ~95% humidity. The cells are divided into three groups: irradiated cells (cultured for 14 days after irradiation prior to use), proliferating normal cells (cultured at low density for one day prior to use), and quiescent cells (cultured at high density for four day prior to use).

On day 0, the irradiated cells are prepared as follows. IMR90 cells are washed, placed in T175 flasks at a density of 50,000 cells per mL, and irradiated at 10-15 Gy. Following irradiation, the cells are plated at 100 μL in 96-well plates. On days 1, 3, 6, 10, and 13, the medium in each well is aspirated and replaced with fresh medium.

On day 10, the quiescent healthy cells are prepared as follows. IMR90 cells are washed, combined with 3 mL of TrypLE trypsin-containing reagent (Thermofisher Scientific, Waltham, Mass.) and cultured for 5 min until the cells have rounded up and begin to detach from the plate. Cells are dispersed, counted, and prepared in medium at a concentration of 50,000 cells per mL. 100 μL of the cells is plated in each well of a 96-well plate. Medium is changed on day 13.

On day 13, the proliferating healthy cell population is prepared as follows. Healthy IMR90 cells are washed, combined with 3 mL of TrypLE and cultured for 5 minutes until the cells have rounded up and begin to detach from the plate. Cells are dispersed, counted, and prepared in medium at a concentration of 25,000 cells per mL. 100 μL of the cells is plated in each well of a 96-well plate.

On day 14, test inhibitors are combined with the cells as follows. A DMSO dilution series of each test compound is prepared at 200 times the final desired concentration in a 96-well PCR plate. Immediately before use, the DMSO stocks are diluted 1:200 into pre-warmed complete medium. Medium is aspirated from the cells in each well, and 100 μL/well of the compound containing medium is added.

Candidate senolytic agents for testing are cultured with the cells for 6 days, replacing the culture medium with fresh medium and the same compound concentration on day 17. Test inhibitors are cultured with the cells for 3 days. The assay system uses the properties of a thermostable luciferase to enable reaction conditions that generate a stable luminescent signal while simultaneously inhibiting endogenous ATPase released during cell lysis. At the end of the culture period, 100 μL of CellTiter-Glo® reagent (Promega Corp., Madison, Wis.) is added to each of the wells. The cell plates are placed for 30 seconds on an orbital shaker, and luminescence is measured.

FIG. 2A provides data for senolytic activity and proteasome binding for structures selected from FIGS. 1A and 1D. FIG. 2B provides data for senolytic activity and proteasome binding for structures selected from FIG. 1B. FIG. 2C provides data for structures selected from FIG. 1C

Example 2B: Measuring Senolytic Activity in HUVEC Cells

Human umbilical vein (HUVEC) cells from a single lot were expanded in Vascular Cell Basal Media supplemented with the Endothelial Cell Growth Kit™-VEGF from ATCC to approximately eight population doublings then cryopreserved. Nine days prior to the start of the assay, cells for the senescent population were thawed and seeded at approximately 27,000/cm$_2$. All cells were cultured in humidified incubators with 5% CO2 and 3% O$_2$ and media was changed every 48 hr. Two days after seeding, the cells were irradiated, delivering 12 Gy radiation from an X-ray source. Three days prior to the start of the assay, cells for the non-senescent populations are thawed and seeded as for the senescent population. One day prior to the assay, all cells were trypsinized and seeded into 384-well plates, 5,000/well senescent cells and 10,000/well non-senescent in separate plates in a final volume of 55 μL/well. In each plate, the central 308 wells contained cells and the outer perimeter of wells was filled with 70 μL/well deionized water.

On the day of the assay, compounds were diluted from 10 mM stocks into media to provide the highest concentration working stock, aliquots of which were then further diluted in media to provide the remaining two working stocks. To initiate the assay, 5 μL of the working stock was added to the cell plates. The final test concentrations were 20, 2, and 0.2 μM. In each plate, 100 test compounds were assayed in triplicate at a single concentration along with a three wells of a positive control and five no treatment (DMSO) controls. Following compound addition, the plates are returned to the incubators for three days.

Cell survival was assessed indirectly by measuring total ATP concentration using CellTiter-Glo™ reagent (Promega). The resultant luminescence was quantitated with an EnSpire™ plate reader (Perkin Elmer). The relative cell viability for each concentration of a compound was calculated as a percentage relative to the no-treatment controls for the same plate.

For follow-up dose responses of potential lead compounds, 384-well plates of senescent and non-senescent cells were prepared as described above. Compounds were prepared as 10-point 1:3 dilution series in DMSO, then diluted to 12× in media. Five microliters of this working stock was then added to the cell plates. After three days of incubation, cell survival relative to DMSO control was calculated as described above. All measurements were preformed in quadruplicate.

Example 3: Synthesis of Proteasome Inhibitors

General Synthetic Scheme:

This scheme can be applied to the synthesis of (S)-2-((S)-2-hydroxy-4-phenylbutanamido)-4-methyl-N—((S)-1-(((S)-4-methyl-1-((R)-2-methyloxiran-2-yl)-1-oxopentan-2-yl)amino)-1-oxo-3-phenylpropan-2-yl)pentanamide

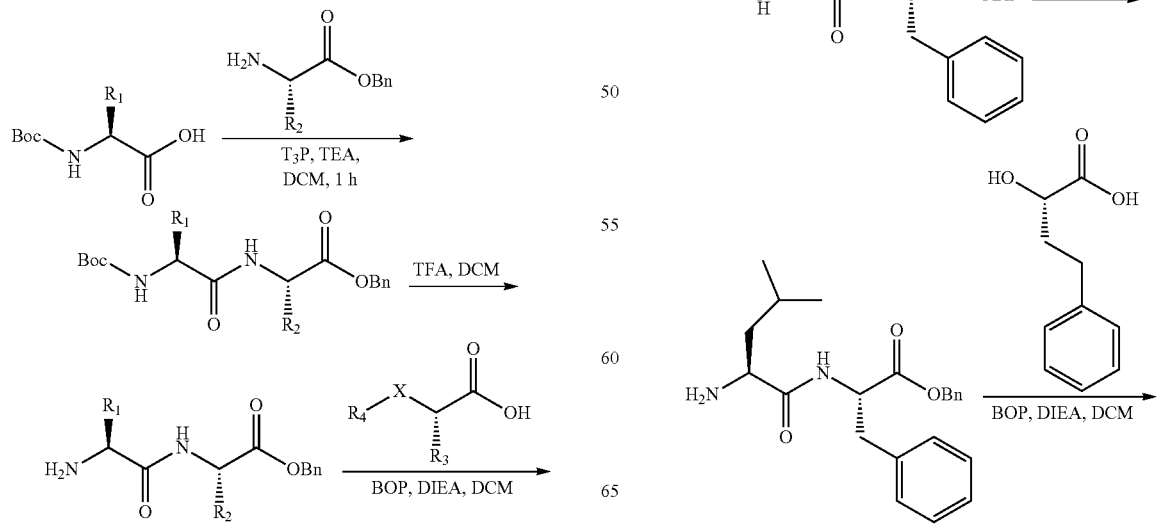

27

-continued

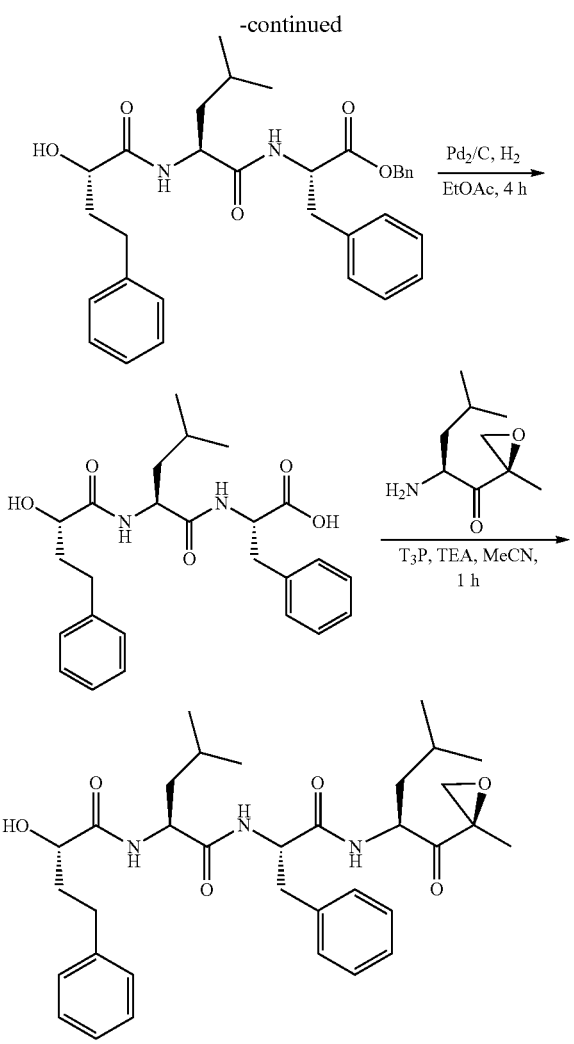

Step 1: Synthesis of benzyl (tert-butoxycarbonyl)-L-leucyl-L-phenylalaninate

The mixture of (tert-butoxycarbonyl)-L-leucine (10.2 g, 41.0 mmol), benzyl L-phenylalaninate (10.0 g, 34.2 mmol) and TEA (8.63 g, 85.5 mmol) in DCM (150 mL) was added T₃P (32.6 g, 51.3 mmol, 50% of EtOAc solution), then the mixture was stirred at 25° C. for 1 h. The reaction mixture was washed with water (200 mL×3), dried over Na₂SO₄, concentrated in vacuum. The residue was purified by column (EA in PE from 0% to 25%) to afford benzyl (tert-butoxycarbonyl)-L-leucyl-L-phenylalaninate (10.0 g, yield: 48.4%) as white solid.

Step 2: Synthesis of benzyl L-leucyl-L-phenylalaninate

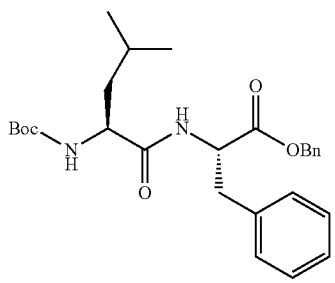 [SMILES: CC(C)C[C@H](NC(=O)OC(C)(C)C)C(=O)N[C@@H](Cc1ccccc1)C(=O)OCc1ccccc1]

To a solution of benzyl (tert-butoxycarbonyl)-L-leucyl-L-phenylalaninate (30.0 g, 64.0 mmol) in DCM (500 mL) was added TFA (100 mL) at 0° C. After 4 h at room temperature, the solvent was removed under vacuum. MTBE (200 mL) was added and the solid was filtered and washed with MTBE (100 mL×3), then dried in vacuo to afford benzyl L-leucyl-L-phenylalaninate (30.0 g, 62.1 mmol) as a white solid; LCMS (ESI⁺) [(M+H)⁺]: 369.1

Step 3: Synthesis of benzyl ((S)-2-hydroxy-4-phenylbutanoyl)-L-leucyl-L-phenylalaninate

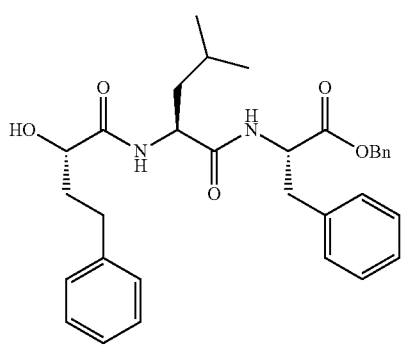 [SMILES: CC(C)C[C@H](NC(=O)[C@@H](O)CCc1ccccc1)C(=O)N[C@@H](Cc1ccccc1)C(=O)OCc1ccccc1]

A mixture of benzyl L-leucyl-L-phenylalaninate (8.00 g, 16.5 mmol), (S)-2-hydroxy-4-phenylbutanoic acid (3.40 g, 18.9 mmol), DIPEA (4.69 g, 36.3 mmol) and BOP (10.9 g, 24.7 mmol) in DCM (150 mL) was stirred at 25° C. for 16 h. The reaction mixture was concentrated under vacuum. Preparative HPLC afforded benzyl ((S)-2-hydroxy-4-phenylbutanoyl)-L-leucyl-L-phenylalaninate (14.0 g, yield: 60.8%) was obtained as white solid; LCMS (ESI⁺) [(M+H)⁺]: 531.5

Step 4: Synthesis of ((S)-2-hydroxy-4-phenylbutanoyl)-L-leucyl-L-phenylalanine

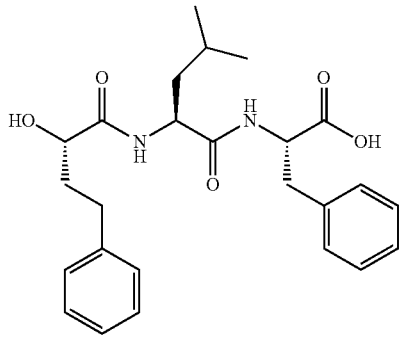 [SMILES: CC(C)C[C@H](NC(=O)[C@@H](O)CCc1ccccc1)C(=O)N[C@@H](Cc1ccccc1)C(=O)O]

A mixture of benzyl ((S)-2-hydroxy-4-phenylbutanoyl)-L-leucyl-L-phenylalaninate (12.0 g, 22.6 mmol) and Pd/C (2 g, 10%) in EtOAc (400 mL) was stirred under $H_2$ (15 psi) at 25° C. for 4 h. The reaction mixture was filtered and concentrated in vacuo to afford ((S)-2-hydroxy-4-phenylbutanoyl)-L-leucyl-L-phenylalanine (10 g, yield: 99.0%) as white solid; LCMS (ESI$^+$) [(M+H)$^+$]: 441.4

Step 5: Synthesis of (S)-2-((S)-2-hydroxy-4-phenylbutanamido)-4-methyl-N—((S)-1-(((S)-4-methyl-1-((R)-2-methyloxiran-2-yl)-1-oxopentan-2-yl)amino)-1-oxo-3-phenylpropan-2-yl)pentanamide

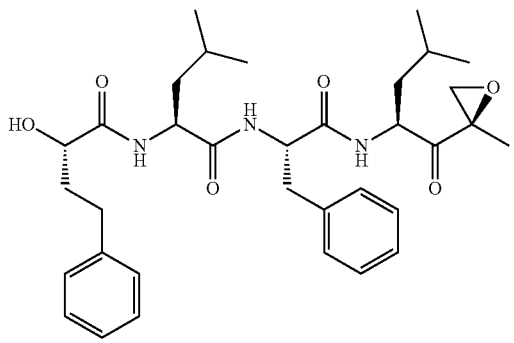 [SMILES: CC(C)C[C@H](NC(=O)[C@@H](O)CCc1ccccc1)C(=O)N[C@@H](Cc1ccccc1)C(=O)N[C@@H](CC(C)C)C(=O)[C@@]1(C)CO1]

$T_3P$ (10.7 g, 16.9 mmol) was slowly added to a solution of ((S)-2-hydroxy-4-phenylbutanoyl)-L-leucyl-L-phenylalanine (5.00 g, 11.3 mmol), (S)-2-amino-4-methyl-1-((R)-2-methyloxiran-2-yl)pentan-1-one (3.53 g, 12.4 mmol) and TEA (2.50 g, 24.8 mmol) in MeCN (100 mL). After 1 h, $H_2O$ (80 mL) was added to the suspension and stirred for 5 min. The mixture was filtered and the solid was washed with $H_2O$/MeCN (50 mL, 1:1), then dried under high vacuum to afford (S)-2-((S)-2-hydroxy-4-phenylbutanamido)-4-methyl-N—((S)-1-(((S)-4-methyl-1-((R)-2-methyloxiran-2-yl)-1-oxopentan-2-yl)amino)-1-oxo-3-phenylpropan-2-yl) pentanamide (5.1 g); LCMS (ESI$^+$) [(M+H)$^+$]: 594.7

Example 4: Efficacy of Senolytic Agents in an Osteoarthritis Model

This example illustrates the testing of an MDM2 inhibitor in a mouse model for treatment of osteoarthritis. It can be adapted mutatis mutandis to test and develop senolytic agents for use in clinical therapy.

The model was implemented as follows. C57BL/6J mice underwent surgery to cut the anterior cruciate ligament of one rear limb to induce osteoarthritis in the joint of that limb. During week 3 and week 4 post-surgery, the mice were treated with 5.8 μg of Nutlin-3A (n=7) per operated knee by intra-articular injection, q.o.d. for 2 weeks. At the end of 4 weeks post-surgery, joints of the mice were monitored for presence of senescent cells, assessed for function, monitored for markers of inflammation, and underwent histological assessment.

Two control groups of mice were included in the studies performed: one group comprising C57BL/6J or 3MR mice that had undergone a sham surgery (n=3) (i.e., surgical procedures followed except for cutting the ACL) and intra-articular injections of vehicle parallel to the GCV (ganciclovir) treated group; and one group comprising C57BL/6J or 3MR mice that had undergone an ACL surgery and received intra-articular injections of vehicle (n=5) parallel to the GCV-treated group. RNA from the operated joints of mice from the Nutlin-3A treated mice was analyzed for expression of SASP factors (mmp3, IL-6) and senescence markers (p16). qRT-PCR was performed to detect mRNA levels.

Figure 3A:
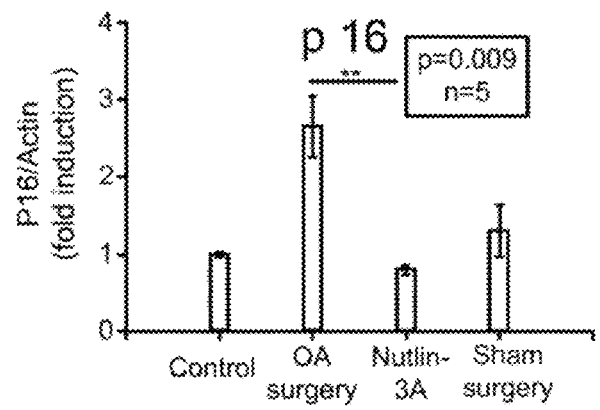
Figure 3B:
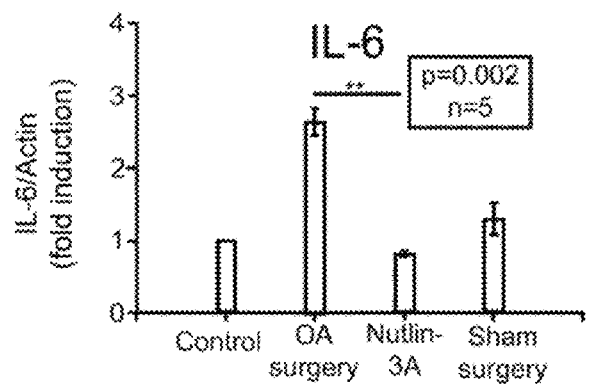
Figure 3C:
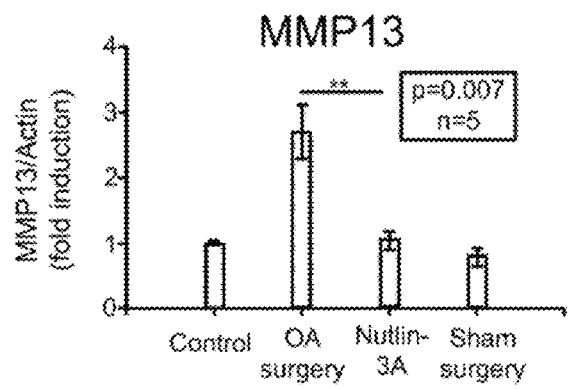

FIGS. 3A, 3B, and 3C show expression of p16, IL-6, and MMP13 in the tissue, respectively. The OA inducing surgery was associated with increased expression of these markers. Treatment with Nutlin-3A reduced the expression back to below the level of the controls. Treatment with Nutlin-3A cleared senescent cells from the joint.

Function of the limbs was assessed 4 weeks post-surgery by a weight bearing test to determine which leg the mice favored. The mice were allowed to acclimate to the chamber on at least three occasions prior to taking measurements. Mice were maneuvered inside the chamber to stand with one hind paw on each scale. The weight that was placed on each hind limb was measured over a three second period. At least three separate measurements were made for each animal at each time point. The results were expressed as the percentage of the weight placed on the operated limb versus the contralateral unoperated limb.

Figure 4A:
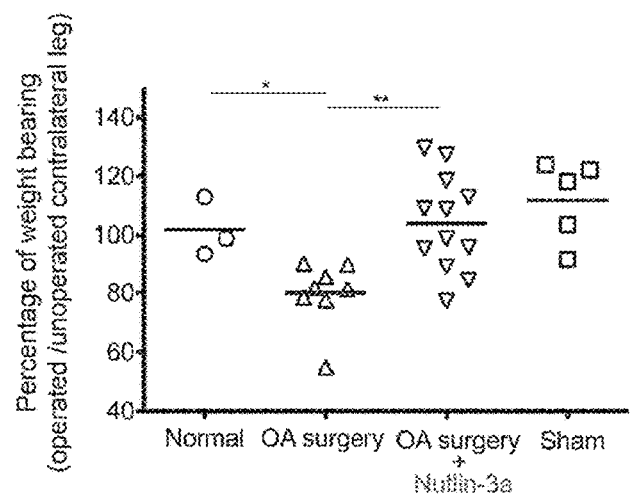

FIG. 4A shows the results of the functional study. Untreated mice that underwent osteoarthritis inducing surgery favored the unoperated hind limb over the operated hind limb (Δ). However, clearing senescent cells with Nutlin-3A abrogated this effect in mice that have undergone surgery (∇).

Figure 4B:
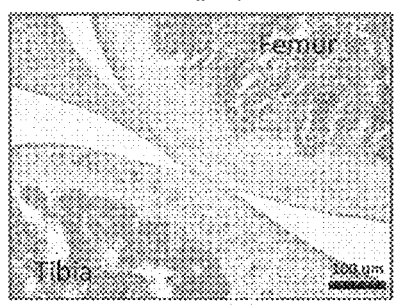
Figure 4C:
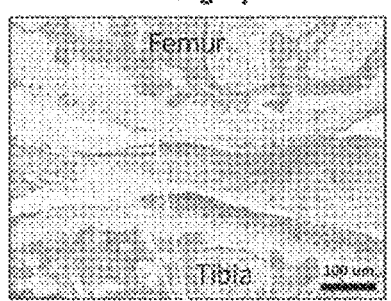
Figure 4D:
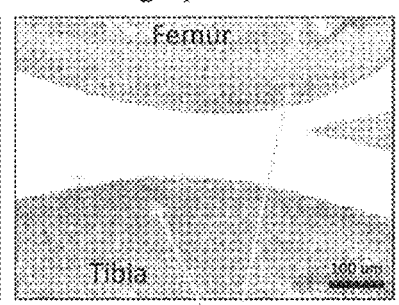

FIGS. 4B, 4C, and 4D show histopathology of joint tissue from these experiments. Osteoarthritis induced by ACL surgery caused the proteoglycan layer was destroyed. Clearing of senescent cells using Nutlin-3A completely abrogated this effect.

Example 5: Efficacy of Senolytic Agents in Models for Diabetic Retinopathy

This example illustrates the testing of a Bcl inhibitor in a mouse model for treatment of a back-of-the eye disease, specifically diabetic retinopathy. It can be adapted mutatis mutandis to test senolytic agents for use in clinical therapy.

The efficacy of model compound UBX1967 (a Bcl-xL inhibitor) was studied in the mouse oxygen-induced retinopathy (OIR) model (Scott and Fruttiger, Eye (2010) 24, 416-421, Oubaha et al, 2016). C57Bl/6 mouse pups and their CD1 foster mothers were exposed to a high oxygen environment (75% $O_2$) from postnatal day 7 (P7) to P12. At P12, animals were injected intravitreally with 1 µl test compound (200, 20, or 2 uM) formulated in 1% DMSO, 10% Tween-80, 20% PEG-400, and returned to room air until P17. Eyes were enucleated at P17 and retinas dissected for either vascular staining or qRT-PCR. To determine avascular or neovascular area, retinas were flat-mounted, and stained with isolectin B4 (IB4) diluted 1:100 in 1 mM $CaCl_2$). For quantitative measurement of senescence markers (e.g., Cdkn2a, Cdkn1a, Il6, Vegfa), qPCR was performed. RNA was isolated and cDNA was generated by reverse-transcription, which was used for qRT-PCR of the selected transcripts.

Figure 5A:
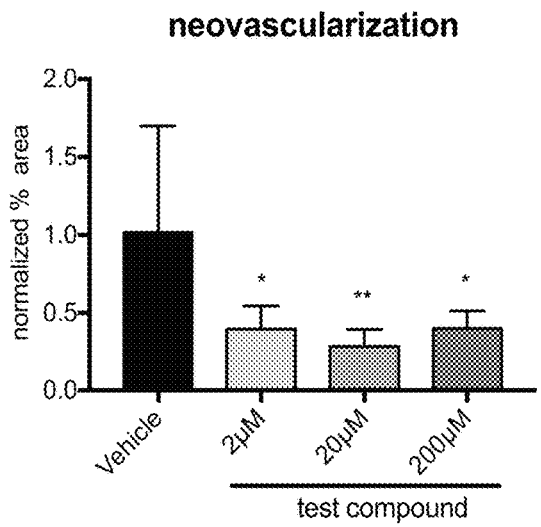
FIGS. 5A and 5B show reversal of both neovascularization and vaso-obliteration in the mouse oxygen-induced retinopathy (OIR) model when intravitreally administered with a senolytic agent.
Figure 5B:
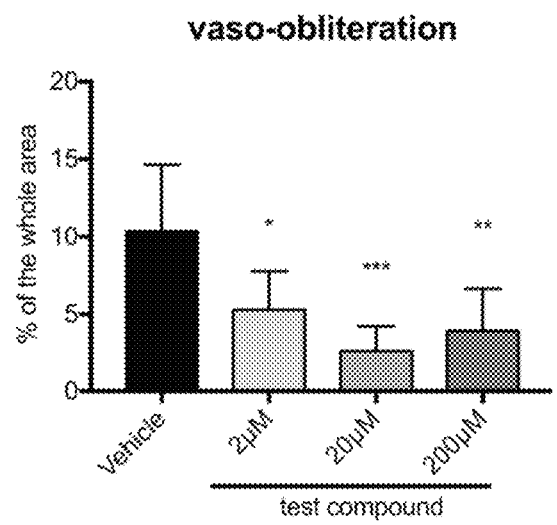

FIGS. 5A and 5B show that intravitreal ITT) administration UBX1967 resulted in statistically significant improvement in the degree of neovascularization and vaso-obliteration at all dose levels.

The efficacy of UBX1967 was also studied in the streptozotocin (STZ) model. C57BL/6J mice of 6- to 7-week were weighted and their baseline glycemia was measured (Accu-Chek™, Roche). Mice were injected intraperitoneally with STZ (Sigma-Alderich, St. Louis, Mo.) for 5 consecutive days at 55 mg/Kg. Age-matched controls were injected with buffer only. Glycemia was measured again a week after the last STZ injection and mice were considered diabetic if their non-fasted glycemia was higher than 17 mM (300 mg/L). STZ treated diabetic C57BL/6J mice were intravitreally injected with 1 µl of UBX1967 (2 µM or 20 µM, formulated as a suspension in 0.015% polysorbate-80, 0.2% Sodium Phosphate, 0.75% Sodium Chloride, pH 7.2) at 8 and 9 weeks after STZ administration. Retinal Evans blue permeation assay was performed at 10 weeks after STZ treatment.

Figure 5C:
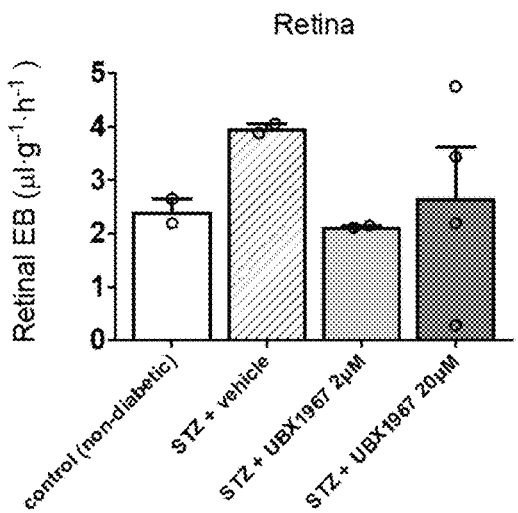
FIGS. 5C and 5D are taken from the streptozotocin (STZ) model for diabetic retinopathy. STZ-induced vascular leakage is attenuated with the intravitreal administration of a senolytic agent.
Figure 5D:
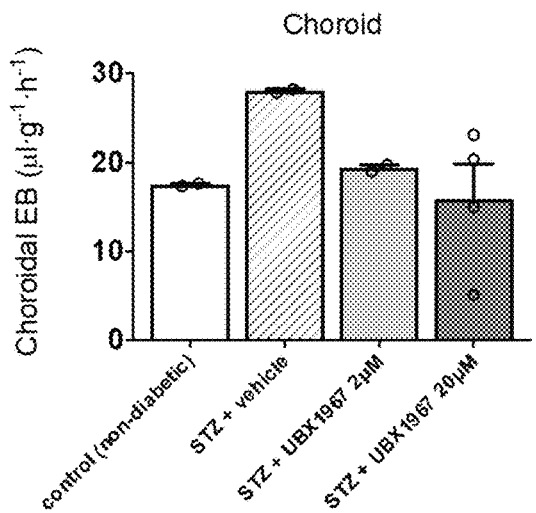

FIGS. 5C and 5D show preliminary results for this protocol. Retinal and choroidal vascular leakage after intravitreal (IVT) administration UBX1967 improved in vascular permeability at both dose levels.

Example 6: Efficacy of Senolytic Agents in a Pulmonary Disease Model

This example illustrates the testing of inhibitors in a mouse model for treatment of lung disease: specifically, a model for idiopathic pulmonary fibrosis (IPF). It can be adapted mutatis mutandis to test and develop senolytic agents for use in clinical therapy.

As a model for chronic obstructive pulmonary disease (COPD), mice were exposed to cigarette smoke. The effect of a senolytic agent on the mice exposed to smoke is assessed by senescent cell clearance, lung function, and histopathology.

The mice used in this study include the 3MR strain, described in US 2017/0027139 A1 and in Demaria et al., Dev Cell. 2014 Dec. 22; 31(6): 722-733. The 3MR mouse has a transgene encoding thymidine kinase that converts the prodrug ganciclovir (GCV) to a compound that is lethal to cells. The enzyme in the transgene is placed under control of the p16 promoter, which causes it to be specifically expressed in senescent cells. Treatment of the mice with GCV eliminates senescent cells.

Other mice used in this study include the INK-ATTAC strain, described in US 2015/0296755 A1 and in Baker et al., Nature 2011 Nov. 2; 479(7372):232-236. The INK-ATTAC mouse has a transgene encoding switchable caspase 8 under control of the p16 promoter. The caspase 8 can be activated by treating the mice with the switch compound AP20187, whereupon the caspase 8 directly induces apoptosis in senescent cells, eliminating them from the mouse.

To conduct the experiment, six-week-old 3MR (n=35) or INK-ATTAC (n=35) mice were chronically exposed to cigarette smoke generated from a Teague TE-10 system, an automatically-controlled cigarette smoking machine that produces a combination of side-stream and mainstream cigarette smoke in a chamber, which is transported to a collecting and mixing chamber where varying amounts of air is mixed with the smoke mixture. The COPD protocol was adapted from the COPD core facility at Johns Hopkins University (Rangasamy et al., 2004, J. Clin. Invest. 114: 1248-1259; Yao et al., 2012, J. Clin. Invest. 122:2032-2045).

Mice received a total of 6 hours of cigarette smoke exposure per day, 5 days a week for 6 months. Each lighted cigarette (3R4F research cigarettes containing 10.9 mg of total particulate matter (TPM), 9.4 mg of tar, and 0.726 mg of nicotine, and 11.9 mg carbon monoxide per cigarette [University of Kentucky, Lexington, Ky.]) was puffed for 2 seconds and once every minute for a total of 8 puffs, with the flow rate of 1.05 L/min, to provide a standard puff of 35 $cm^3$. The smoke machine was adjusted to produce a mixture of side stream smoke (89%) and mainstream smoke (11%) by smoldering 2 cigarettes at one time. The smoke chamber atmosphere was monitored for total suspended particulates (80-120 mg/m3) and carbon monoxide (350 ppm).

Beginning at day 7, (10) INK-ATTAC and (10) 3MR mice were treated with AP20187 (3× per week) or ganciclovir (5 consecutive days of treatment followed by 16 days off drug, repeated until the end of the experiment), respectively. An equal number of mice received the corresponding vehicle. The remaining 30 mice (15 INK-ATTAC and 15 3MR) were evenly split with 5 of each genetically modified strain placed into three different treatment groups. One group (n=10) received Nutlin-3A (25 mg/kg dissolved in 10% DMSO/3% Tween-20™ in PBS, treated 14 days consecutively followed by 14 days off drug, repeated until the end of the experiment). One group (n=10) received ABT-263 (Navitoclax) (100 mg/kg dissolved in 15% DMSO/5% Tween-20, treated 7 days consecutively followed by 14 days off drug, repeated until the end of the experiment), and the last group (n=10) received only the vehicle used for ABT-263 (15% DMSO/ 5% Tween-20), following the same treatment regimen as ABT-263. An additional 70 animals that did not receive exposure to cigarette smoke were used as controls for the experiment.

After two months of cigarette smoke (CS) exposure, lung function was assessed by monitoring oxygen saturation using the MouseSTAT PhysioSuite™ pulse oximeter (Kent Scientific). Animals were anesthetized with isoflurane (1.5%) and the toe clip was applied. Mice were monitored for 30 seconds and the average peripheral capillary oxygen saturation ($SpO_2$) measurement over this duration was calculated.

Figure 6:
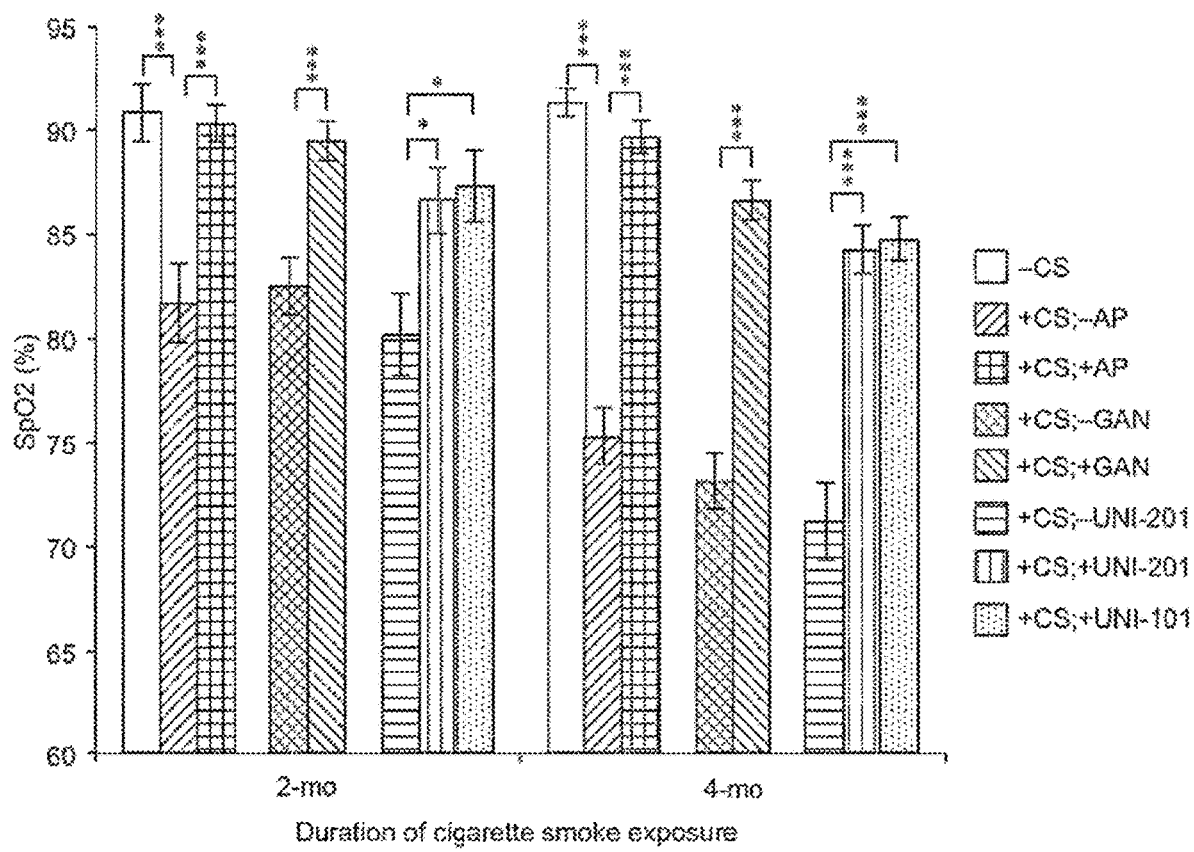
FIG. 6 shows that removing senescent cells with a senolytic agent helps restore oxygen saturation ($SPO_2$) in a mouse model for cigarette smoke (CS) induced COPD (chronic obstructive pulmonary disease).

FIG. 6 shows the results. Clearance of senescent cells via AP2018, ganciclovir, ABT-263 (Navitoclax) (201), or Nutlin-3A (101) resulted in statistically significant increases in $SpO_2$ levels in mice after two months of cigarette smoke exposure, compared with untreated controls.

Example 7: Efficacy of Senolytic Agents in Atherosclerosis when Administered Systemically This example illustrates the testing of an MDM2 inhibitor in a mouse model for treatment of atherosclerosis. The test compounds are administered systemically rather than locally. The model is done in an LDLR−/− strain of mice, which are deficient in the receptor for low-density lipoprotein. The experiments described here can be adapted mutatis mutandis to test and develop other types of inhibitors for use in clinical therapy.

Two groups of LDLR−/− mice (10 weeks) are fed a high fat diet (HFD) (Harlan Teklad TD.88137) having 42% calories from fat, beginning at Week 0 and throughout the study. Two groups of LDLR−/− mice (10 weeks) are fed normal chow (−HFD). From weeks 0-2, one group of HFD mice and −HFD mice are treated with Nutlin-3A (25 mg/kg, intraperitoneally). One treatment cycle is 14 days treatment, 14 days off. Vehicle is administered to one group of HFD mice and one group of −HFD mice. At week 4 (timepoint 1), one group of mice are sacrificed and to assess presence of senescent cells in the plaques. For the some of the remaining mice, Nutlin-3A and vehicle administration is repeated from weeks 4-6. At week 8 (timepoint 2), the mice are sacrificed and to assess presence of senescent cells in the plaques. The remaining mice are treated with Nutlin-3A or vehicle from weeks 8-10. At week 12 (timepoint 3), the mice are sacrificed and to assess the level of plaque and the number of senescent cells in the plaques.

Plasma lipid levels were measured in LDLR−/− mice fed a HFD and treated with Nutlin-3A or vehicle at timepoint 1 as compared with mice fed a −HFD (n=3 per group). Plasma was collected mid-afternoon and analyzed for circulating lipids and lipoproteins.

At the end of timepoint 1, LDLR−/− mice fed a HFD and treated with Nutlin-3A or vehicle were sacrificed (n=3, all groups), and the aortic arches were dissected for RT-PCR analysis of SASP factors and senescent cell markers. Values were normalized to GAPDH and expressed as fold-change versus age-matched, vehicle-treated LDLR−/− mice on a normal diet. The data show that clearance of senescent cells with Nutlin-3A in LDLR−/− mice fed a HFD reduced expression of several SASP factors and senescent cell markers, MMP3, MMP13, PAI1, p21, IGFBP2, IL-1A, and IL-1B after one treatment cycle.

At the end of timepoint 2, LDLR−/− mice fed a HFD and treated with Nutlin-3A or vehicle (n=3 for all groups) were sacrificed, and aortic arches were dissected for RT-PCR analysis of SASP factors and senescent cell markers. Values were normalized to GAPDH and expressed as fold-change versus age-matched, vehicle-treated LDLR−/− mice on a normal diet. The data show expression of some SASP factors and senescent cell markers in the aortic arch within HFD mice. Clearance of senescent cells with multiple treatment cycles of Nutlin-3A in LDLR−/− mice fed a HFD reduced expression of most markers.

At the end of timepoint 3, LDLR−/− mice fed a HFD and treated with Nutlin-3A or vehicle (n=3 for all groups) were sacrificed, and aortas were dissected and stained with Sudan IV to detect the presence of lipid. Body composition of the mice was analyzed by MRI, and circulating blood cells were counted by Hemavet™.

FIG. 7 shows the results. Treatment with Nutlin-3A reduced the surface area covered by plaques in the descending aorta by about 45%. The platelet and lymphocyte counts were equivalent between the Nutlin-3A and vehicle treated mice. Treatment with Nutlin-3A also decreased mass and body fat composition in mice fed the high fat diet.

Example 8: Measuring Cytotoxicity for Cancer Cells In Vitro and In Vivo

New proteasome inhibitors may be developed not only for treating conditions mediated by senescent cells, but also conditions mediated by cancer cells.

The ability of compounds to specifically kill cancer cells can be tested in assays using other established cell lines. These include HeLa cells, OVCAR-3, LNCaP, and any of the Authenticated Cancer Cell Lines available from Millipore Sigma, Burlington Mass., U.S.A. Compounds specifically kill cancer cells if they are lethal to the cells at a concentration that is at least 5-fold lower, and preferably 25- or 100-fold lower than a non-cancerous cell of the same tissue type. The control cell has morphologic features and cell surface markers similar to the cancer cell line being tested, but without signs of cancer.

In vivo, compounds are evaluated in flank xenograft models established from sensitive SCLC (H889) and hematologic (RS4; 11) cell lines, or using other tumor-forming cancer cell lines, according to what type of cancer is of particular interest to the user. When dosed orally or intravenously, compounds induce rapid and complete tumor responses (CR) that are durable for several weeks after the end of treatment in all animals bearing H889 (SCLC) or RS4; 11 (ALL) tumors. Similar treatment of mice bearing H146 SCLC tumors can induce rapid regressions in the animals.

Exemplary Compounds and their Use

Some of the proteasome inhibitors that illustrate this invention and their use are set forth in the following clauses.

Clause 1. A compound according to Formula (I) that inhibits proteasome activity:

$$R^0-X-(A)_n-Z \quad\quad\quad (I)$$

wherein;

$R^0$ is selected from H, alkyl, substituted alkyl, alkanoyl, substituted alkanoyl, alkylaminocarbonyl, substituted alkylaminocarbonyl, alkoxycarbonyl, substituted alkoxycarbonyl, alkylaminothiocarbonyl, substituted alkylaminothiocarbonyl, alkoxythiocarbonyl, substituted alkoxythiocarbonyl and promoiety;

$(A)_n$ is a sequence of n peptidic units $A^1$ to $A^n$, each independently selected from amino acid residues and peptidomimetic units, wherein:

n is 2-7;

the $A^1$ unit comprises a first terminal group X, wherein X is O or S; and the $A^n$ unit comprises a second terminal group Z; and Z is a proteasome-reactive electrophilic group.

Clause 2. The proteasome inhibitor compound of clause 1, wherein the compound is of Formula (Ia):

$$R^0-X-A^1-A^2-A^3-A^4-Z \quad\quad\quad (Ia)$$

wherein:

n is 4; and $A^1$ to $A^4$ are independently selected from amino acid residues (e.g., α-amino acids, β-amino acids, D-amino acids) and peptidomimetic units (for example, retroinverso peptide units, peptoid units, hydroxyethylamine isosteric units, as described herein), wherein the $A^4$ unit comprises a modified terminal comprising Z.

Clause 3. The proteasome inhibitor compound of clause 1 or 2, wherein the compound is of Formula (II):

$$R^0-X-B^1-L^1-B^2-L^2-B^3-L^3-B^4-L^4-Z \quad\quad\quad (II)$$

with substituents $R^1$, $R^2$, $R^3$, $R^4$ wherein:
B¹ to B⁴ are each independently a branching group selected from CH, CR" and N, wherein R" is $C_{(1-6)}$alkyl or substituted $C_{(1-6)}$alkyl;
L¹ to L⁴ are each independently a linking group (e.g., a group having a backbone of 1-3 atoms); and
R¹ to R⁴ are independently selected from alkyl, substituted alkyl, aralkyl, substituted aralkyl, heteroarylalkyl and substituted heteroarylalkyl.

Clause 4. The proteasome inhibitor compound of clause 3, wherein L¹ to L⁴ are each independently selected from —CONR'—, —CH₂NR'—, —CH(OH)NR'—, —CH₂CONR'—, —CO—, —CH₂CO—, —COCH₂—, —CO₂—, —CH₂O—, —CH₂S—, —CH₂CH₂—, —CH=CH— and —NR'CO—, wherein R' is H, $C_{(1-6)}$alkyl or substituted $C_{(1-6)}$alkyl (e.g., methyl).

Clause 5. The proteasome inhibitor compound of clause 3 or 4, wherein at least one —B"(R")-L"- group of formula (II) is selected from the following groups:

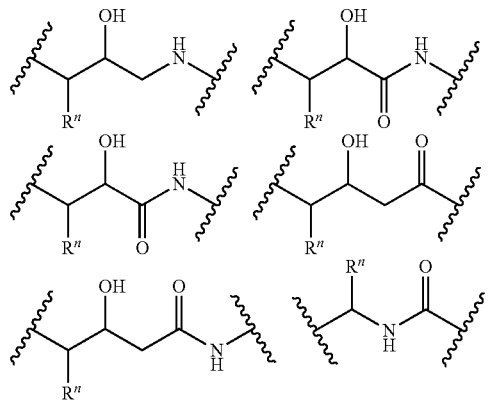

-continued

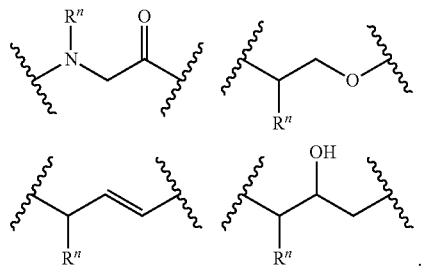

Clause 6. The proteasome inhibitor compound of any one of clauses 3-5, wherein the compound is of one of Formulas (IIIa) to (IIIc):

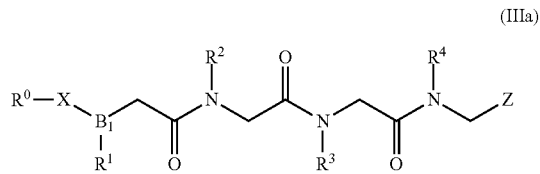
(IIIa)

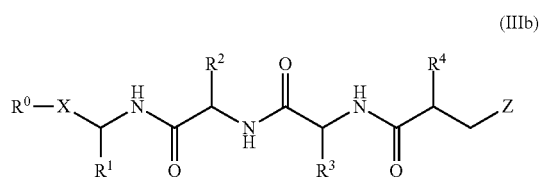
(IIIb)

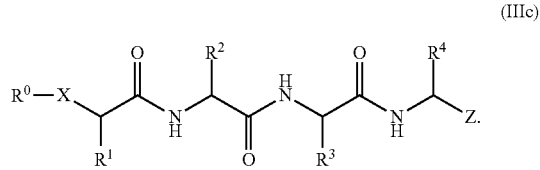
(IIIc)

Clause 7. The proteasome inhibitor compound of any one of clauses 1-6, wherein Z is selected from aldehyde, epoxyketone, aziridinylketone, boronate, boronate ester and beta-lactone.

Clause 8. The proteasome inhibitor compound of any one of clauses 3-7, wherein R¹ to R⁴ are selected from one of the following combinations #1-6:

| # | R¹ | R² | R³ | R⁴ |
|---|-----|-----|-----|-----|
| 1 | phenyl-$C_{(1-6)}$alkyl, cycloalkyl-$C_{(1-6)}$alkyl or $C_{(1-6)}$alkyl | CH₂CH(CH₃)₂ | CH₂Ph | CH₂CH(CH₃)₂ |
| 2 | CH₂Ph | $C_{(1-6)}$alkoxy-$C_{(1-6)}$alkyl, $C_{(1-6)}$alkyl or $C_{(1-6)}$hydroxyalkyl | CH₂Ph | CH₂CH(CH₃)₂ |
| 3 | CH₂CH₂Ph | CH₂CH(CH₃)₂ | | CH₂CH(CH₃)₂ |
| 4 | CH₂CH₂Ph | CH₂CH(CH₃)₂ | CH₂Ph | $C_{(1-6)}$alkyl |
| 5 | CH₂CH₂Ph | $C_{(1-6)}$alkoxy-$C_{(1-6)}$alkyl, $C_{(1-6)}$alkyl or $C_{(1-6)}$hydroxyalkyl | CH₂Ph | $C_{(1-6)}$alkyl |
| 6 | CH₂CH₂Ph | CH₂CH(CH₃)₂ | CH₂Ph | CH₂CH(CH₃)₂ |

Clause 9. The proteasome inhibitor compound of any of clauses 1 to 8, wherein:

X is O or S;

R⁰— is R¹⁰— or R¹⁰-Q-;

Q is selected from ethylene glycol, polyethylene glycol, —C(=O)—, —NR¹¹C(=O)—, —OC(=O)—, —C(=S)—, —NR¹¹C(=S)—, —OC(=S)— and —OC(=S)—; and R¹⁰ and R¹¹ are independently selected from H, alkyl and substituted alkyl.

Clause 10. The proteasome inhibitor compound of clause 9, wherein R⁰ is selected from the following structures:

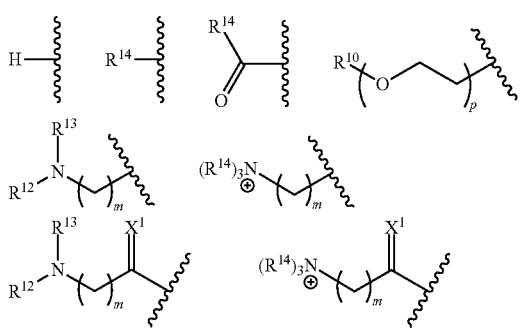

wherein:
m is an integer from 1 to 6;
p is an integer from 1 to 30;
$X^1$ is selected from O, S and $NR^{14}$; and
$R^{12}$ and $R^{13}$ are independently selected from H, alkyl and substituted alkyl, or $R^{12}$ and $R^{13}$ are cyclically linked and together with the nitrogen atom to which they are attached provide a heterocycle ring that is optionally further substituted; and
each $R^{14}$ is independently selected from H, $C_{(1-6)}$alkyl and substituted $C_{(1-6)}$alkyl.

Clause 11. A compound according to Formula (IV) that inhibits proteasome activity:

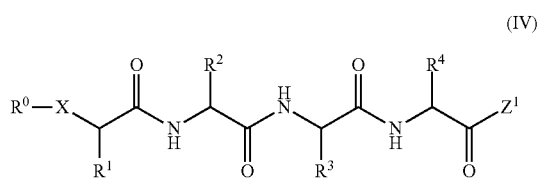

(IV)

wherein:
$R^2$ to $R^4$ are independently selected from alkyl, substituted alkyl, aralkyl, substituted aralkyl, heteroarylalkyl and substituted heteroarylalkyl; and
$Z^1$ is epoxide group or aziridine group.

Clause 12. The proteasome inhibitor compound of clause 11, having the structure shown in Formula (V):

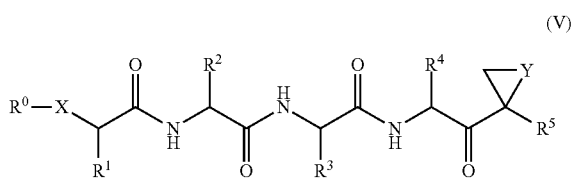

(V)

wherein:
Y is selected from O and $NR^{15}$; and
$R^5$ and $R^{15}$ are independently selected from H, $C_{(1-6)}$alkyl and substituted $C_{(1-6)}$alkyl.

Clause 13. The proteasome inhibitor compound of any one of clauses 11 to 12, wherein $R^1$ to $R^4$ are independently selected from $C_{(1-6)}$alkyl, substituted $C_{(1-6)}$alkyl, $C_{(1-6)}$hydroxyalkyl, substituted $C_{(1-6)}$hydroxyalkyl, $C_{(1-6)}$alkoxy-$C_{(1-6)}$alkyl, substituted $C_{(1-6)}$alkoxy-$C_{(1-6)}$alkyl, aryl-$C_{(1-6)}$alkyl, substituted aryl-$C_{(1-6)}$alkyl, heteroaryl-$C_{(1-6)}$alkyl, substituted heteroaryl-$C_{(1-6)}$alkyl, cycloalkyl-$C_{(1-6)}$alkyl, substituted cycloalkyl-$C_{(1-6)}$alkyl, heterocycle-$C_{(1-6)}$alkyl and substituted heterocycle-$C_{(1-6)}$alkyl.

Clause 14. The proteasome inhibitor compound of any one of clauses 11 to 12, wherein:
$R^1$ is selected from $C_{(1-6)}$alkyl, aryl-$C_{(1-6)}$alkyl, substituted aryl-$C_{(1-6)}$alkyl, cycloalkyl-$C_{(1-6)}$alkyl and substituted cycloalkyl-$C_{(1-6)}$alkyl;
$R^2$ and $R^4$ are selected from $C_{(1-6)}$alkyl, substituted $C_{(1-6)}$alkyl, $C_{(1-6)}$alkoxy-$C_{(1-6)}$alkyl, substituted $C_{(1-6)}$alkoxy-$C_{(1-6)}$alkyl, $C_{(1-6)}$hydroxyalkyl and substituted $C_{(1-6)}$hydroxyalkyl; and
$R^3$ is selected from aryl-$C_{(1-6)}$alkyl, substituted aryl-$C_{(1-6)}$alkyl, $C_{(1-6)}$alkoxy-$C_{(1-6)}$alkyl and substituted $C_{(1-6)}$alkoxy-$C_{(1-6)}$alkyl.

Clause 15. The proteasome inhibitor compound of any one of clauses 11 to 12, wherein:
$R^1$ is selected from phenyl-$C_{(1-6)}$alkyl, cycloalkyl-$C_{(1-6)}$alkyl and $C_{(1-6)}$alkyl;
$R^2$ is selected from $C_{(1-6)}$alkoxy-$C_{(1-6)}$alkyl, $C_{(1-6)}$alkyl and $C_{(1-6)}$hydroxyalkyl;
$R^3$ is selected from phenyl-$C_{(1-6)}$alkyl, cycloalkyl-$C_{(1-6)}$alkyl, $C_{(1-6)}$alkoxy-$C_{(1-6)}$alkyl and $C_{(1-6)}$hydroxyalkyl; and
$R^4$ is $C_{(1-6)}$alkyl.

Clause 16. The proteasome inhibitor compound of any one of clauses 11 to 12, wherein:
$R^1$ is selected from phenylethyl, cyclopropyl-methyl and propyl;
$R^2$ is selected from methoxymethyl, isobutyl and 1-hydroxy-ethyl;
$R^3$ is selected from phenylmethyl, cyclopropyl-methyl, methoxymethyl and 1-hydroxy-ethyl; and
$R^4$ is isobutyl.

Clause 17. The proteasome inhibitor compound of any of clauses 11 to 16, having the stereochemistry shown in Formula (VI):

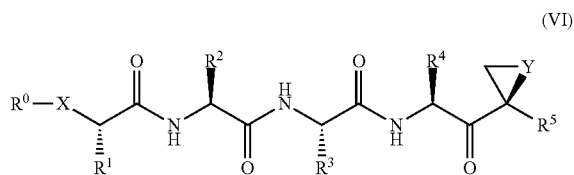

(VI)

Clause 18. The proteasome inhibitor compound of clause 17, selected from the following Formulas (VIa)-(VId):

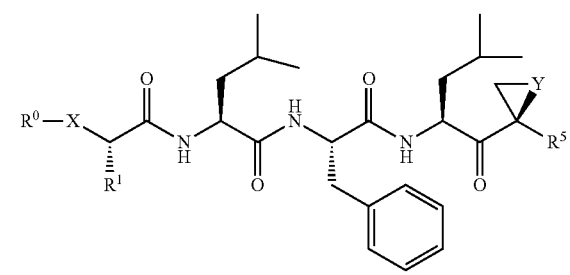

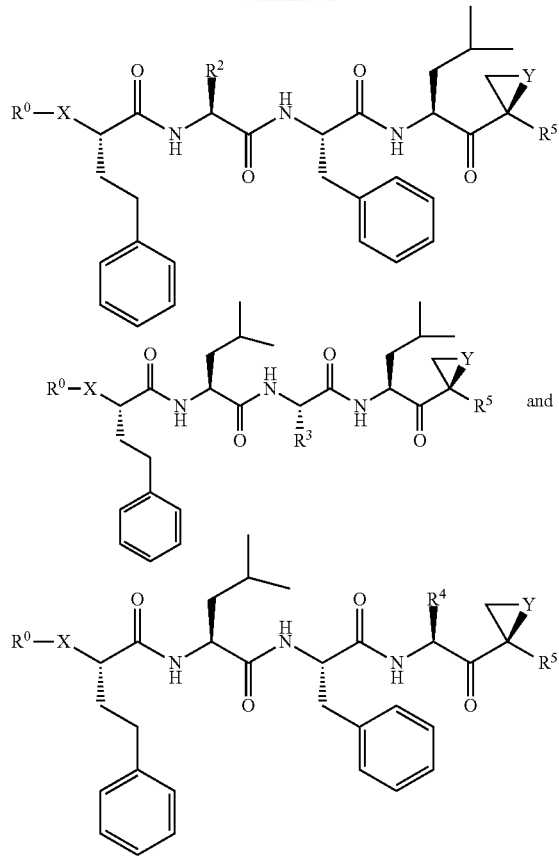

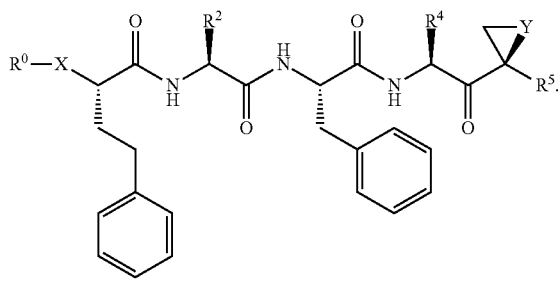

Clause 19. The proteasome inhibitor compound of clause 17, having the structure shown in Formula (VIe):

(VIe)

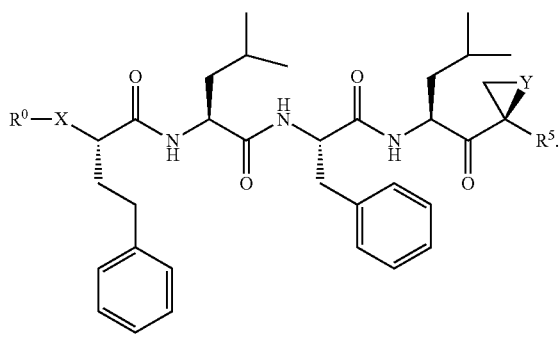

Clause 20. The proteasome inhibitor compound of clause 17, having the structure shown in Formula (VIf):

(VIf)

Clause 21. The proteasome inhibitor compound of any of clauses 17 to 20, wherein Y is O and R5 is methyl.

Clause 22. The proteasome inhibitor compound of any of clauses 17 to 20, wherein X is O or S.

Clause 23. The proteasome inhibitor compound of any of clauses 11 to 22, wherein:

X is O or S;

$R^0$— is $R^{10}$— or $R^{10}$-Q-;

Q is selected from ethylene glycol, polyethylene glycol, —C(=O)—, —NR$^{11}$C(=O)—, —OC(=O)—, —C(=S)—, —NR$^{11}$C(=S)—, —OC(=S)— and —OC(=S)—; and $R^{10}$ and $R^{11}$ are independently selected from H, alkyl and substituted alkyl.

Clause 24. The proteasome inhibitor compound of clause 23, wherein $R^0$ is selected from the following structures:

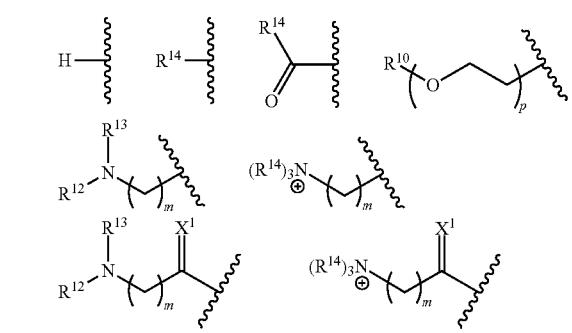

wherein:

m is an integer from 1 to 6;

p is an integer from 1 to 30;

$X^1$ is selected from 0, S and NR$^{14}$; and $R^{12}$ and $R^{13}$ are independently selected from H, alkyl and substituted alkyl, or $R^{12}$ and $R^{13}$ are cyclically linked and together with the nitrogen atom to which they are attached provide a heterocycle ring that is optionally further substituted; and each $R^{14}$ is independently selected from H, $C_{(1-6)}$alkyl and substituted $C_{(1-6)}$alkyl.

Clause 25. The proteasome inhibitor compound of clause 23, wherein $R^0$ is selected from the following structures:

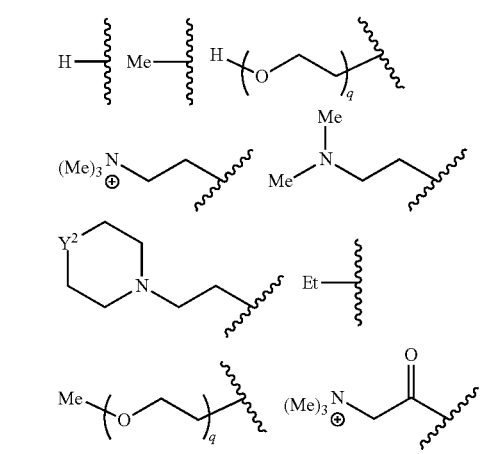

-continued

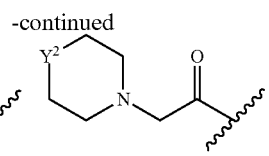
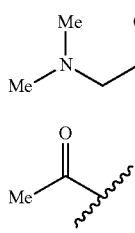

wherein:
q is an integer from 1 to 3 (e.g., q is 3);
$Y^2$ is selected from O and $NR^{15}$ (e.g., $Y^2$ is O); and
$R^{15}$ is selected from H, $C_{(1-6)}$alkyl and substituted $C_{(1-6)}$ alkyl.

Clause 26. The proteasome inhibitor compound of clause 25, wherein q is 3; and $Y^2$ is O.

Clause 27. The proteasome inhibitor compound according to any of clauses 1 to 26, which has an $EC_{50}$ for irradiated IMR90 cells of less than 0.1 µM (100 nM).

Clause 28. The proteasome inhibitor compound according to any of clauses 1 to 27, which has a $EC_{50}$ for senescent cells that is at least 10-fold higher than its $EC_{50}$ for non-senescent cells of the same cell type.

Clause 30. The proteasome inhibitor compound of clause 1, selected from the compounds shown in FIGS. 1A and 1B.

Clause 31. A proteasome inhibitor according to any of clauses 1 to 30, for use in the selective removal of senescent cells from a mixed cell population or tissue, or for use in treatment of a senescence associated condition that is caused or mediated at least in part by senescent cells.

Clause 32. A proteasome inhibitor according to any of clauses 1 to 30, for use in the selective removal of cancer cells, or for use in treatment of cancer.

Clause 33. A method of selectively removing senescent cells from a cell population or tissue, comprising selectively inhibiting activity of proteasome in the cell.

Clause 34. A method of modulating or eliminating a senescent cell from a cell population or tissue, comprising contacting the senescent cell with a means for inhibiting activity of proteasome.

Clause 35. The method of clause 33 or 34, wherein the proteasome inhibitor is a compound according to any of clauses 1 to 30.

Clause 36. The method of clause 33 or 34, wherein the proteasome inhibitor is a compound selected from the structures shown in FIGS. 1A, 1B, and 1C.

Clause 37. A method of treating a senescence related condition in a tissue in a subject,
wherein the senescence related condition a condition that is caused or mediated at least in part by senescent cells in the tissue, or is characterized as having an overabundance of senescent cells in or around the tissue, in comparison with unaffected tissue,
wherein the method comprises administering to the tissue an effective amount of a means for inhibiting activity of proteasome, thereby selectively removing senescent cells from the tissue and relieving at least one sign or symptom of the condition in the subject.

Clause 38. A unit dose of a pharmaceutical composition that contains an amount of a compound that inhibits activity of proteasome, configured for use in the treatment of a senescence associated condition that is caused or mediated at least in part by senescent cells,
wherein the composition contains a formulation of the compound configured for administration to a tissue in a subject that manifests the condition,
wherein the formulation of the composition and the amount of the compound in the unit dose configure the unit dose to be effective in selectively removing senescent cells in or around the tissue in the subject, thereby decreasing the severity of one or more signs or symptoms of the condition without causing adverse effects in the subject when administered to the tissue as a single dose.

Clause 39. The product or method of clause 37 or 38, wherein the proteasome inhibitor is an inhibitor according to any of clauses 1 to 30.

Clause 40. The product or method of clause 37 or 38, wherein the proteasome inhibitor is an inhibitor selected from the structures shown in FIGS. 1A, 1B, and 1C.

Clause 41. The product or method of any of clauses 37 to 40, wherein the condition is osteoarthritis.

Clause 42. The product or method of any of clauses 37 to 40, wherein the condition is an ophthalmic condition.

Clause 43. The product or method of clause 42, wherein the ophthalmic condition is selected from wet and dry age-related macular degeneration (AMD), diabetic retinopathy, and glaucoma.

Clause 44. The product or method of any of clauses 37 to 40, wherein the condition is a pulmonary condition.

Clause 45. The product or method of clause 44, wherein the pulmonary condition is selected from chronic obstructive pulmonary disease (COPD) and idiopathic pulmonary fibrosis (IPF).

Clause 46. The product or method of any of clauses 37 to 40, wherein the condition is atherosclerosis.

The several hypotheses presented in this disclosure provide a premise by way of which the reader may understand the invention. This premise is provided for the intellectual enrichment of the reader. Practice of the invention does not require detailed understanding or application of the hypothesis. Except where stated otherwise, features of the hypothesis presented in this disclosure do not limit application or practice of the claimed invention.

For example, except where the elimination of senescent cells is explicitly required, the compounds may be used for treating the conditions described regardless of their effect on senescent cells. Although many of the senescence-related conditions referred to in this disclosure occur predominantly in older patients, the occurrence of senescent cells and the pathophysiology they mediate can result from other events, such as irradiation, other types of tissue damage, other types of disease, genetic abnormalities, and invention. The invention may be practiced on patients of any age having the condition indicated, unless otherwise explicitly indicated or required.

Discussions about the mechanism of action of the peptide-based compounds of the invention are also provided for the intellectual enrichment of the reader. Except where stated otherwise, the compounds may be used for removing senescent or cancer cells or for the treatment of disease conditions as claimed below, regardless of how they operate inside the target cells or in the treated subject.

Although the compounds and compositions referred to in this disclosure are illustrated in the context of eliminating senescent cells and treating senescence-associated conditions, compounds and their derivatives described herein that are novel can be prepared for any purpose, including but not limited to laboratory use, the treatment of senescence-related conditions, the poisoning of in-laws, and the treatment of other conditions such as cancer.

While the invention has been described with reference to the specific examples and illustrations, changes can be made and equivalents can be substituted to adapt to a particular context or intended use as a matter of routine development and optimization and within the purview of one of ordinary skill in the art, thereby achieving benefits of the invention without departing from the scope of what is claimed and their equivalents.

The invention claimed is:

1. A compound according to Formula (V):

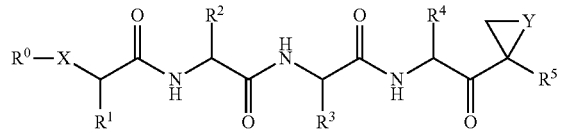

(V)

wherein:
R$^0$ is selected from H, alkyl, substituted alkyl, alkanoyl, substituted alkanoyl, alkylaminocarbonyl, substituted alkylaminocarbonyl, alkoxycarbonyl, substituted alkoxycarbonyl, alkylaminothiocarbonyl, substituted alkylaminothiocarbonyl, alkoxythiocarbonyl, substituted alkoxythiocarbonyl and promoiety;

X is O or S;

R$^1$ to R$^4$ are independently selected from alkyl, substituted alkyl, aralkyl, substituted aralkyl, heteroarylalkyl and substituted heteroarylalkyl;

Y is selected from O and NR$^{15}$; and

R$^5$ and R$^{15}$ are independently selected from H, C$_{(1-6)}$alkyl and substituted C$_{(1-6)}$alkyl.

2. The compound of claim 1, wherein:
R$^1$ is selected from C$_{(1-6)}$alkyl, aryl-C$_{(1-6)}$alkyl, substituted aryl-C$_{(1-6)}$alkyl, cycloalkyl-C$_{(1-6)}$alkyl and substituted cycloalkyl-C$_{(1-6)}$alkyl;

R$^2$ and R$^4$ are selected from C$_{(1-6)}$alkyl, substituted C$_{(1-6)}$alkyl, C$_{(1-6)}$alkoxy-C$_{(1-6)}$alkyl, substituted C$_{(1-6)}$alkoxy-C$_{(1-6)}$alkyl, C$_{(1-6)}$hydroxyalkyl and substituted C$_{(1-6)}$hydroxyalkyl; and R$^3$ is selected from aryl-C$_{(1-6)}$alkyl, substituted aryl-C$_{(1-6)}$alkyl, C$_{(1-6)}$alkoxy-C$_{(1-6)}$alkyl and substituted C$_{(1-6)}$alkoxy-C$_{(1-6)}$alkyl.

3. The compound of claim 1, wherein;
R$^1$ is selected from phenylethyl, cyclopropyl-methyl and propyl;

R$^2$ is selected from methoxymethyl, isobutyl and 1-hydroxy-ethyl;

R$^3$ is selected from phenylmethyl, cyclopropyl-methyl, methoxymethyl and 1-hydroxy-ethyl; and R$^4$ is isobutyl.

4. The compound of claim 1, selected from the following:

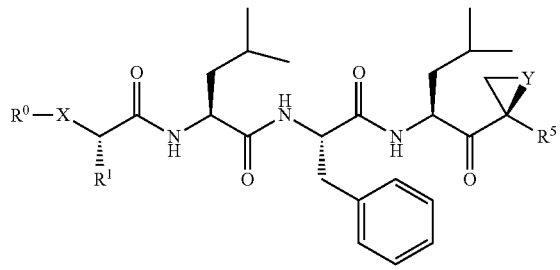

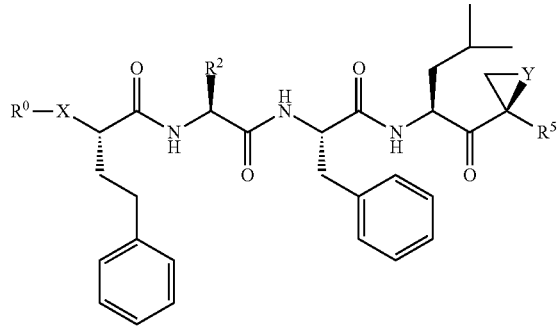

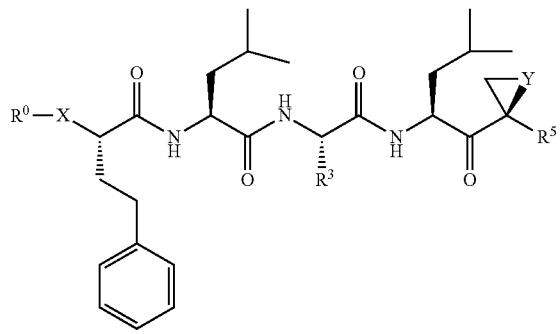

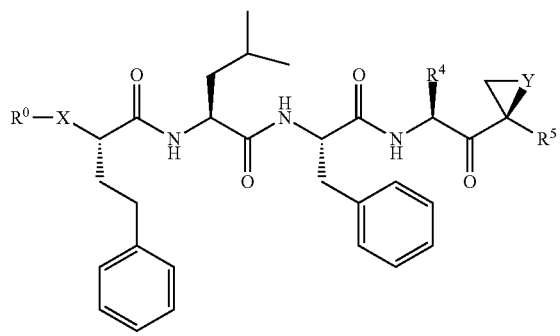

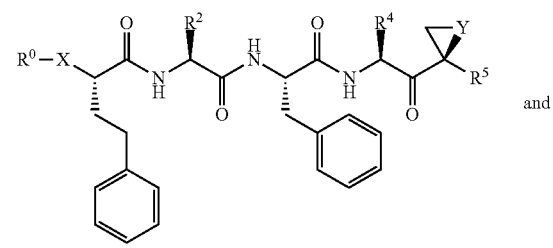

and

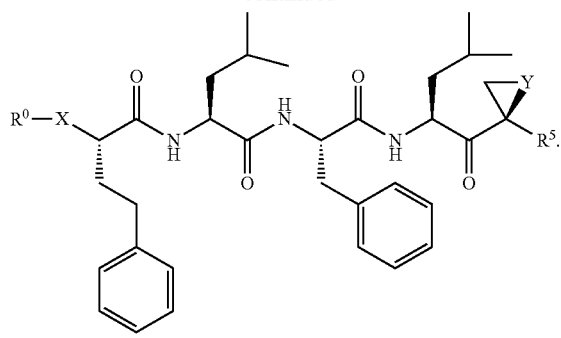

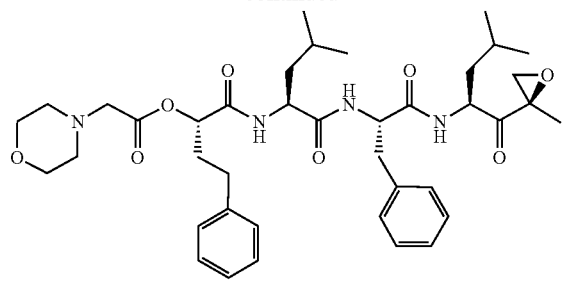

5. The compound of claim 1, wherein:
Y is O, $R^5$ is methyl; and
X is O.

6. The compound of claim 1, wherein:
X is O or S;
$R^0$ is $R^{10}$— or $R^{10}$-Q-;
Q is selected from ethylene glycol, polyethylene glycol, —C(=O)—, —NR$^{11}$C(=O)—, —OC(=O)—, —C(=S)—, —NR11C(=S)—, —OC(=S)— and —OC(=S)—; and
$R^{10}$ and $R^{11}$ are independently selected from H, alkyl and substituted alkyl.

7. The compound of claim 1, which has proteasome inhibition activity (IC$_{50}$) that is less than 1.0 μM.

8. The compound of claim 1, which has senolytic activity (EC$_{50}$) for IMR90 fibroblasts that is less than 1 μM and a selectivity index (SI) of 2 or more.

9. The compound of claim 1, selected from the following:

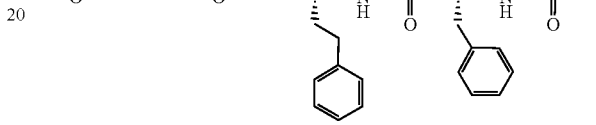

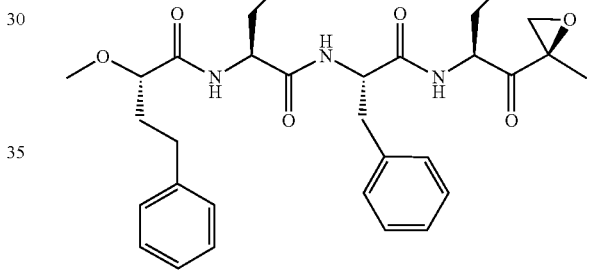

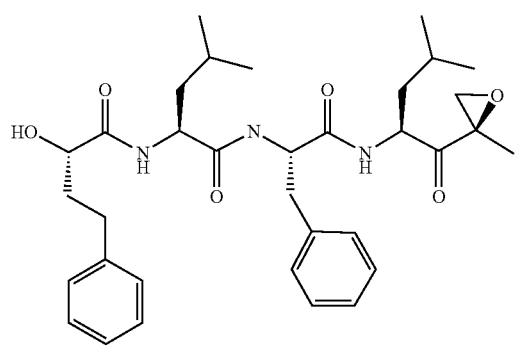

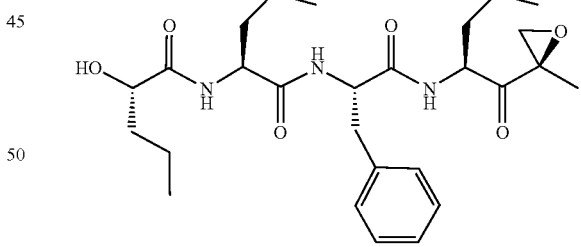

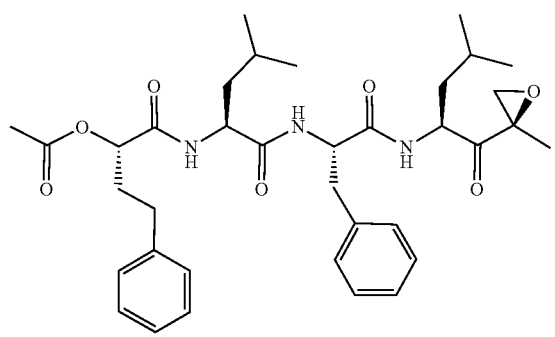

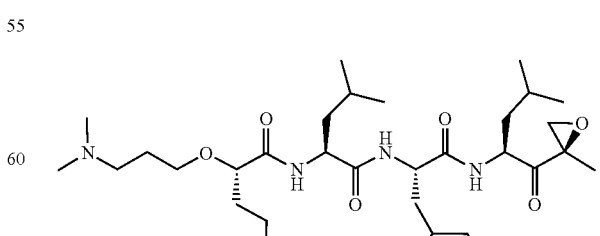

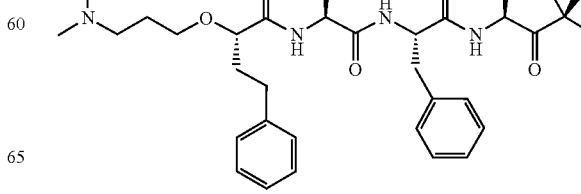

47
-continued
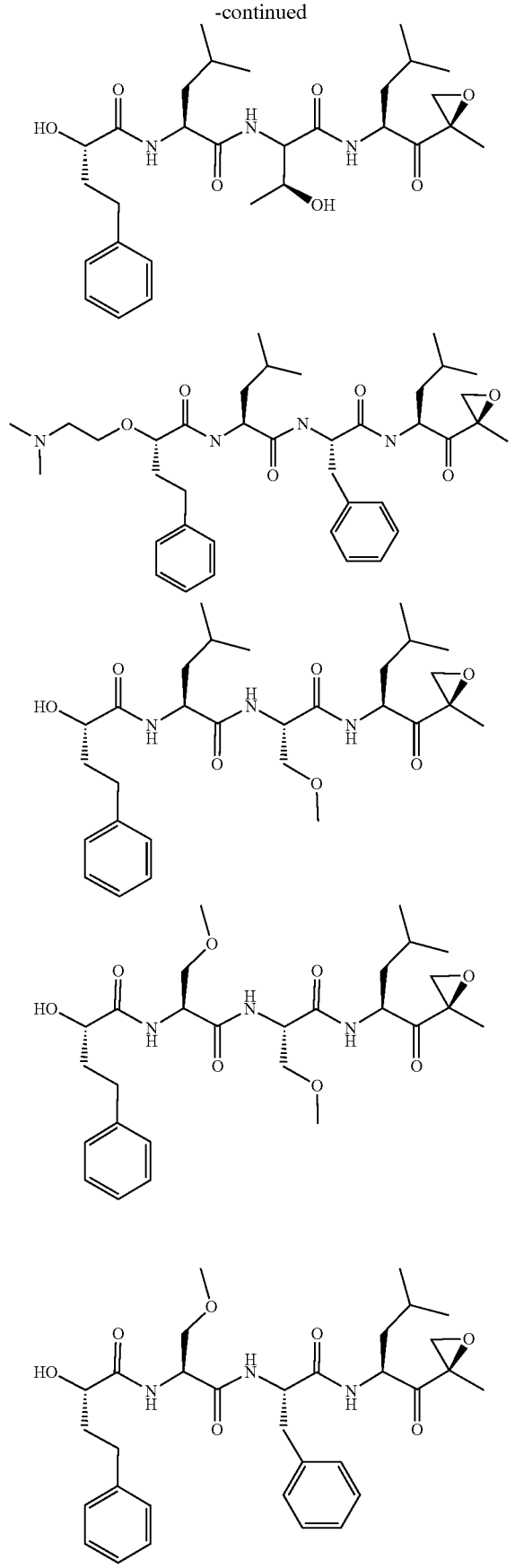
48
-continued
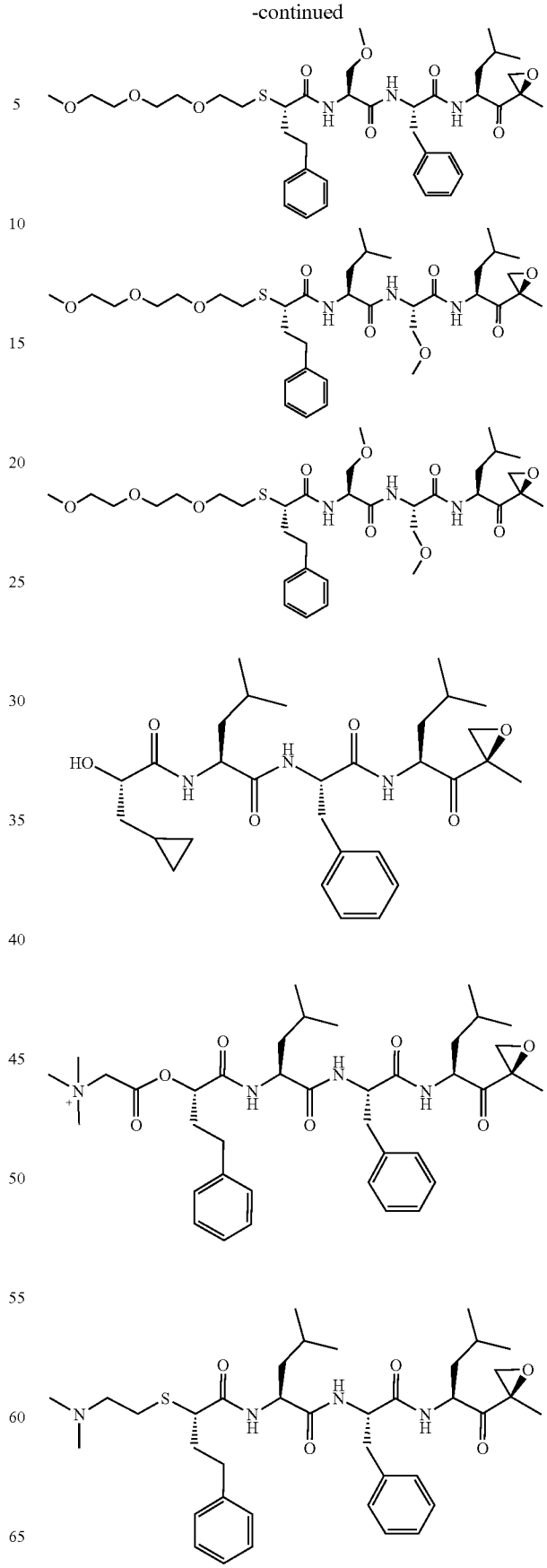

49
-continued
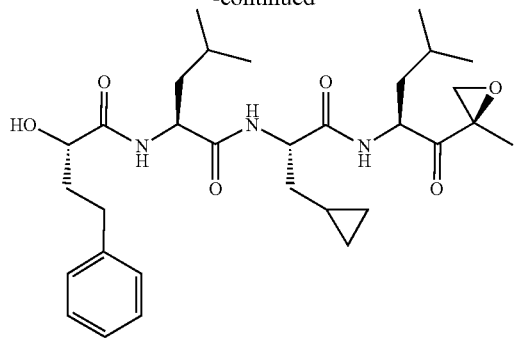
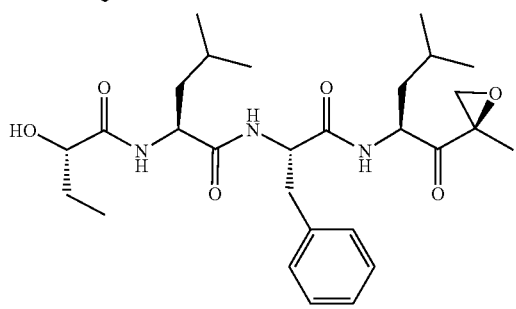
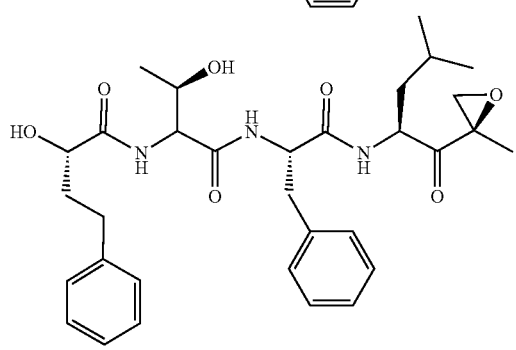
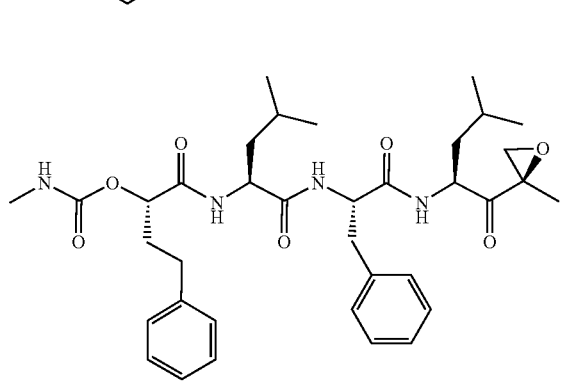
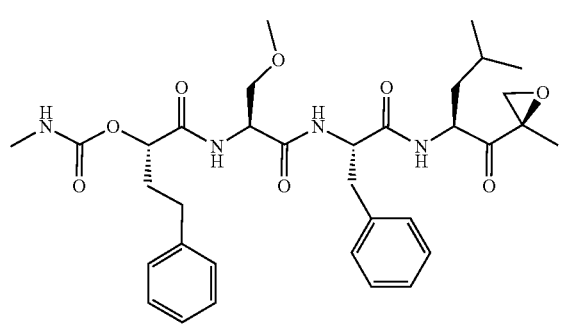
50
-continued
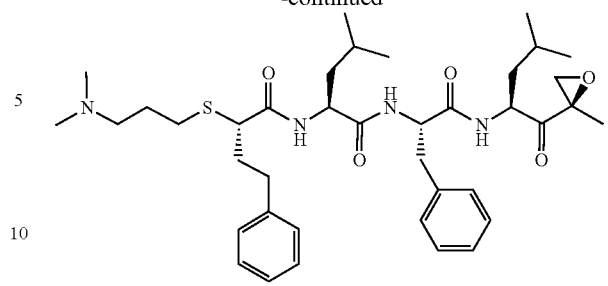
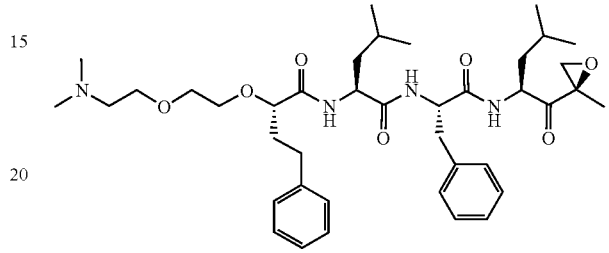
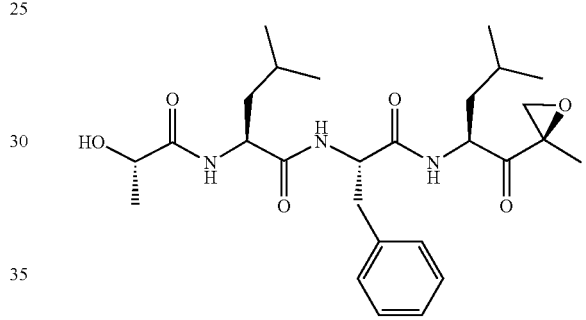
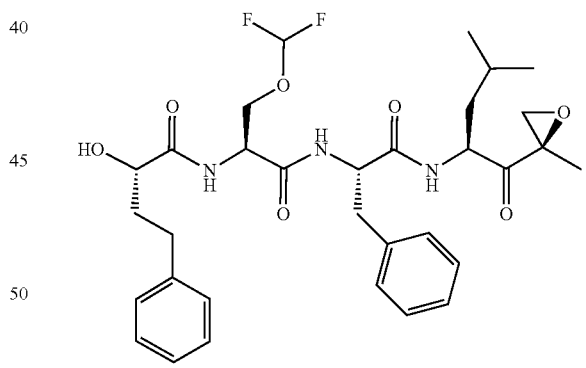
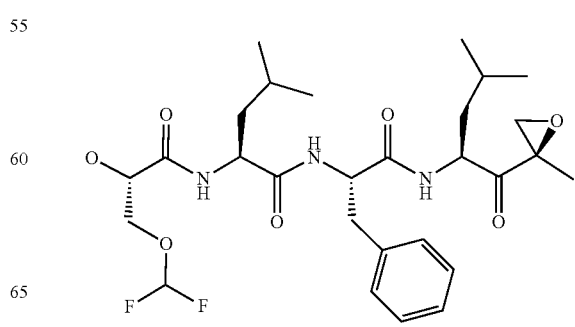

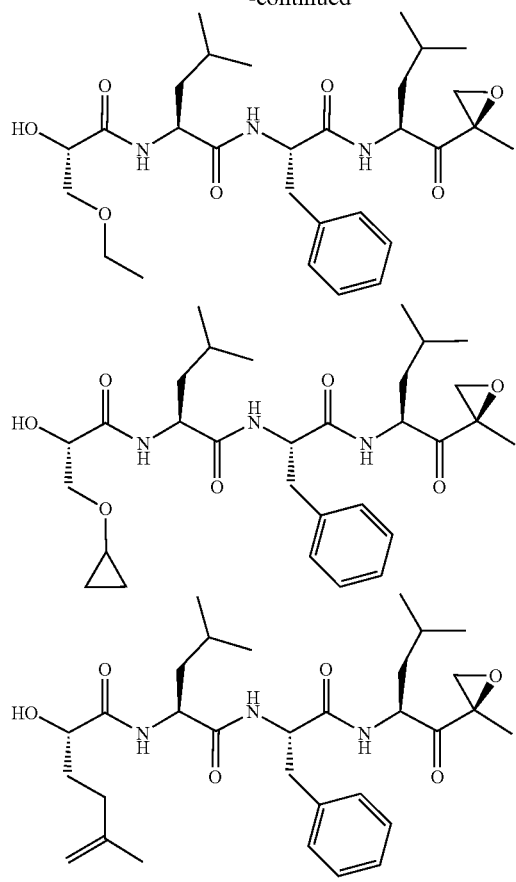
and
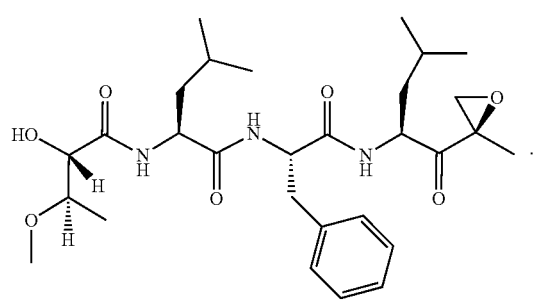
10. The compound of claim 1, selected from the following:
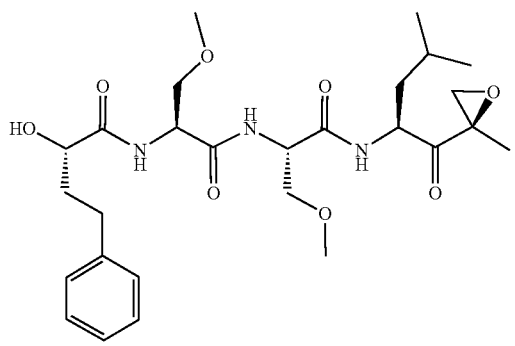
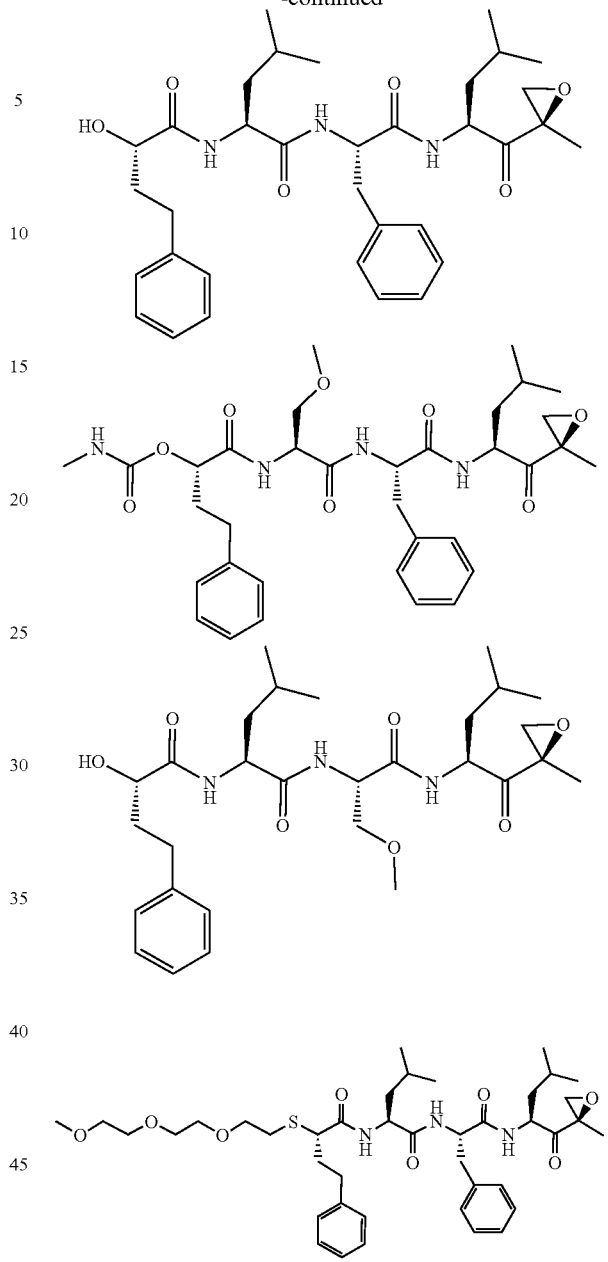
and
* * * * *

UNITED STATES PATENT AND TRADEMARK OFFICE
CERTIFICATE OF CORRECTION

PATENT NO. : 10,689,416 B2
APPLICATION NO. : 16/393651
DATED : June 23, 2020
INVENTOR(S) : Ryan Hudson It is certified that error appears in the above-identified patent and that said Letters Patent is hereby corrected as shown below:

In the Specification

At Column 35, Line 25, the recitation of " 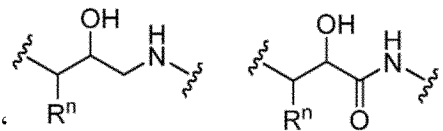 " should read 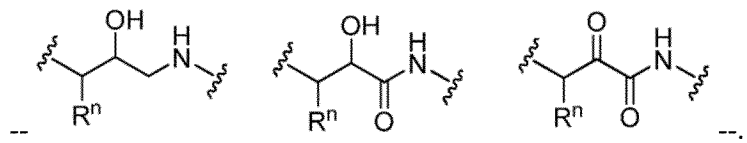 --.

In the Claims

At Column 45, Line 45, Claim 9, the recitation of " 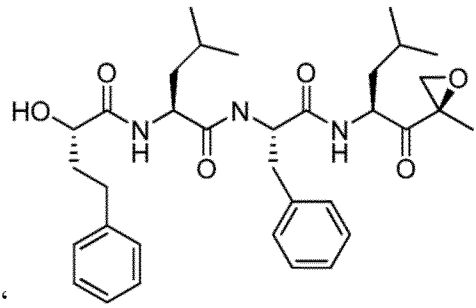 " should

Signed and Sealed this
Eighteenth Day of August, 2020

Andrei Iancu
*Director of the United States Patent and Trademark Office*

CERTIFICATE OF CORRECTION (continued)
U.S. Pat. No. 10,689,416 B2 read -- 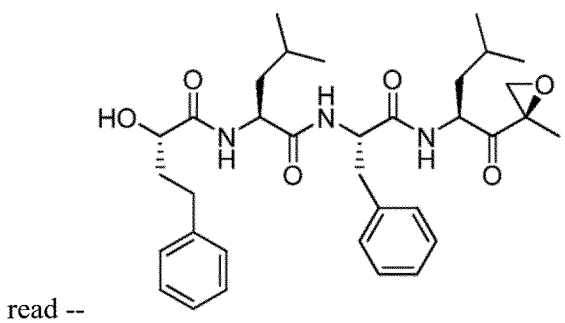 --.

At Column 47, Line 20, Claim 9, the recitation of " 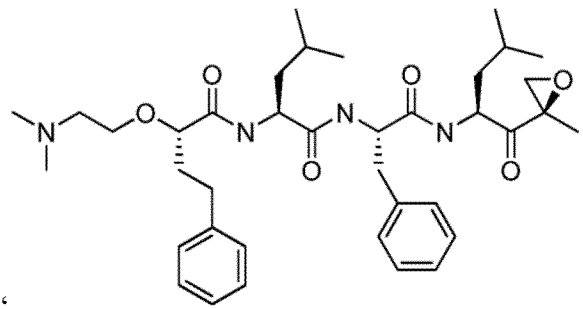 "

should read -- 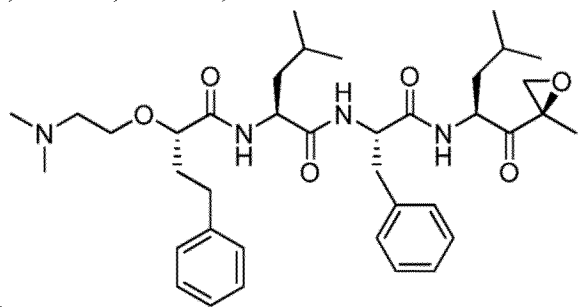 --.

At Column 50, Line 60, Claim 9, the recitation of " 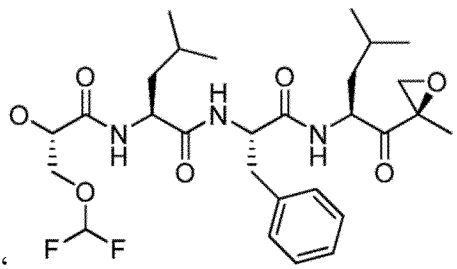 " should read

-- 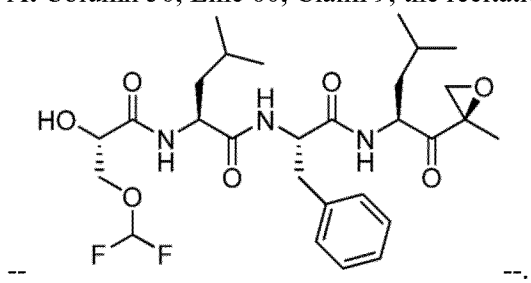 --.